(12) United States Patent
Cai et al.

(10) Patent No.: US 11,453,667 B2
(45) Date of Patent: Sep. 27, 2022

(54) PYRIDONE-PYRIMIDINE DERIVATIVE ACTING AS KRASG12C MUTEIN INHIBITOR

(71) Applicant: MEDSHINE DISCOVERY INC., Jiangsu (CN)

(72) Inventors: Yaxian Cai, Shanghai (CN); Zhaobing Xu, Shanghai (CN); Hailong Yang, Shanghai (CN); Shiqi Han, Shanghai (CN); Guoping Hu, Shanghai (CN); Lihong Hu, Shanghai (CN); Charles Z. Ding, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 311 days.

(21) Appl. No.: 16/962,951

(22) PCT Filed: Jan. 18, 2019

(86) PCT No.: PCT/CN2019/072393
§ 371 (c)(1),
(2) Date: Jul. 17, 2020

(87) PCT Pub. No.: WO2019/141250
PCT Pub. Date: Jul. 25, 2019

(65) Prior Publication Data
US 2021/0371411 A1    Dec. 2, 2021

(30) Foreign Application Priority Data

Jan. 19, 2018 (CN) .......................... 201810055396.8
Jun. 29, 2018 (CN) .......................... 201810712103.9

(51) Int. Cl.
C07D 471/04 (2006.01)
C07D 519/00 (2006.01)
A61P 35/00 (2006.01)

(52) U.S. Cl.
CPC ............ *C07D 471/04* (2013.01); *A61P 35/00* (2018.01); *C07D 519/00* (2013.01)

(58) Field of Classification Search
CPC ....................................................... A61P 35/00
USPC .................................................. 514/210.16
See application file for complete search history.

(56) References Cited

FOREIGN PATENT DOCUMENTS

| WO | WO-2015054572 A1 | 4/2015 |
|----|------------------|--------|
| WO | WO-2016164675 A1 | 10/2016 |
| WO | WO-2016168540 A1 | 10/2016 |
| WO | WO-2017087528 A1 | 5/2017 |
| WO | WO-2017100546 A1 | 6/2017 |
| WO | WO-2017201161 A1 | 11/2017 |
| WO | 2018064510 | * 4/2018 |
| WO | WO-2018064510 A1 | 4/2018 |
| WO | WO-2018119183 A2 | 6/2018 |
| WO | WO-2018206539 A1 | 11/2018 |

OTHER PUBLICATIONS

CA Extended European Search Report regarding EP 19740933.7, dated Nov. 10, 2020.
Dec. 20, 2021 the Second Office Action issued in Chinese application No. 202011378153.1.
Dec. 20, 2021 the Second Office Action issued in Chinese application No. 202011378149.5.
Dec. 13, 2021 the First Office Action issued in Chinese application No. 202110310525.5.
Feb. 8, 2022 the First Office Action issued in Chinese application No. 201980009147.8.
Office Action regarding Chinese Application No. 202011378149.5, dated Jun. 28, 2021.
Office Action regarding Chinese Application No. 202011378153.1, dated Jun. 28, 2021.
Cox, Adrienne D., et al. "Drugging the Undruggable RAS: Mission Possible?" Nature Reviews Drug Discovery, vol. 13, No. 11, 2014, pp. 828-851. Crossref, doi:10.1038/nrd4389.
Ostrem, Jonathan M., et al. "K-Ras(G12C) Inhibitors Allosterically Control GTP Affinity and Effector Interactions." Nature, vol. 503, No. 7477, 2013, pp. 548-551. Crossref, doi:10.1038/nature12796.
Lito, P., et al. "Allele-Specific Inhibitors Inactivate Mutant Kras G12C by a Trapping Mechanism." Science, vol. 351, No. 6273, 2016, pp. 604-608. Crossref, doi:10.1126/science.aad6204.
Patricelli, M. P., et al. "Selective Inhibition of Oncogenic KRAS Output with Small Molecules Targeting the Inactive State." Cancer Discovery, vol. 6, No. 3, 2016, pp. 316-329. Crossref, doi:10.1158/2159-8290.cd-15-1105.

(Continued)

*Primary Examiner* — Niloofar Rahmani
(74) *Attorney, Agent, or Firm* — Harness, Dickey & Pierce, P.L.C.

(57) ABSTRACT

Provided are a class of KRAS G12C mutein inhibitors, which relate in particular to a compound represented by formula (I), an isomer thereof, and a pharmaceutically acceptable salt thereof.

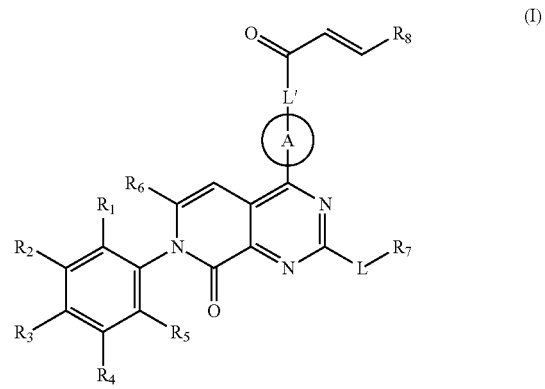

19 Claims, No Drawings

(56) References Cited

OTHER PUBLICATIONS

Janes, Matthew R., et al. "Targeting KRAS Mutant Cancers with a Covalent G12C-Specific Inhibitor." Cell, vol. 172, No. 3, 2018, pp. 578-589.e17. Crossref, doi:10.1016/j.cell.2018.01.006.
International Search Report regarding International Application No. PCT/CN2019/072393, dated Mar. 28, 2019.
Written Opinion of the International Searching Authority regarding International Application No. PCT/CN2019/072393, dated Mar. 28, 2019.
May 16, 2022 Chinese Office Action issued in Chinese Patent Application No. 2020113781495.

* cited by examiner

PYRIDONE-PYRIMIDINE DERIVATIVE ACTING AS KRASG12C MUTEIN INHIBITOR

CROSS-REFERENCE TO RELATED APPLICATIONS

This application is a U.S. National Phase Application under 35 U.S.C. 371 of International Application No. PCT/CN2019/072393, filed Jan. 18, 2019, which claims the benefit of Chinese Patent Application No. CN 201810055396.8, filed Jan. 19, 2018 and Chinese Patent Application No. CN 201810712103.9, filed Jun. 29, 2018. The entire disclosures of the above applications are incorporated herein by reference.

TECHNICAL FIELD

The present invention relates to a new substituted pyridone-pyrimidine derivative, in particular to a compound of formula (I) or an isomer and a pharmaceutically acceptable salt thereof, as well as the use of the compound of formula (I) or an isomer, a pharmaceutically acceptable salt and a pharmaceutical composition thereof in the preparation of a medicine for treating cancers.

BACKGROUND ARTS

The first RAS oncogene was found in rat sarcoma, and hence comes the name. RAS protein is a product expressed by the RAS gene, and refers to a class of closely related monomeric globulins consisting of 189 amino acids with a molecular weight of 21 KDa. The RAS protein can bind to guanine trinucleotide phosphate (GTP) or guanine dinucleotide phosphate (GDP). The active state of the RAS protein has effects on cell growth, differentiation, cytoskeleton, protein transport and secretion, and the activity thereof is regulated by binding to GTP or GDP: when the RAS protein binds to GDP, it is in a dormant state, i.e., "inactivated" state; when stimulated by a specific upstream cell growth factor, the RAS protein is induced to exchange GDP and binds to GTP, and the RAS protein is in the so called "activated" state. The RAS protein that binds to GTP can activate downstream proteins for signal transduction. The RAS protein itself has weak GTP hydrolytic activity and can hydrolyze GTP to GDP. In this way, the transition from the activated state to the inactivated state can be achieved. GAPs (GTPase activating proteins) are also required to participate in this hydrolysis process. They can interact with the RAS protein, greatly promoting the ability to hydrolyze GTP to GDP. The mutation of the RAS protein would affect its interaction with GAPs, and further affect its ability to hydrolyze GTP to GDP, making it always activated. The activated RAS protein continuously sends growth signals to downstream proteins, which leads to non-stop cell growth and differentiation, and eventually produce tumors. There are many members in the RAS gene family, among which the subfamilies closely related to various cancers mainly include Kirsten rat sarcoma viral oncogene homolog (KRAS), Harvey rat sarcoma viral oncogene homolog (HRAS) and neuroblastoma rat sarcoma viral oncogene homolog (NRAS). It has been found that about 30% of human tumors carry certain mutant RAS genes, in which KRAS mutations are the most significant, accounting for 86% of all RAS mutations. For the KRAS mutations, the most common mutations appear on residues of glycine 12 (G12), glycine 13 (G13) and glutamine 61 (Q61), with G12 mutations accounting for 83%.

G12C mutation is a relatively common subtype of the KRAS gene mutations, and refers to the mutation of glycine 12 to cysteine. KRAS G12C mutation is the most common in lung cancer, and according to the data reported in the literature (Nat Rev Drug Discov 2014; 13: 828-851), the KRAS G12C mutation accounts for around 10% of all lung cancer patients.

At present, there is not much research on the KRAS G12C mutant protein as a frontier target. The literature (Nature. 2013; 503: 548-551) reported a class of covalently bound inhibitors targeting the KRAS G12C mutation; however, such compounds have low enzymatic activity and do not show activity at the cellular level. The literature (Science 2016; 351: 604-608, Cancer Discov 2016; 6: 316-29) reported a class of compounds showing a µM-level cellular anti-proliferative activity at the cellular level; however, such compounds have poor metabolic stability and an activity that is difficult to be further improved. In recent years, Araxes Pharma has applied for several patents for KRAS G12C inhibitors, for example, WO 2016164675 and WO 2016168540 reported a class of quinazoline derivatives having high enzyme binding activity and showing a µM-level cellular anti-proliferative activity, with stable structure and certain selectivity. In 2018, Amgen (WO 2018119183 A2) and AstraZeneca (WO 2018206539) respectively published patents for KRAS G12C inhibitors, and in July 2018, a phase 1 clinical study on Amgen's KRAS G12C inhibitor AMG 510 was initiated. All the KRAS G12C inhibitors reported in current literatures have an acrylamide fragment, which interacts as a Michael addition receptor with cysteine residues on the KRASG12C mutant protein to form a covalently bound complex. In 2018, LIU, Yi et al. reported in Cell (Matthew R. Janes, Yi Liu et al., Cell, 2018, 172, 578-589) ARS-1620, a covalently bound inhibitor targeting the KRAS G12C mutation, wherein the compound has good metabolic stability, shows a nM-level cellular anti-proliferative activity at the cellular level, and can effectively inhibit tumor growth in a subcutaneous xenograft tumor model of pancreatic cancer MIA-Paca2 cell.

WO 2018/064510 A1 discloses a compound Ex3, but no characterization data and test results are given.

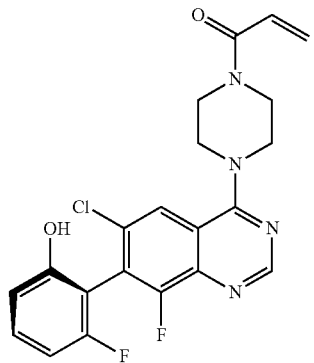

ARS-1620

-continued

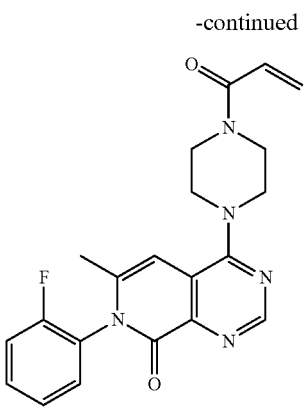

Compound Ex3

CONTENT OF THE PRESENT INVENTION

The present invention provides a compound of formula (I), a pharmaceutically acceptable salt thereof or an isomer thereof,

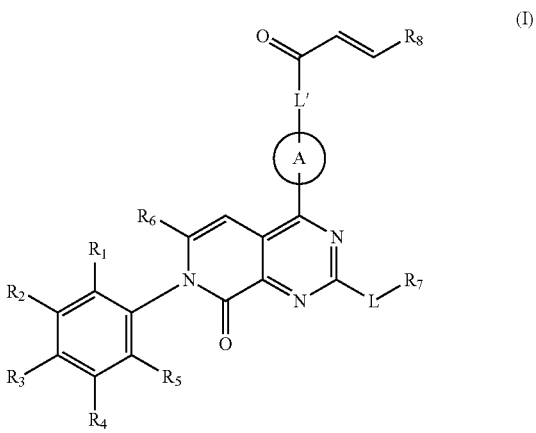

wherein ring A is selected from 3-8 membered heterocycloalkyl, and the 3-8 membered heterocycloalkyl is optionally substituted with 1, 2 or 3 R;

$R_1$, $R_2$, $R_3$, $R_4$ and $R_5$ are each independently selected from H, halogen, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3 R;

or $R_1$ and $R_2$ are connected together to form ring B;
or $R_2$ and $R_3$ are connected together to form ring B;
or $R_3$ and $R_4$ are connected together to form ring B;
or $R_4$ and $R_5$ are connected together to form ring B;

ring B is selected from phenyl, $C_{5-6}$ cycloalkenyl, 5-6 membered heterocycloalkenyl and 5-6 membered heteroaryl, and the phenyl, $C_{5-6}$ cycloalkenyl, 5-6 membered heterocycloalkenyl and 5-6 membered heteroaryl are optionally substituted with 1, 2 or 3 $R_a$;

$R_a$ is selected from halogen, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3 R;

$R_6$ is selected from H, halogen and $C_{1-6}$ alkyl, and the $C_{1-6}$ alkyl is optionally substituted with 1, 2 or 3 R;

$R_7$ is selected from H, CN, $NH_2$, $C_{1-8}$ alkyl, $C_{1-8}$ heteroalkyl, 4-6 membered heterocycloalkyl, 5-6 membered heteroaryl and $C_{5-6}$ cycloalkyl, and the $C_{1-8}$ alkyl, $C_{1-8}$ heteroalkyl, 4-6 membered heterocycloalkyl, 5-6 membered heteroaryl and $C_{5-6}$ cycloalkyl are optionally substituted with 1, 2 or 3 R;

L is selected from a single bond, —NH—, —S—, —O—, —C(=O)—, —C(=S)—, —$CH_2$—, —$CH(R_b)$— and —$C(R_b)_2$—;

L' is selected from a single bond and —NH—;

$R_b$ is selected from $C_{1-3}$ alkyl and $C_{1-3}$ heteroalkyl, and the $C_{1-3}$ alkyl and $C_{1-3}$ heteroalkyl are optionally substituted with 1, 2 or 3 R;

$R_8$ is selected from H, $C_{1-6}$ alkyl and $C_{1-6}$ heteroalkyl, and the $C_{1-6}$ alkyl and $C_{1-6}$ heteroalkyl are optionally substituted with 1, 2 or 3 R;

R is selected from halogen, OH, $NH_2$, CN, $C_{1-6}$ alkyl, $C_{1-6}$ heteroalkyl and $C_{3-6}$ membered cycloalkyl, and the $C_{1-6}$ alkyl, $C_{1-6}$ heteroalkyl and $C_{3-6}$ membered cycloalkyl are optionally substituted with 1, 2 or 3 R';

R' is selected from F, Cl, Br, I, OH, $NH_2$, CN, $CH_3$, $CH_3CH_2$, $CH_3O$, $CF_3$, $CHF_2$, $CH_2F$, cyclopropyl, propyl, isopropyl, $N(CH_3)_2$ and $NH(CH_3)$;

"hetero" means a heteroatom or a heteroatomic group, the "hetero" in the 3-8 membered heterocycloalkyl, $C_{1-6}$ heteroalkyl, 5-6 membered heterocycloalkenyl, 5-6 membered heteroaryl, $C_{1-8}$ heteroalkyl, 4-6 membered heterocycloalkyl and $C_{1-3}$ heteroalkyl is each independently selected from —C(=O)N(R)—, —N(R)—, —NH—, N, —O—, —S—, —C(=O)O—, —C(=O)—, —C(=S)—, —S(=O)—, —S(=O)$_2$— and —N(R)C(=O)N(R)—;

in any of the cases above, the number of heteroatoms or heteroatomic groups is each independently selected from 1, 2 and 3.

In some embodiments of the present invention, the above-mentioned R is selected from F, Cl, Br, I, OH, $NH_2$, CN, $CH_3$, $CH_3CH_2$, $CH_3O$, $CF_3$, $CHF_2$, $CH_2F$, cyclopropyl, propyl, isopropyl, $N(CH_3)_2$, $NH(CH_3)$ and $N(CH_2CH_3)_2$.

In some embodiments of the present invention, the above-mentioned ring A is selected from aziridinyl, azetidinyl, pyrrolidinyl, piperidyl, piperazinyl, 1,4-diazacycloheptyl and 3,6-diazabicyclo [3.2.0] heptyl, and the aziridinyl, azetidinyl, pyrrolidinyl, piperidyl, piperazinyl, 1,4-diazacycloheptyl and 3,6-diazabicyclo [3.2.0] heptyl are optionally substituted with 1, 2 or 3 R.

In some embodiments of the present invention, the above-mentioned $R_1$, $R_2$, $R_3$, $R_4$ and $R_5$ are each independently selected from H, F, Cl, Br, I, OH, $NH_2$, CN, $CH_3$, $CH_3CH_2$, $(CH_3)_2CH$, $CH_3O$, $CH_3NH$ and $CH_3NH(C=O)O$, and the $CH_3$, $CH_3CH_2$, $(CH_3)_2CH$, $CH_3O$, $CH_3NH$ and $CH_3NH(C=O)O$ are optionally substituted with 1, 2 or 3 R.

In some embodiments of the present invention, the above-mentioned $R_1$, $R_2$, $R_3$, $R_4$ and $R_5$ are each independently selected from H, F, Cl, Br, I, OH, $NH_2$, CN, $CH_3$, $CH_3CH_2$, $(CH_3)_2CH$, $CH_3O$, $CH_3NH$, $(CH_3)_2N$, $(CH_3)_2N(C=O)O$ and $CH_3NH(C=O)O$.

In some embodiments of the present invention, the above-mentioned ring B is selected from pyrazolyl, imidazolyl, pyrrolyl, thienyl, furyl, triazolyl, oxazolyl, isoxazolyl, thiazolyl, isothiazolyl, phenyl, pyridyl, pyrimidinyl, pyridazinyl, triazinyl, morpholinyl, cyclopentenyl and cyclohexenyl, and the pyrazolyl, imidazolyl, pyrrolyl, thienyl, furyl, triazolyl, oxazolyl, isoxazolyl, thiazolyl, isothiazolyl, phenyl, pyridyl, pyrimidinyl, pyridazinyl, triazinyl, morpholinyl, cyclopentenyl and cyclohexenyl are optionally substituted with 1, 2 or 3 $R_a$.

In some embodiments of the present invention, the above-mentioned $R_a$ is selected from F, Cl, Br, I, OH, $NH_2$, CN, $CH_3$, $CH_3CH_2$, $(CH_3)_2CH$, $CH_3O$ and $CH_3C(=O)$.

In some embodiments of the present invention, the above-mentioned ring B is selected from phenyl, pyrazolyl, 1-methyl-1H-pyrazolyl and 1-(1H-pyrazole-1-yl)ethanone group.

In some embodiments of the present invention, the above-mentioned $R_6$ is selected from H, F, Cl, Br, I and $C_{1-3}$ alkyl, and the $C_{1-3}$ alkyl is optionally substituted with 1, 2 or 3 R.

In some embodiments of the present invention, the above-mentioned $R_6$ is selected from H, F, Cl, Br, I, $CH_3$, $CF_3$, $CHF_2$ and $CH_2F$.

In some embodiments of the present invention, the above-mentioned $R_7$ is selected from H, CN, $NH_2$, $C_{1-6}$ alkyl, $C_{1-6}$ heteroalkyl, morpholinyl, piperidyl, azetidinyl, azacyclopentanyl, pyrazolyl, imidazolyl, oxazolyl, isoxazolyl, thiazolyl, isothiazolyl, cyclohexyl, cyclopentanyl, phenyl, pyridyl, pyridazinyl, pyrimidinyl and pyrazinyl, and the $C_{1-6}$ alkyl, $C_{1-6}$ heteroalkyl, morpholinyl, piperidyl, azetidinyl, azacyclopentanyl, pyrazolyl, imidazolyl, oxazolyl, isoxazolyl, thiazolyl, isothiazolyl, cyclohexyl, cyclopentanyl, phenyl, pyridyl, pyridazinyl, pyrimidinyl and pyrazinyl are optionally substituted with 1, 2 or 3 R.

In some embodiments of the present invention, the above-mentioned $R_7$ is selected from H, $CH_3$, CN, $NH_2$,

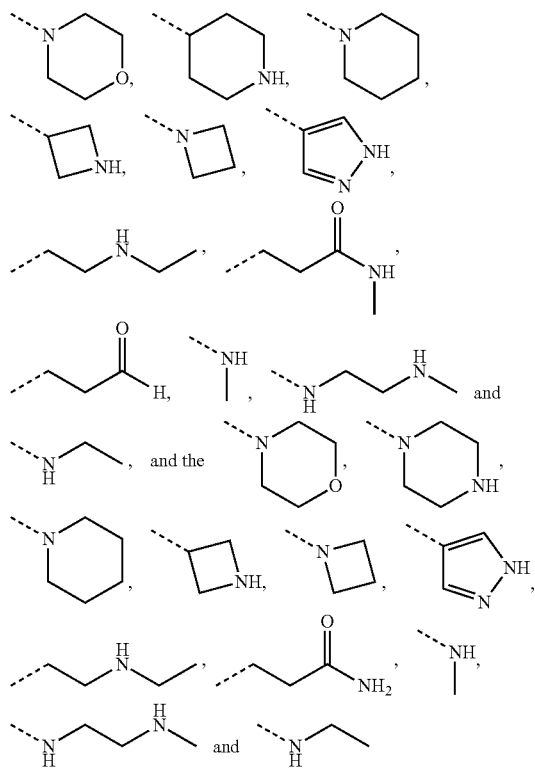

are optionally substituted with 1, 2 or 3 R.

In some embodiments of the present invention, the above-mentioned $R_7$ is selected from H, $CH_3$, CN, $NH_2$,

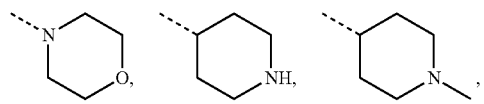

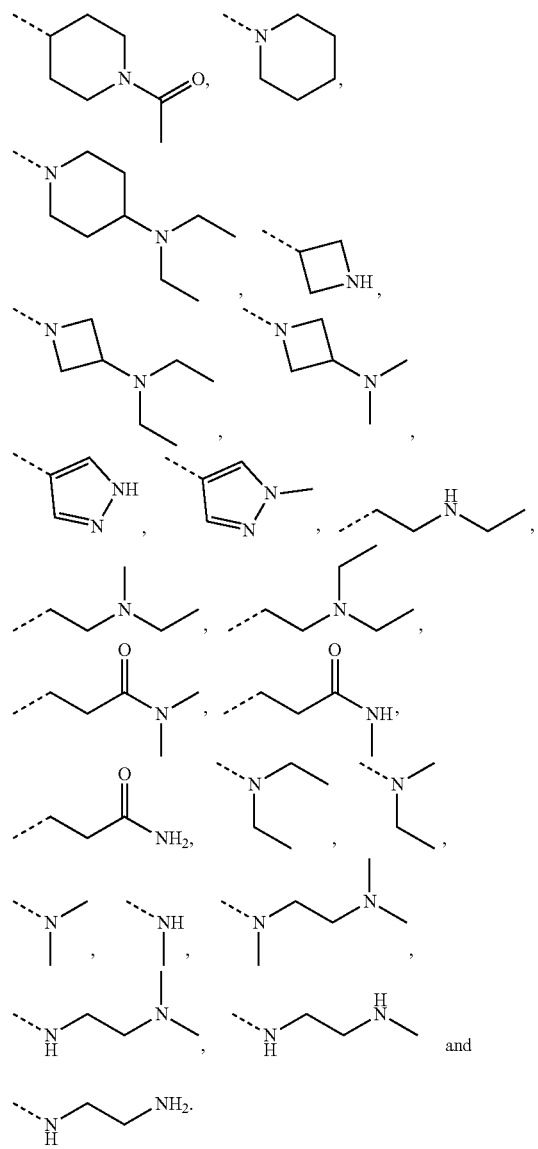

In some embodiments of the present invention, the above-mentioned $R_8$ is selected from H, $C_{1-4}$ alkyl and $C_{1-4}$ heteroalkyl, and the $C_{1-4}$ alkyl and $C_{1-4}$ heteroalkyl are optionally substituted with 1, 2 or 3 R.

In some embodiments of the present invention, the above-mentioned $R_8$ is selected from H, $CH_3$, $CH_3CH_2$, $(CH_3)_2CHCH_2$, $(CH_3)_2CH$, $CH_3O$, $CH_3NH$, $(CH_3)_2N$, $(CH_3)_2NCH_2$ and $CH_3NHCH_2$.

In some embodiments of the present invention, the above-mentioned structural unit

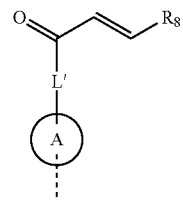

is selected from

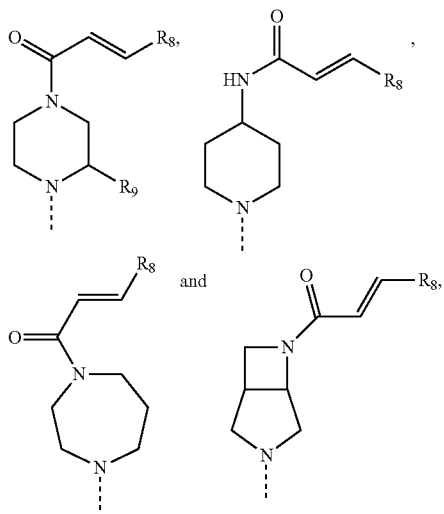

wherein $R_9$ is selected from H and $C_{1-3}$ alkyl.

In some embodiments of the present invention, the above-mentioned structural unit

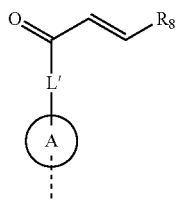

is selected from

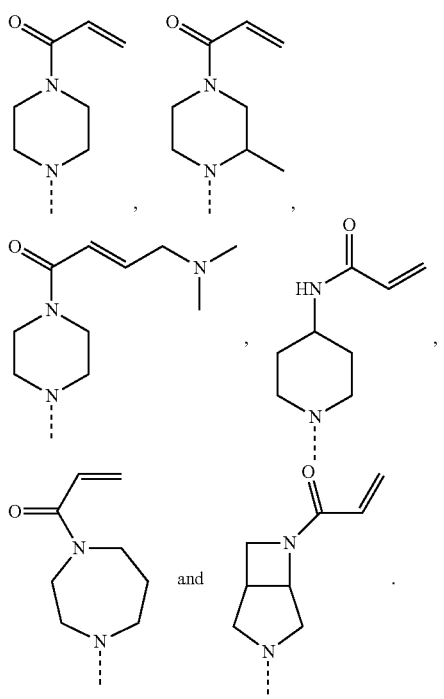

In some embodiments of the present invention, the above-mentioned structural unit

is selected from H, CN, $CH_3$, $CH_3CH_2$, $(CH_3)_2CH$, $(CH_3)_2N$, $(CH_3)_2NCH_2$,

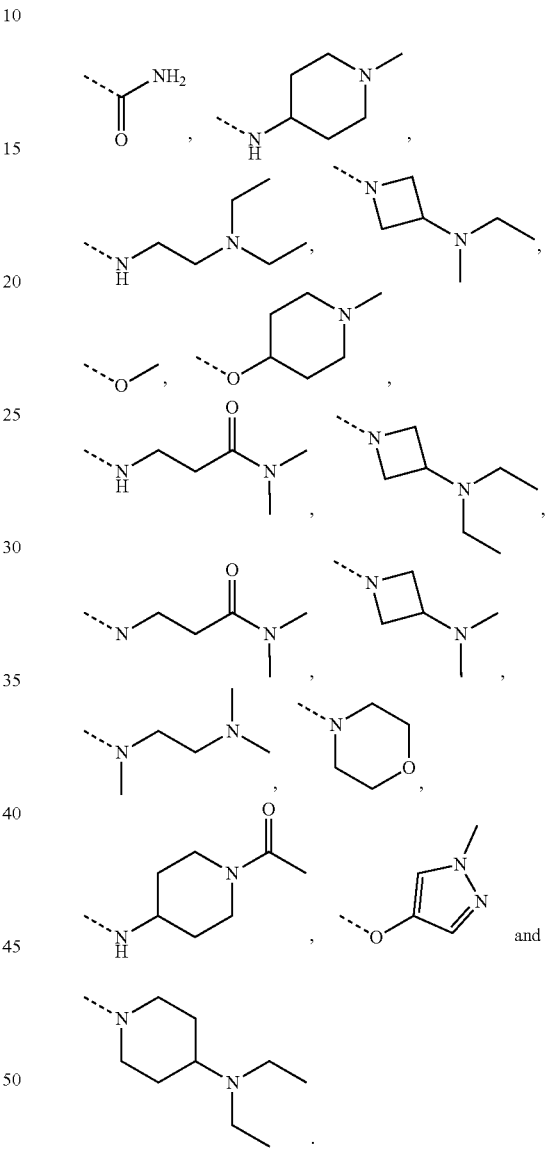

In some embodiments of the present invention, the above-mentioned structural unit

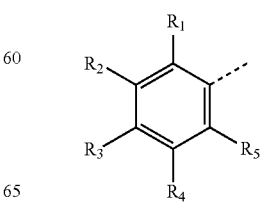

is selected from

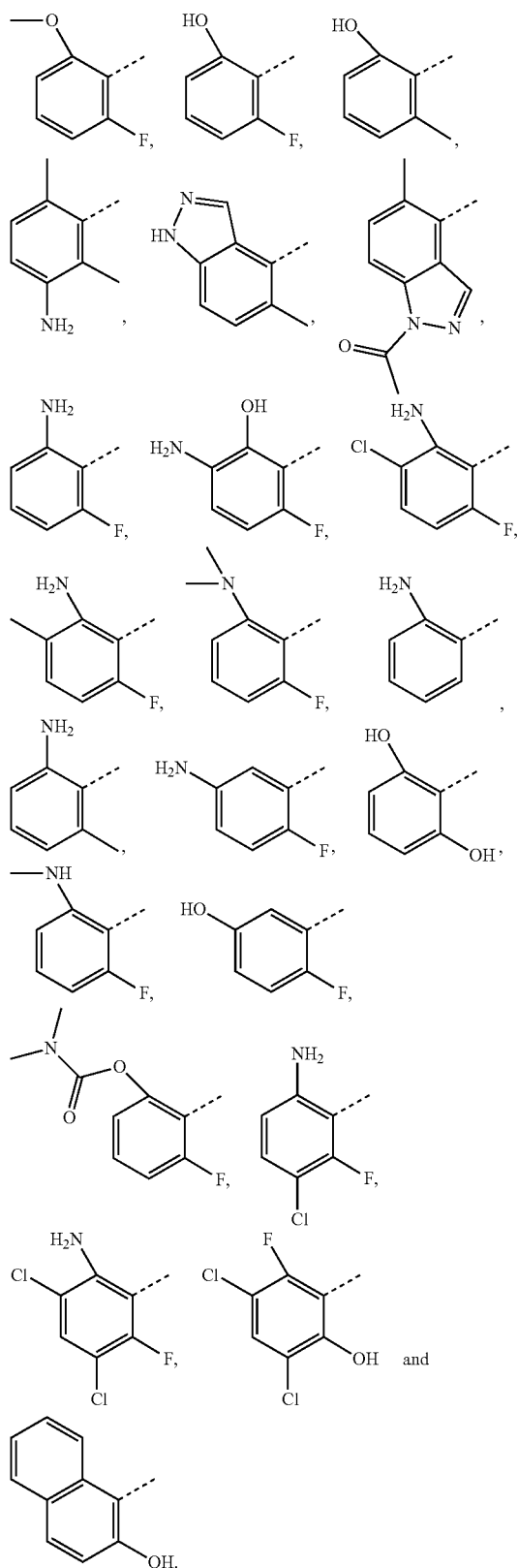

In some embodiments of the present invention, the above-mentioned R is selected from F, Cl, Br, I, OH, $NH_2$, CN, $CH_3$, $CH_3CH_2$, $CH_3O$, $CF_3$, $CHF_2$, $CH_2F$, cyclopropyl, propyl, isopropyl, $N(CH_3)_2$, $NH(CH_3)$ and $N(CH_2CH_3)_2$, and other variables are as defined in the present invention.

In some embodiments of the present invention, the above-mentioned ring A is selected from aziridinyl, azetidinyl, pyrrolidinyl, piperidyl, piperazinyl, 1,4-diazacycloheptyl and 3,6-diazabicyclo [3.2.0] heptyl, and the aziridinyl, azetidinyl, pyrrolidinyl, piperidyl, piperazinyl, 1,4-diazacycloheptyl and 3,6-diazabicyclo[3.2.0]heptyl are optionally substituted with 1, 2 or 3 R, and other variables are as defined in the present invention.

In some embodiments of the present invention, the above-mentioned $R_1$, $R_2$, $R_3$, $R_4$ and $R_5$ are each independently selected from H, F, Cl, Br, I, OH, $NH_2$, CN, $CH_3$, $CH_3CH_2$, $(CH_3)_2CH$, $CH_3O$, $CH_3NH$ and $CH_3NH(C=O)O$, and the $CH_3$, $CH_3CH_2$, $(CH_3)_2CH$, $CH_3O$, $CH_3NH$ and $CH_3NH(C=O)O$ are optionally substituted with 1, 2 or 3 R, and other variables are as defined in the present invention.

In some embodiments of the present invention, the above-mentioned $R_1$, $R_2$, $R_3$, $R_4$ and $R_5$ are each independently selected from H, F, Cl, Br, I, OH, $NH_2$, CN, $CH_3$, $CH_3CH_2$, $(CH_3)_2CH$, $CH_3O$, $CH_3NH$, $(CH_3)_2N$, $(CH_3)_2N(C=O)O$ and $CH_3NH(C=O)O$, and other variables are as defined in the present invention.

In some embodiments of the present invention, the above-mentioned ring B is selected from pyrazolyl, imidazolyl, pyrrolyl, thienyl, furyl, triazolyl, oxazolyl, isoxazolyl, thiazolyl, isothiazolyl, phenyl, pyridyl, pyrimidinyl, pyridazinyl, triazinyl, morpholinyl, cyclopentenyl and cyclohexenyl, and the pyrazolyl, imidazolyl, pyrrolyl, thienyl, furyl, triazolyl, oxazolyl, isoxazolyl, thiazolyl, isothiazolyl, phenyl, pyridyl, pyrimidinyl, pyridazinyl, triazinyl, morpholinyl, cyclopentenyl and cyclohexenyl are optionally substituted with 1, 2 or 3 $R_a$, and other variables are as defined in the present invention.

In some embodiments of the present invention, the above-mentioned $R_a$ is selected from F, Cl, Br, I, OH, $NH_2$, CN, $CH_3$, $CH_3CH_2$, $(CH_3)_2CH$, $CH_3O$ and $CH_3C(=O)$, and other variables are as defined in the present invention.

In some embodiments of the present invention, the above-mentioned ring B is selected from phenyl, pyrazolyl, 1-methyl-1H-pyrazolyl and 1-(1H-pyrazole-1-yl)ethanone group, and other variables are as defined in the present invention.

In some embodiments of the present invention, the above-mentioned $R_6$ is selected from H, F, Cl, Br, I and $C_{1-3}$ alkyl, and the $C_{1-3}$ alkyl is optionally substituted with 1, 2 or 3 R, and other variables are as defined in the present invention.

In some embodiments of the present invention, the above-mentioned $R_6$ is selected from H, F, Cl, Br, I, $CH_3$, $CF_3$, $CHF_2$ and $CH_2F$, and other variables are as defined in the present invention.

In some embodiments of the present invention, the above-mentioned $R_7$ is selected from H, CN, $NH_2$, $C_{1-6}$ alkyl, $C_{1-6}$ heteroalkyl, morpholinyl, piperidyl, azetidinyl, azacyclopentanyl, pyrazolyl, imidazolyl, oxazolyl, isoxazolyl, thiazolyl, isothiazolyl, cyclohexyl, cyclopentanyl, phenyl, pyridyl, pyridazinyl, pyrimidinyl and pyrazinyl, and the $C_{1-6}$ alkyl, $C_{1-6}$ heteroalkyl, morpholinyl, piperidyl, azetidinyl, azacyclopentanyl, pyrazolyl, imidazolyl, oxazolyl, isoxazolyl, thiazolyl, isothiazolyl, cyclohexyl, cyclopentanyl, phenyl, pyridyl, pyridazinyl, pyrimidinyl and pyrazinyl are optionally substituted with 1, 2 or 3 R, and other variables are as defined in the present invention.

In some embodiments of the present invention, the above-mentioned $R_7$ is selected from H, $CH_3$, CN, $NH_2$,

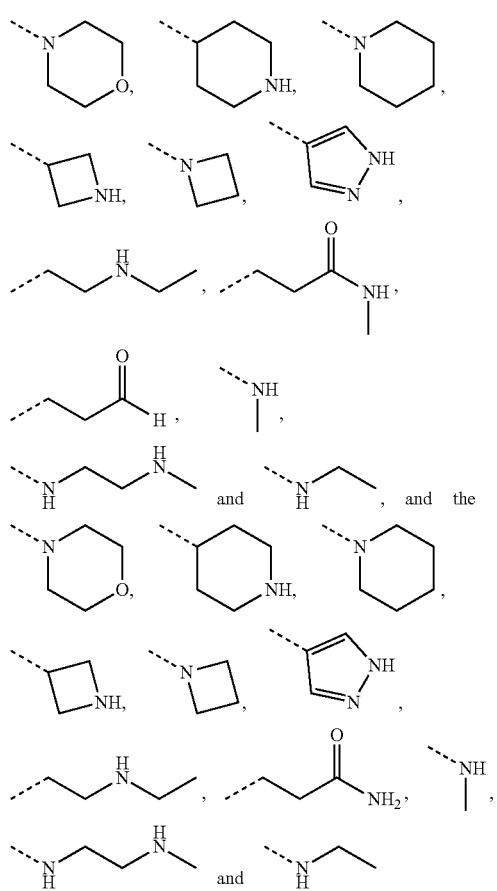

are optionally substituted with 1, 2 or 3 R, and other variables are as defined in the present invention.

In some embodiments of the present invention, the above-mentioned $R_7$ is selected from H, $CH_3$, CN, $NH_2$,

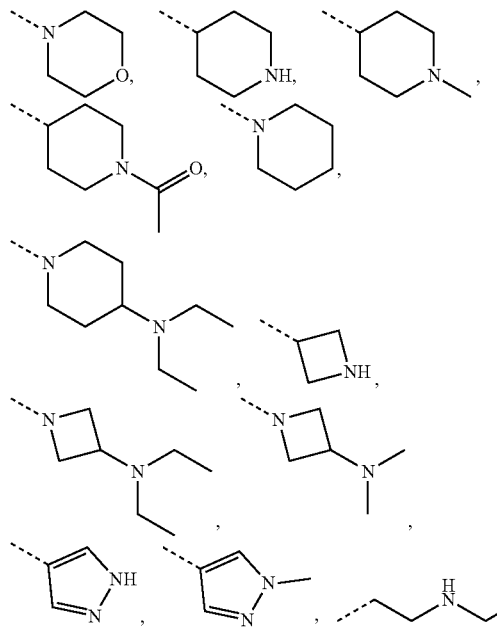

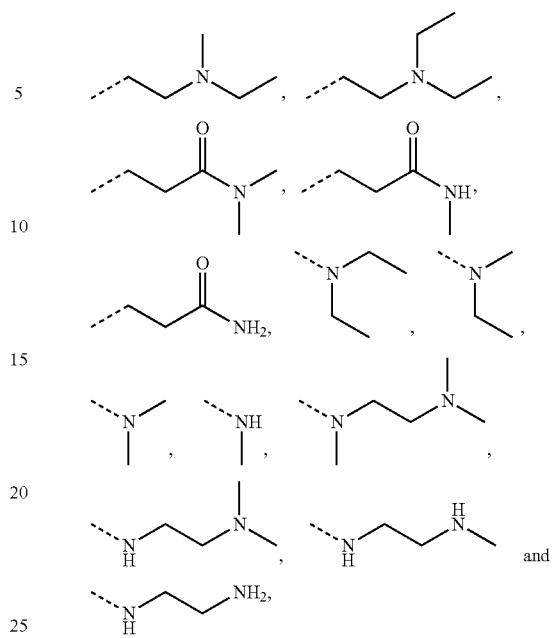

and other variables are as defined in the present invention.

In some embodiments of the present invention, the above-mentioned $R_8$ is selected from H, $C_{1-4}$ alkyl and $C_{1-4}$ heteroalkyl, and the $C_{1-4}$ alkyl and $C_{1-4}$ heteroalkyl are optionally substituted with 1, 2 or 3 R, and other variables are as defined in the present invention.

In some embodiments of the present invention, the above-mentioned $R_8$ is selected from H, $CH_3$, $CH_3CH_2$, $(CH_3)_2CHCH_2$, $(CH_3)_2CH$, $CH_3O$, $CH_3NH$, $(CH_3)_2N$, $(CH_3)_2NCH_2$ and $CH_3NHCH_2$, and other variables are as defined in the present invention.

In some embodiments of the present invention, the above-mentioned structural unit

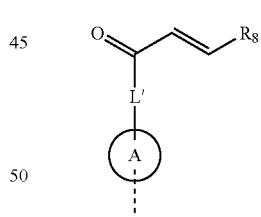

is selected from

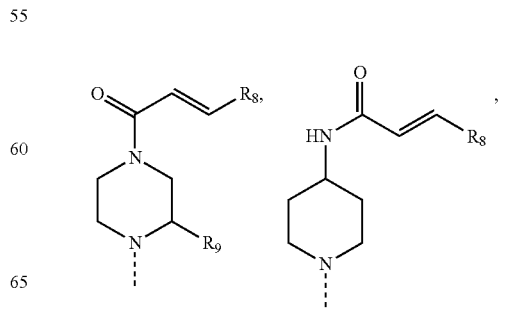

-continued

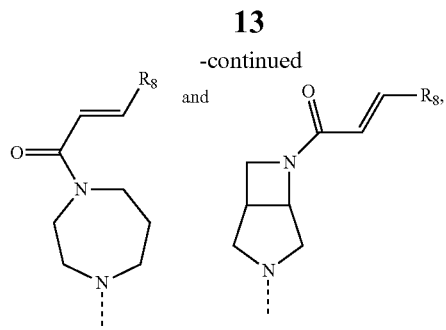

wherein R$_9$ is selected from H and C$_{1-3}$ alkyl, and other variables are as defined in the present invention.

In some embodiments of the present invention, the above-mentioned structural unit

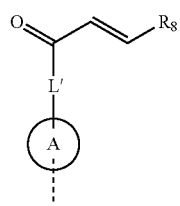

is selected from

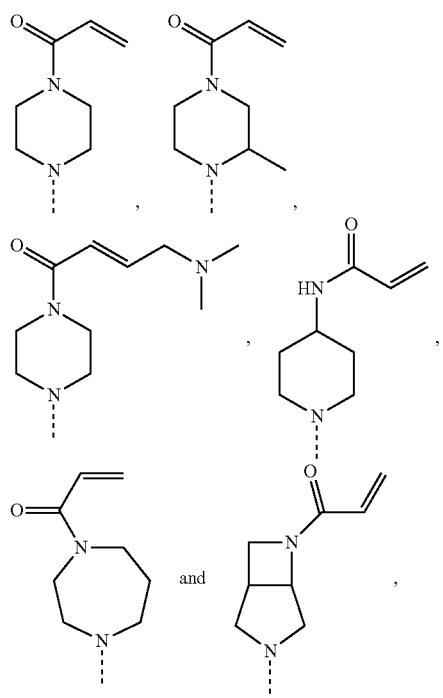

and other variables are as defined in the present invention.

In some embodiments of the present invention, the above-mentioned structural unit

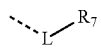

is selected from H, CN, CH$_3$, CH$_3$CH$_2$, (CH$_3$)$_2$CH, (CH$_3$)$_2$N, (CH$_3$)$_2$NCH$_2$,

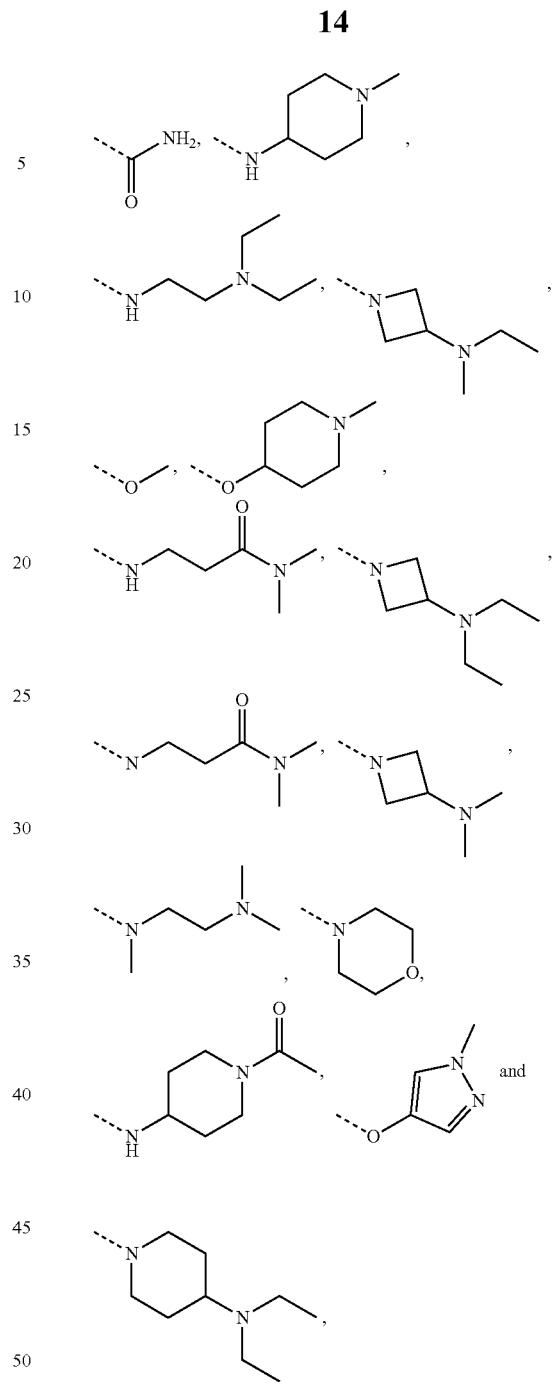

and other variables are as defined in the present invention.

In some embodiments of the present invention, the above-mentioned structural unit

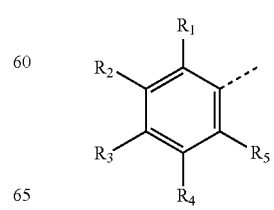

is selected from

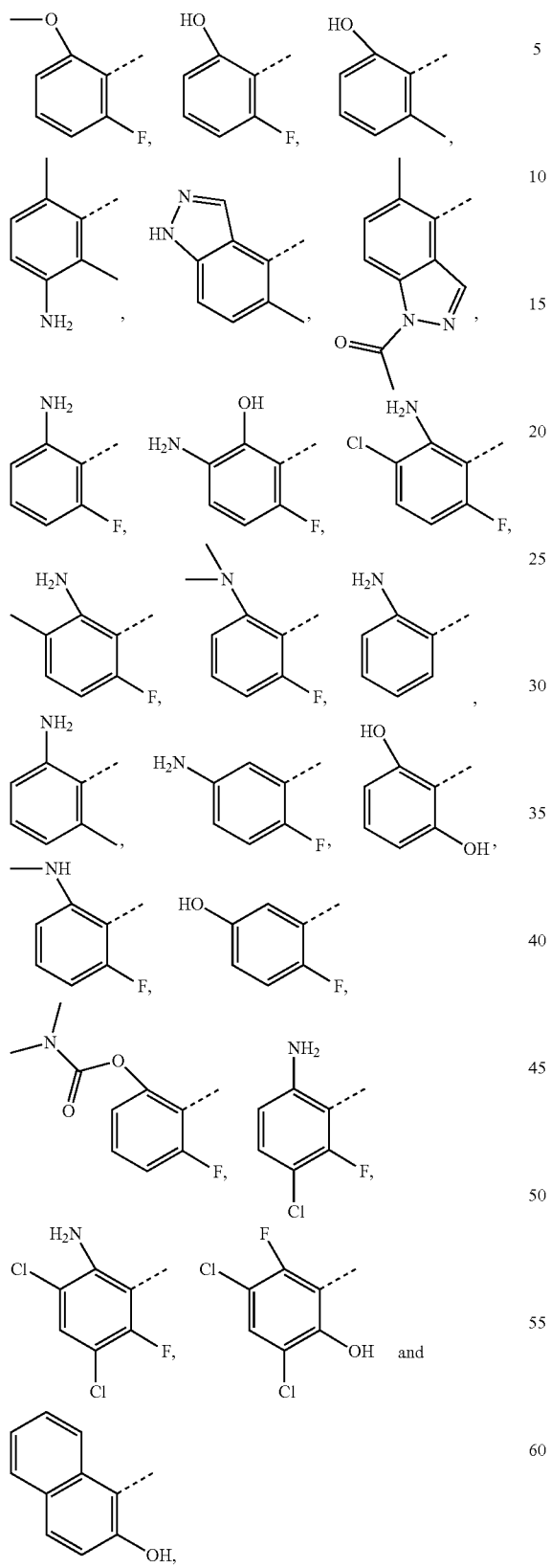

and other variables are as defined in the present invention.

In some embodiments of the present invention, the above-mentioned compound, a pharmaceutically acceptable salt thereof or an isomer thereof is selected from

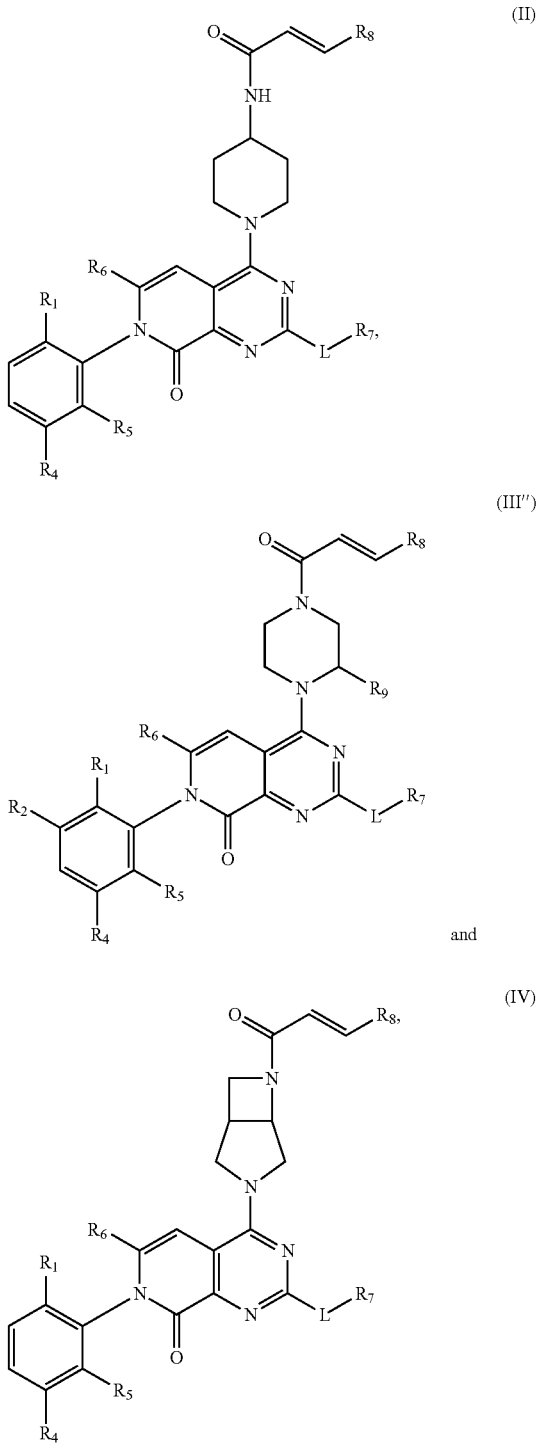

wherein L, $R_1$, $R_2$, $R_4$, $R_5$, $R_6$, $R_7$, $R_8$ and $R_9$ are as defined in the present invention.

In some embodiments of the present invention, the above-mentioned compound, a pharmaceutically acceptable salt thereof or an isomer thereof is selected from

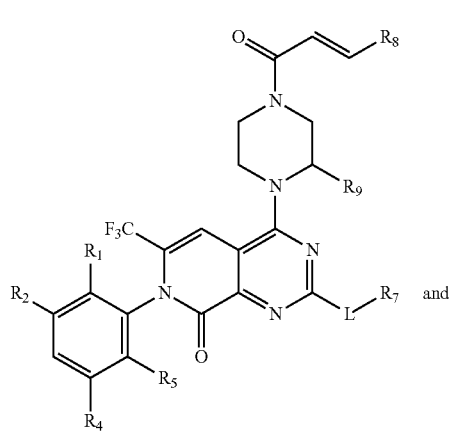
(III″-1)
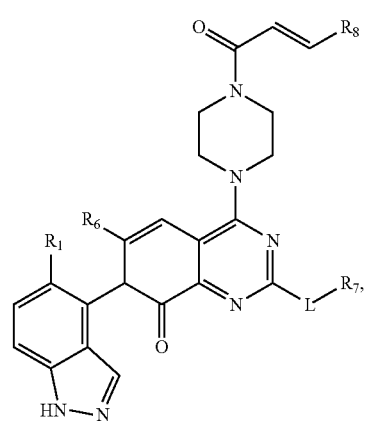
(VI-1)
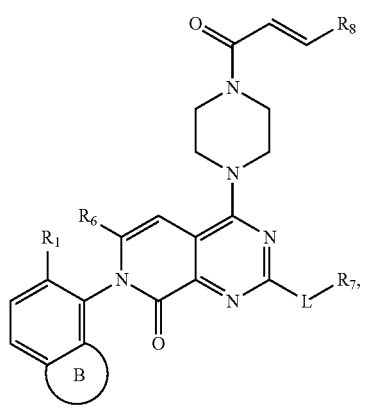
(VI)
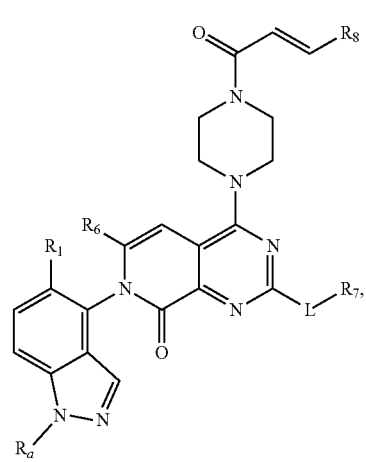
(VI-2)
wherein $R_1$, $R_2$, $R_4$, $R_5$, $R_6$, $R_7$, $R_8$, $R_9$, L and ring B are as defined in the present invention.
In some embodiments of the present invention, the above-mentioned compound, a pharmaceutically acceptable salt thereof or an isomer thereof is selected from
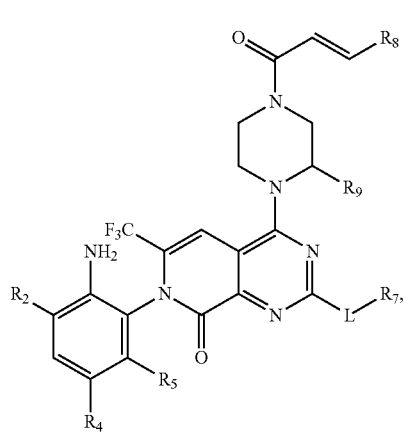
(III″-2)
(VI-3)

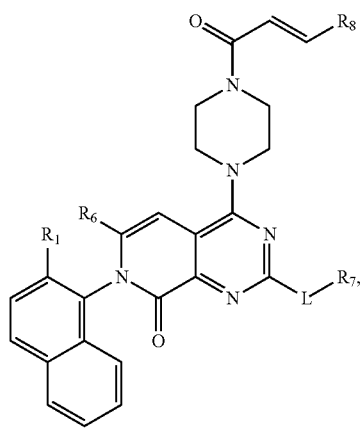
wherein $R_1$, $R_2$, $R_4$, $R_5$, $R_6$, $R_7$, $R_8$, L, $R_9$ and $R_a$ are as defined in the present invention.
The present invention also provides a compound of the following formula, a pharmaceutically acceptable salt thereof or an isomer thereof selected from
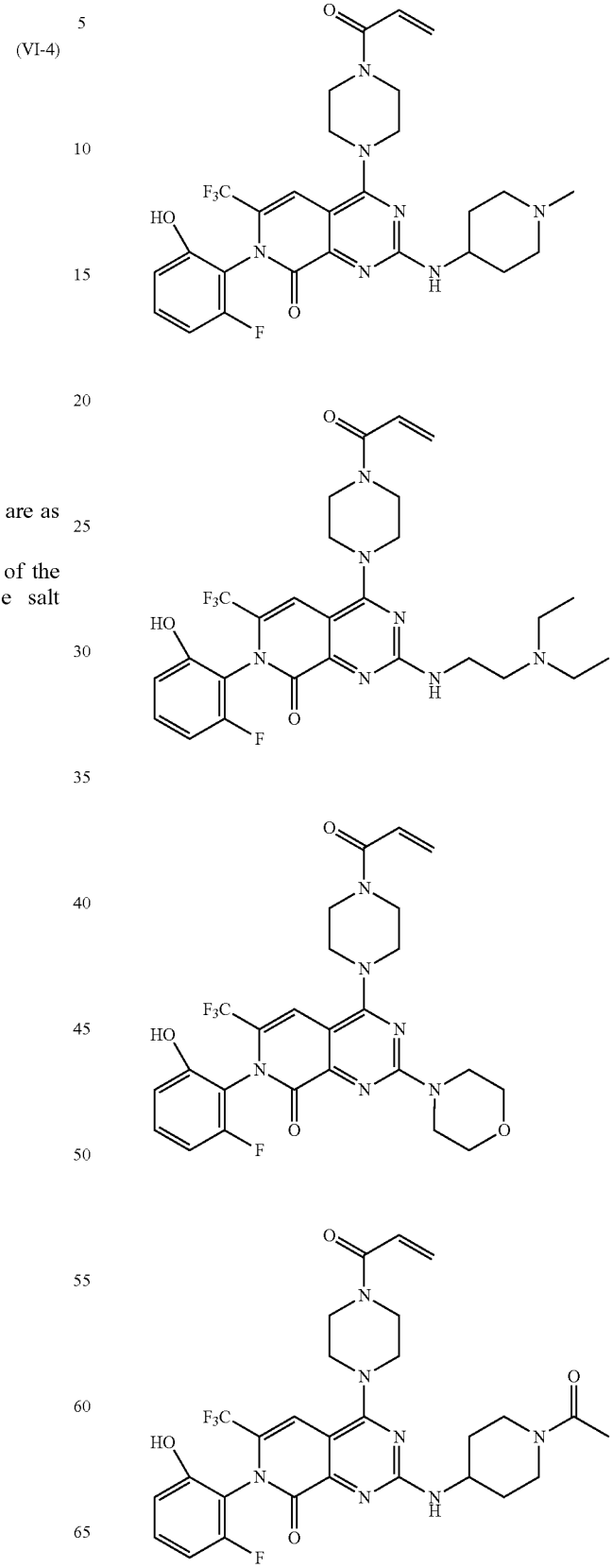

21
-continued
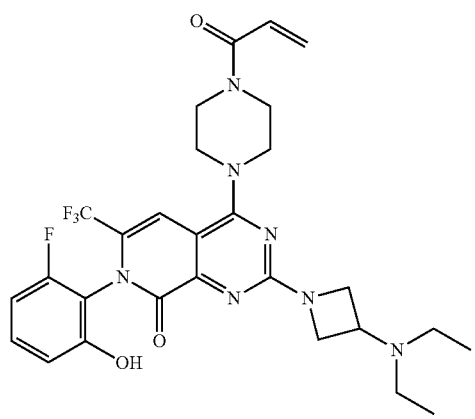
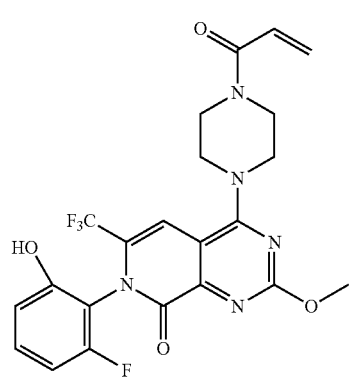
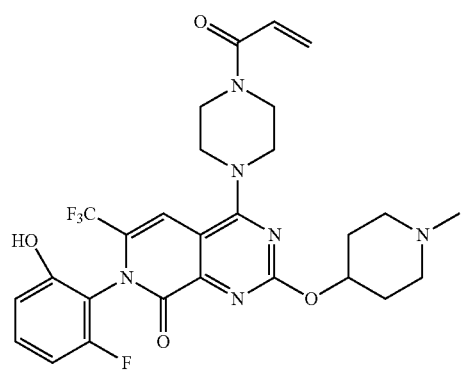
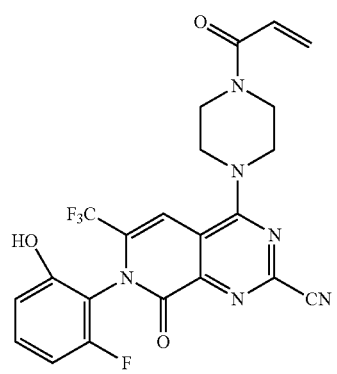
22
-continued
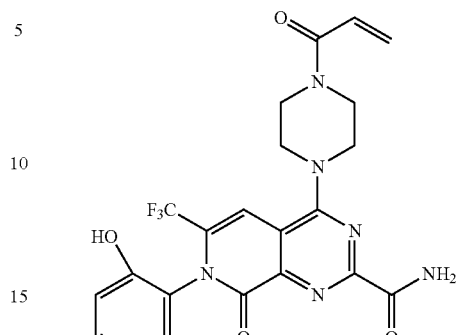
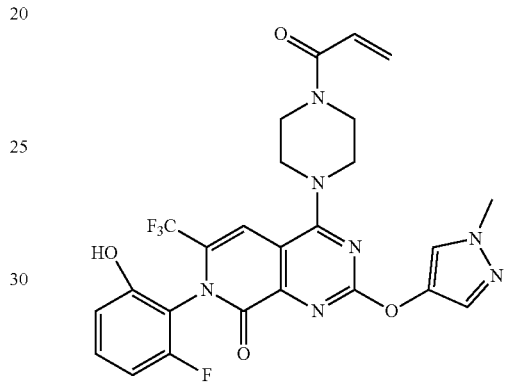
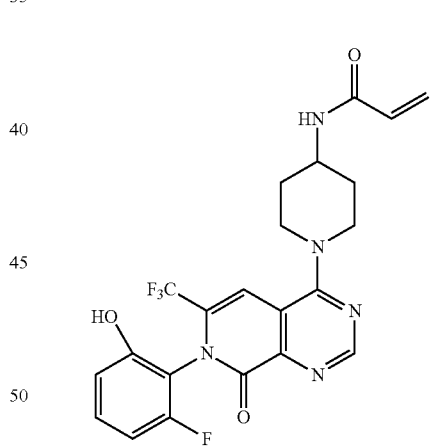

23
-continued
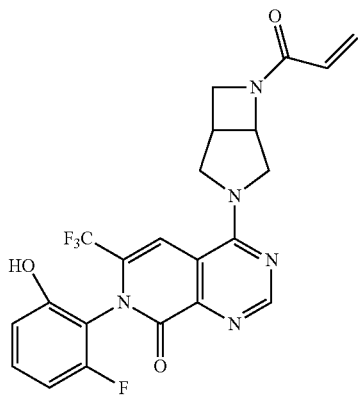
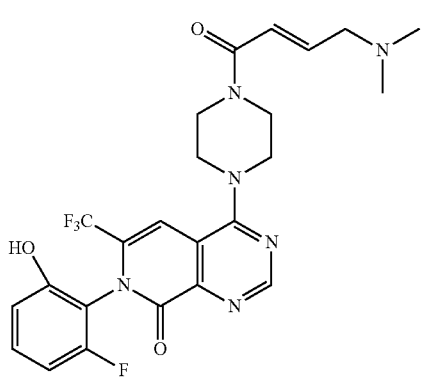
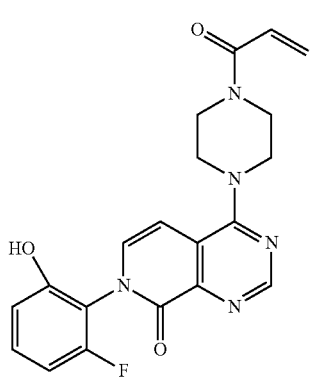
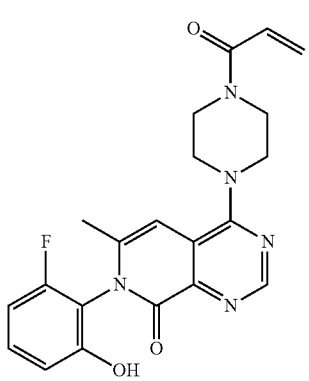
24
-continued
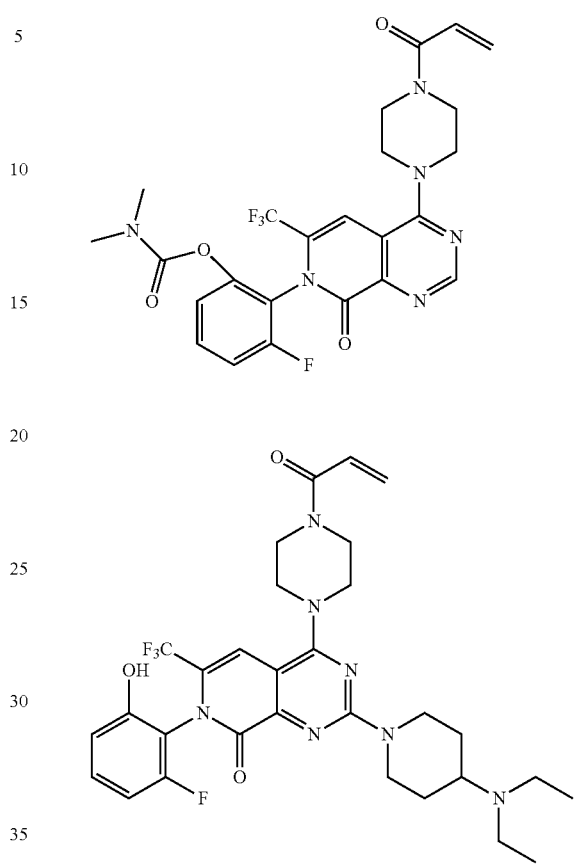
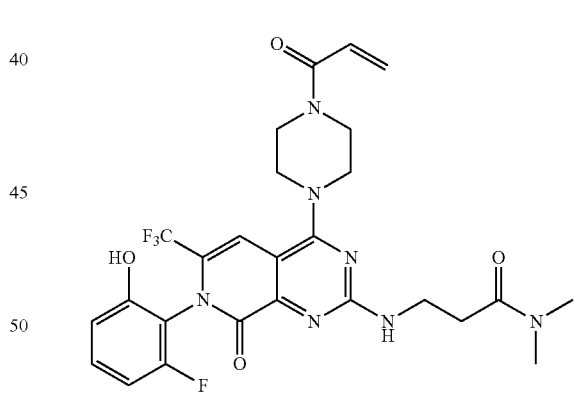
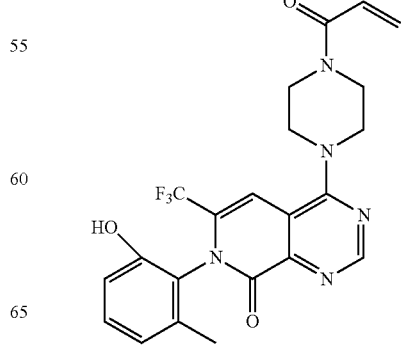

-continued
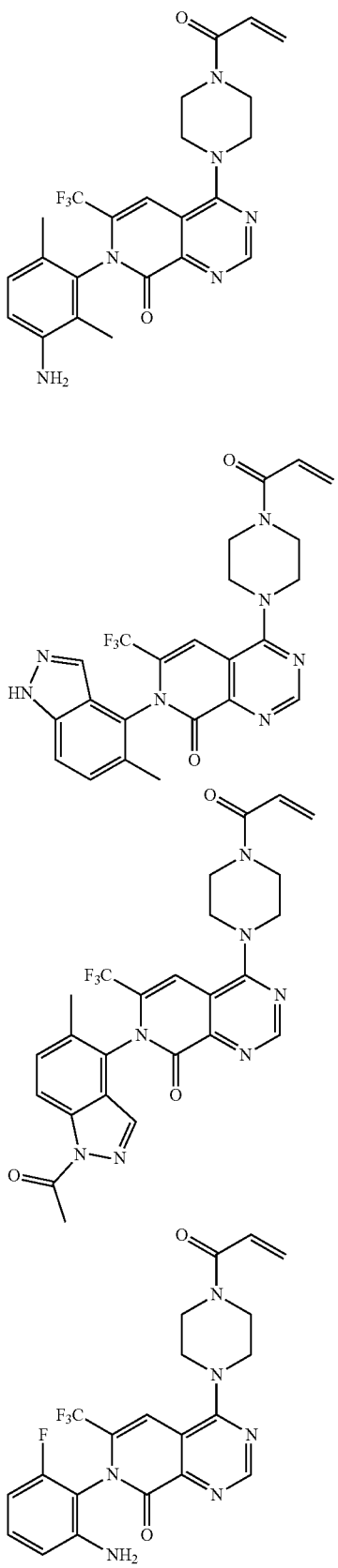
-continued
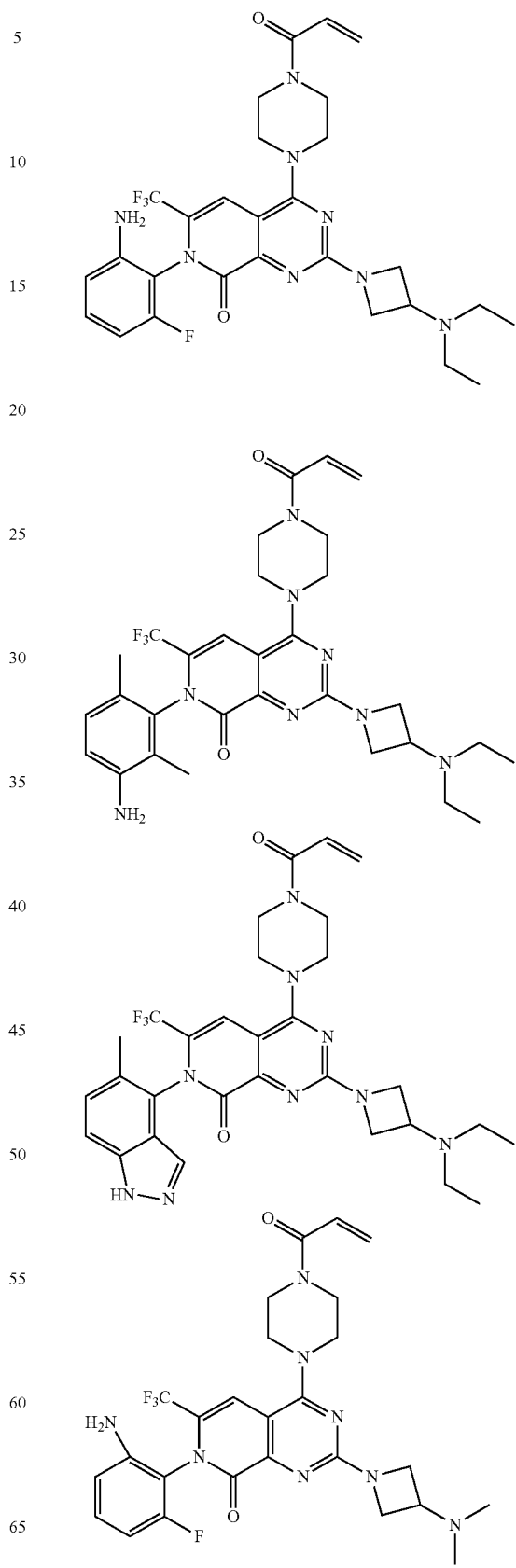

27
-continued
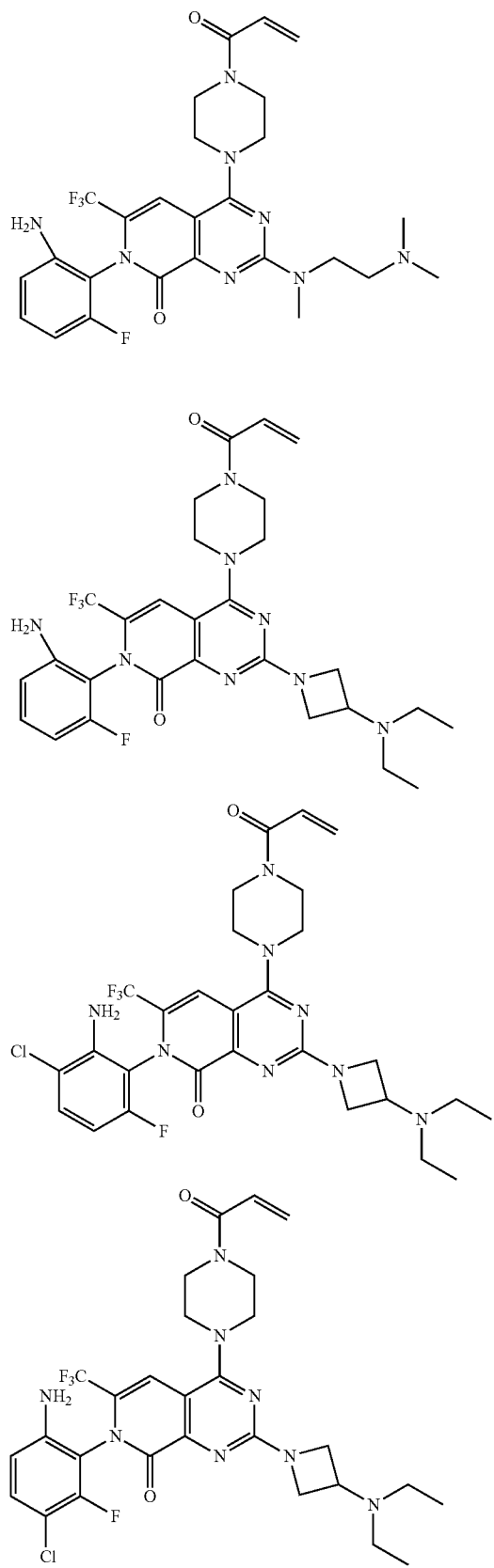
28
-continued
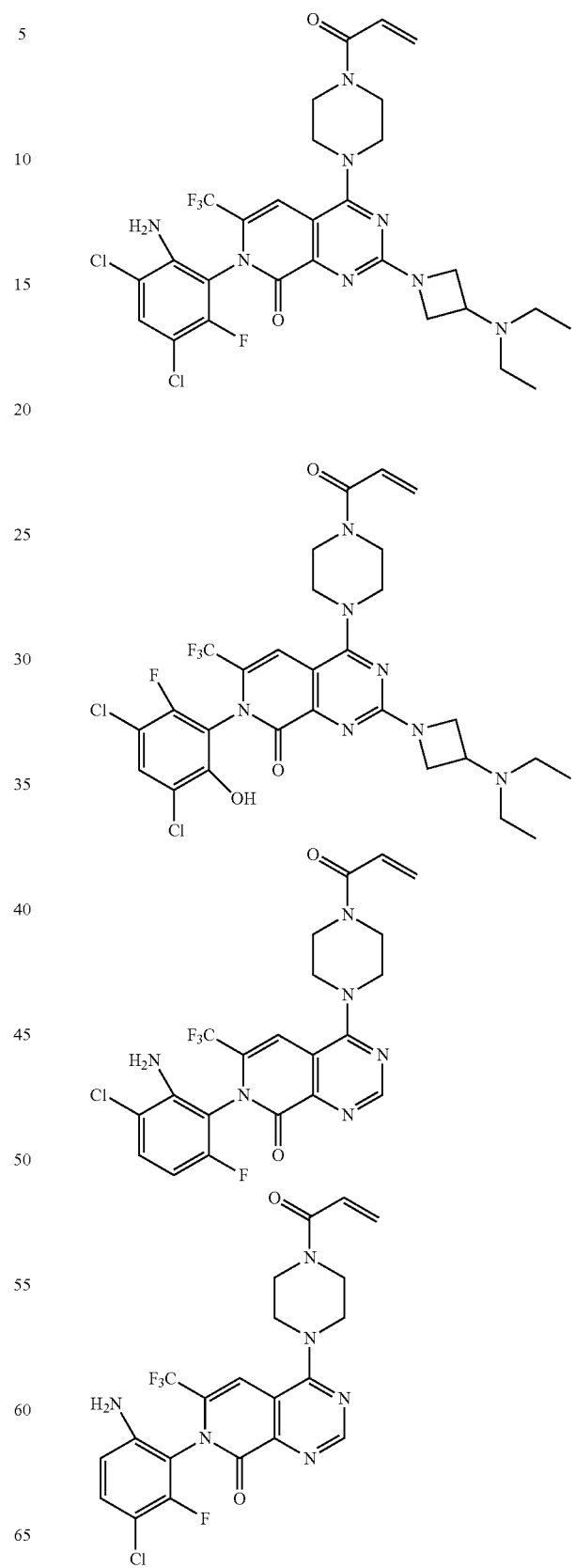

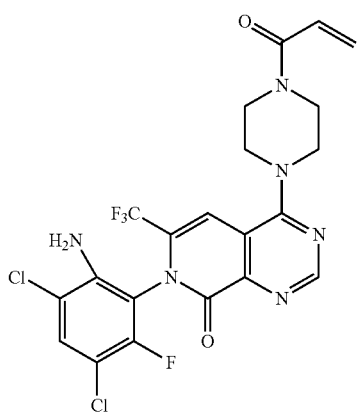
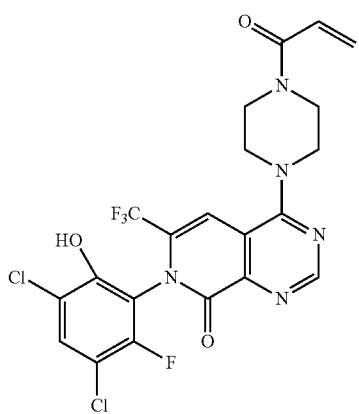
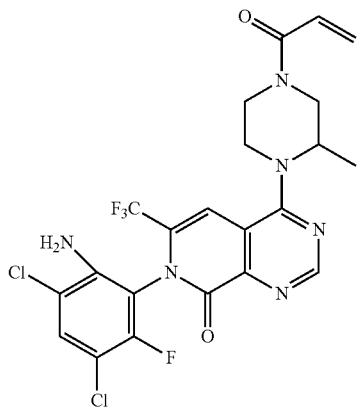
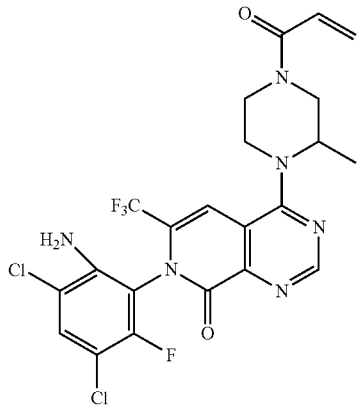
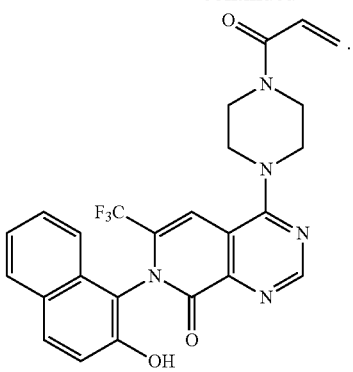
In some embodiments of the present invention, the above-mentioned compound, a pharmaceutically acceptable salt thereof or an isomer thereof is selected from
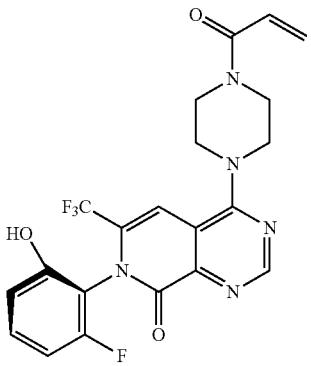
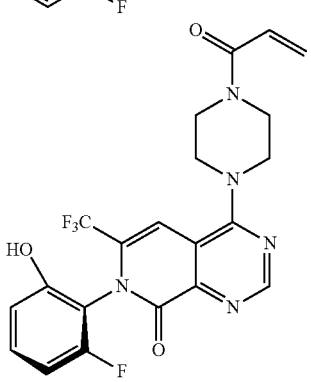
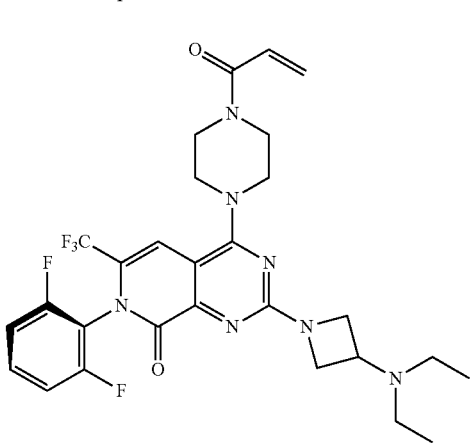

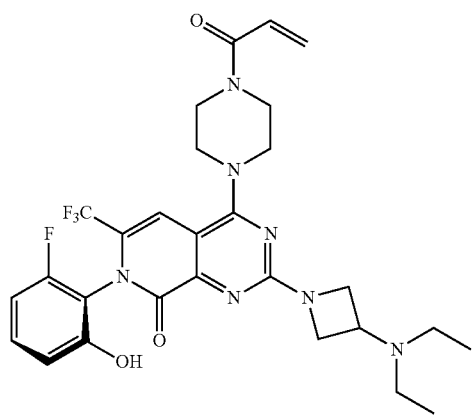
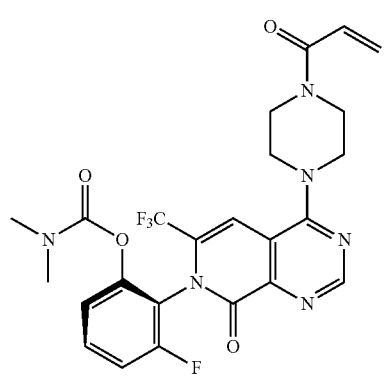
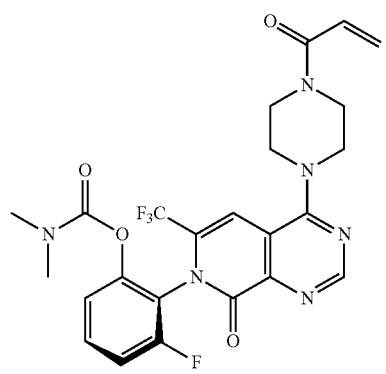
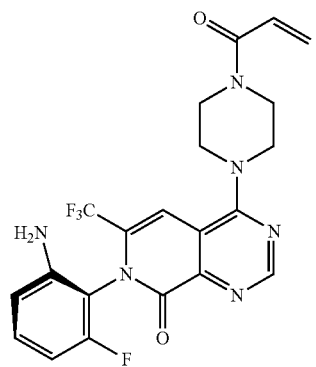
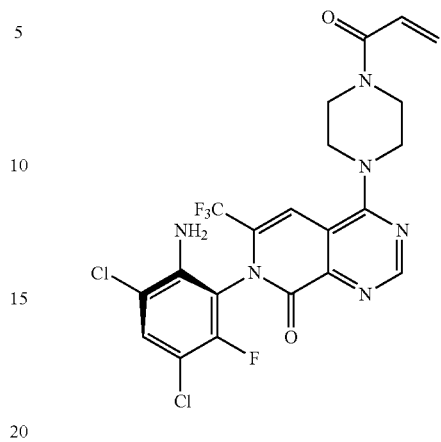
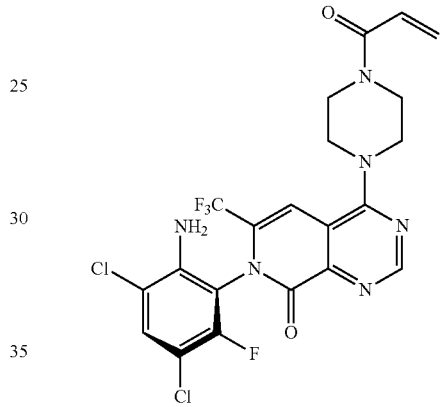
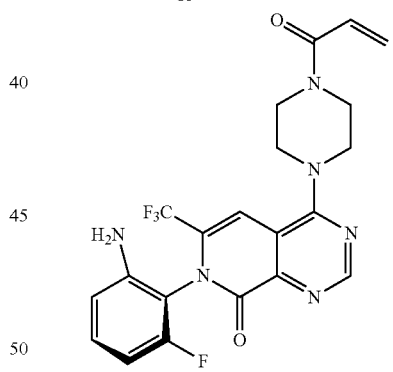
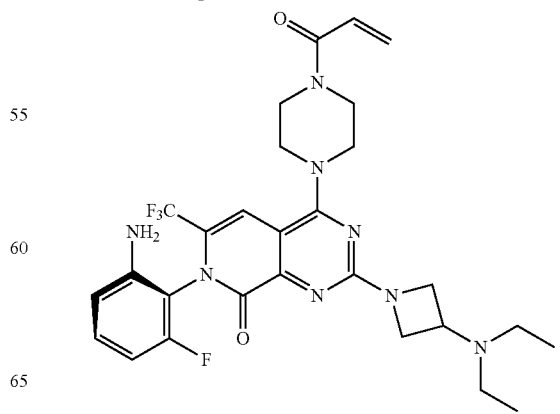

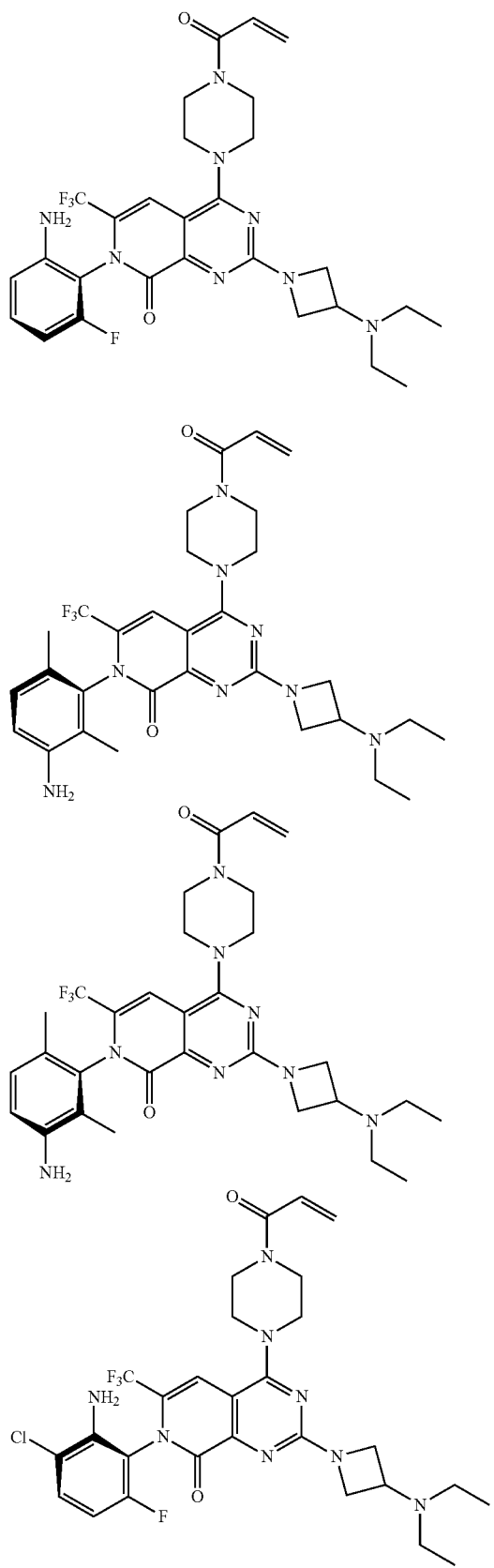
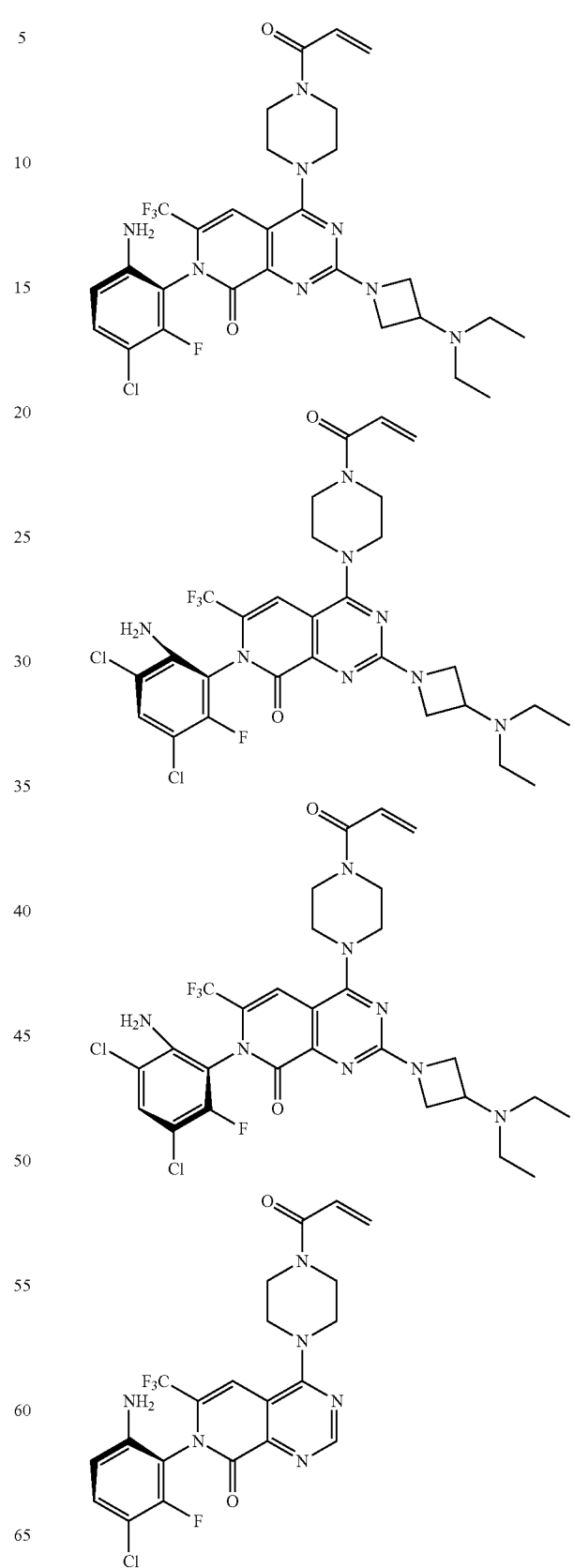

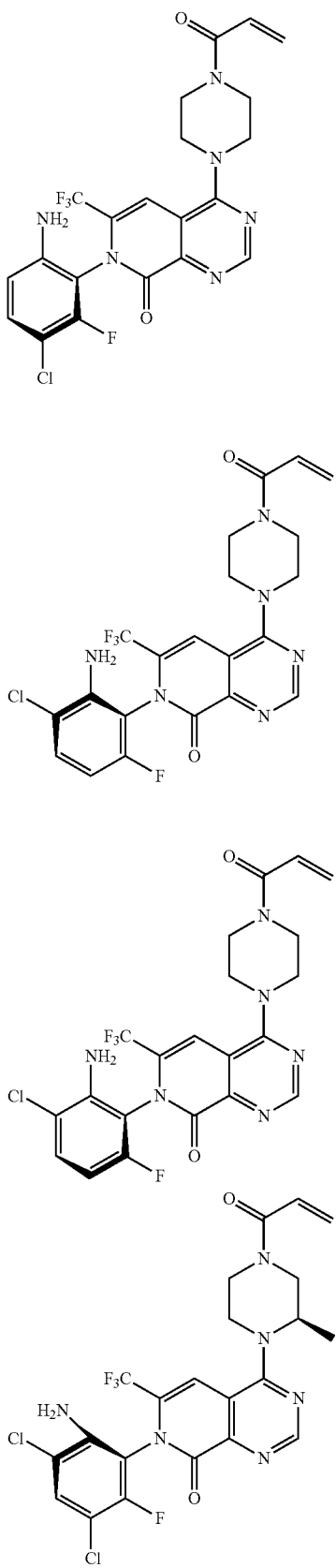
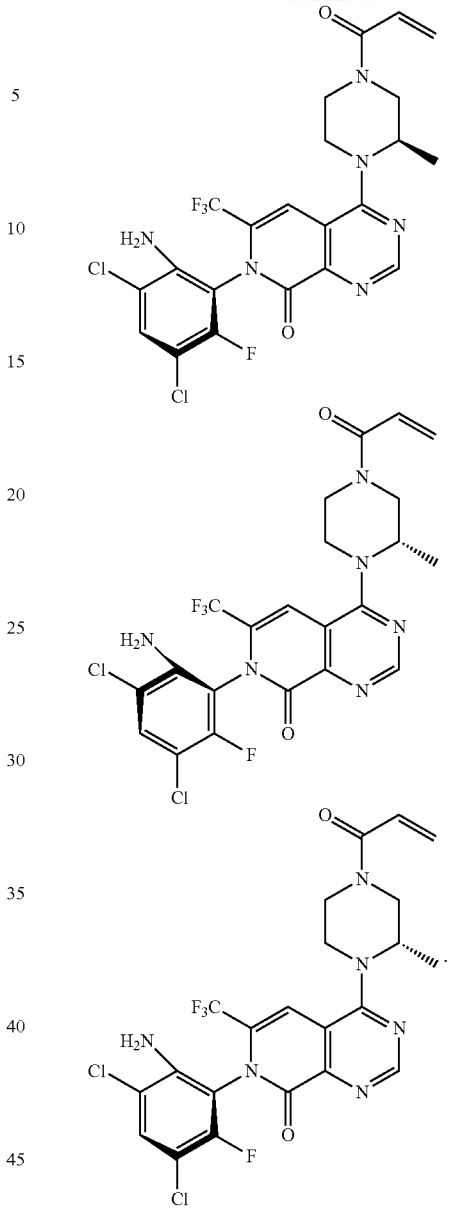

The present invention further provides the use of the above-mentioned compound, a pharmaceutically acceptable salt thereof or an isomer thereof in the preparation of a medicine for treating cancers.

In some embodiments of the present invention, the above-mentioned cancers include lung cancer, lymphoma, esophageal cancer, ovarian cancer, pancreatic cancer, rectal cancer, glioma, cervical cancer, urothelial cancer, gastric cancer, endometrial cancer, liver cancer, cholangiocarcinoma, breast cancer, colon cancer, leukemia and melanoma.

Other solutions of the present invention are generated by any combination of the above variables.

TECHNICAL EFFECTS

The compound of the present invention comprises a substituted pyridone-pyrimidine derivative, which has higher cellular anti-proliferative activity in terms of the KRAS G12C mutant protein, and has weaker activity against the wild type cell, exhibiting a good selectivity and showing that such compounds have better safety as a potential therapeutic agent. The core of the compound of the present invention has a pyridone-pyrimidine structure, a large polarity, and a high solubility. The substituent on the left aromatic ring has a significant effect on the activity, selectivity and pharmacokinetic properties of this compound. Such structure has high chemical stability and also shows high metabolic stability in vitro. In the rat pharmacokinetic evaluation experiment, the compounds of the present invention show higher exposure and better oral availability than the reference compound ARS-1620. The compound of the present invention exhibits a more significant tumor suppressive effect than the reference compound ARS-1620 in both subcutaneous xenograft tumor model of human non-small cell lung cancer NCI-H358 and subcutaneous xenograft tumor model of human pancreatic cancer x-MIA-PaCa2. In addition, because the pyridone-pyrimidine structure is rarely reported in the literature, it is difficult to perform substitution or derivatization on the structure. The present invention also provides a novel method for synthesizing the pyridone-pyrimidine structure, by which starting from different substituted amines, a series of derivatives can be synthesized by first constructing a pyridone structure and then constructing a pyrimidine ring. This method, an effective method for synthesizing such compounds, has not been reported in the literature.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof. The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present invention, which is prepared from the compound having specific substituents found in the present invention with relatively non-toxic acids or bases. When compounds of the present invention contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present invention contain relatively basic functional groups, acid addition salts can be obtained by contacting the neutral form of such compounds with a sufficient amount of acid, either in pure solution or a suitable inert solvent. Examples of pharmaceutically acceptable acid addition salts include inorganic acid salts, the inorganic acids including for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, and phosphorous acid or the like; and organic acid salts, the organic acids including for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid or the like; salts of amino acids (e.g., arginine); and salts of organic acids (e.g., glucuronic acid). Certain specific compounds of the present invention contain basic and acidic functional groups and thus can be converted to any base or acid addition salt.

The pharmaceutically acceptable salts of the present invention can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

In addition to salt forms, the compounds provided by the invention also exist in prodrug forms. The prodrugs of the compounds described herein are prone to chemical changes under physiological conditions, and thus are converted into the compounds of the present invention. In addition, prodrugs can be converted to the compounds of the invention by chemical or biochemical methods in the in vivo environment.

Certain compounds of the present invention may exist in unsolvated or solvated forms, including hydrated forms. Generally speaking, the solvated form is equivalent to the unsolvated form, and both are included in the scope of the present invention.

The compounds of the present invention may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present invention. Additional asymmetric carbon atoms may be present in a substituent such as an alkyl group. All these isomers and mixtures thereof are included in the scope of the present invention.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(D)" or "(+)" means dextrorotatory, "(L)" or "(−)" means levorotatory, and "(DL)" or "(±)" means racemic.

Unless otherwise stated, the wedge-shaped solid bond ( ◢ ) and the wedge-shaped dotted bond ( ⋰ ) represent the absolute configuration of a stereoscopic center; the straight solid bond ( ◢ ) and straight dotted bond ( ⋰ ) represent the relative configuration of a stereoscopic center; the wavy line ( ∼ ) represents the wedge-shaped solid bond ( ◢ ) or the wedge-shaped dotted bond ( ⋰ ) or the wavy line ( ∼ ) represents the straight solid bond ( ◢ ) and the straight dotted bond ( ⋰ ).

The compounds of the present invention may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include interconversion through recombination of some bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (9-isomers and D and L isomers can be prepared using chiral synthesis or chiral reagents or other conventional techniques. If a particular enantiomer of a compound of the present invention is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present invention may contain unnatural proportions of atomic isotopes at one or more of the atoms constituting the compound. For example, the compounds may be radiolabeled with radioactive isotopes, such as tritium ($^3$H), iodine-125 ($^{125}$I) or C-14 ($^{14}$C). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present invention, whether radioactive or not, are intended to be encompassed within the scope of the present invention.

"Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

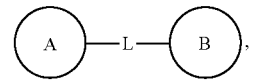, at this situation, -M-W— can connect ring A and ring B in the same direction as the reading order from left to right to form

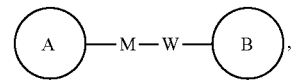, and can also connect ring A and ring B in the opposite direction as the reading order from left to right to form

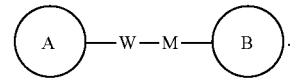.

Combinations of the linking groups, substituents, and/or variants thereof permissible only if such combinations result in stable compounds.

Unless otherwise specified, the term "hetero" means a heteroatom or a heteroatomic group (i.e., an atomic groups containing a heteroatom), including atoms other than carbon (C) and hydrogen (H) as well as atomic groups containing such heteroatoms, for example, oxygen (O), nitrogen (N), sulfur (S), silicon (Si), germanium (Ge), aluminum (Al), boron (B), —O—, —S—, —C(=O)O—, —C(=O)—, —C(=S)—, —S(=O), —S(=O)$_2$—, and optionally substituted (=O)N(H)—, —N(H)—, —C(=NH)—, —S(=O)$_2$N(H)— or —S(=O)N(H)—.

Unless otherwise specified, "ring" means substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, and also includes a spiro ring, a fused ring, a bridge ring and other bicyclic or polycyclic ring systems. The number of atoms in a ring is usually defined as the member number of the ring. For example, "5- to 7-membered ring" means that there are 5 to 7 atoms arranging in a circle. Unless otherwise specified, the ring optionally contains 1 to 3 heteroatoms. Therefore, "5- to 7-membered ring" includes, for example, phenyl, pyridyl, and piperidinyl; on the other hand, the term "5- to 7-membered heterocycloalkyl" includes pyridyl and piperidyl, but excludes phenyl. The term "ring" also includes ring systems containing at least one ring, each ring of which independently conforms to the above definition.

Unless otherwise specified, the term "alkyl" is used to represent a linear or branched saturated hydrocarbon group. In some embodiments, the alkyl is $C_{1-12}$ alkyl. In other embodiments, the alkyl is $C_{1-6}$ alkyl. In other embodiments, the alkyl is $C_{1-3}$ alkyl. It may be mono-substituted (such as —CH$_2$F) or poly-substituted (such as —CF$_3$), and may be monovalent (such as methyl), divalent (such as methylene) or polyvalent (such as methine). Examples of alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, "alkenyl" is used to represent a linear or branched hydrocarbon group containing one or more carbon-carbon double bonds, which may be located at any position of the group. In some embodiments, the alkenyl is $C_{2-8}$ alkenyl. In other embodiments, the alkenyl is $C_{2-6}$ alkenyl. In other embodiments, the alkenyl is $C_{2-4}$ alkenyl. It may be mono-substituted or poly-substituted, and may be monovalent, divalent or polyvalent. Examples of alkenyl include, but are not limited to, vinyl, propenyl, butenyl, pentenyl, hexenyl, butadienyl, piperylene and hexadienyl.

Unless otherwise specified, the term "heteroalkyl" by itself or in combination with another term means a stable linear or branched alkyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl. In other embodiments, the heteroalkyl is $C_{1-3}$ heteroalkyl. Heteroatom or heteroatomic group may be located at any internal position of heteroalkyl, including the connection positions of the alkyl to the remainder of the molecule. However, the terms "alkoxy", "alkylamino" and "alkylthio" (or thioalkoxy) are used in their conventional sense and refer to those alkyl groups attached to the remainder of the molecule via an oxygen atom, an amino group, or a sulfur atom, respectively. Examples of heteroalkyl include but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$, —CH=CH—O—CH$_3$, —CH$_2$—CH=N—OCH$_3$ and —CH=CH—N(CH$_3$)—CH$_3$. Up to two heteroatoms can be consecutive, such as —CH$_2$—NH—OCH$_3$.

Unless otherwise specified, the term "heteroalkenyl" by itself or in combination with another term means a stable linear or branched alkenyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkenyl is $C_{2-6}$ heteroalkenyl. In other embodiments, the heteroalkyl is $C_{2-4}$ heteroalkenyl. Heteroatom or heteroatomic group may be located at any internal position of heteroalkenyl, including the connection positions of the alkenyl to the remainder of the molecule. However, the terms "alkenyloxy", "alkenylamino" and "alkenylthio" are used in their conventional sense and refer to those alkenyl groups attached to the remainder of the molecule via an oxygen atom, an amino group, or a sulfur atom, respectively. Examples of heteroalkenyl include but are not limited to, —O—CH=CH$_2$, —O—CH=CHCH$_3$, —O—CH=C(CH$_3$)$_2$, —CH=CH—O—CH$_3$, —O—CH=CHCH$_2$CH$_3$, —CH$_2$—CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$. Up to two heteroatoms may be consecutive, for example, —CH=CH—NH—OCH$_3$.

Unless otherwise specified, the term "heteroalkynyl" by itself or in combination with another term means a stable linear or branched alkynyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkynyl is $C_{2-6}$ heteroalkynyl. In other embodiments, the heteroalkyl is $C_{2-4}$ heteroalkynyl. Heteroatom or heteroatomic group may be located at any internal position of heteroalkynyl, including the connection positions of the alkynyl to the remainder of the molecule. However, the terms "alkynyloxy", "alkynylamino" and "alkynylthio" are used in their conventional sense and refer to those alkynyl groups attached to the remainder of the molecule via an oxygen atom, an amino group, or a sulfur atom, respectively. Examples of heteroalkynyl include but are not limited to,

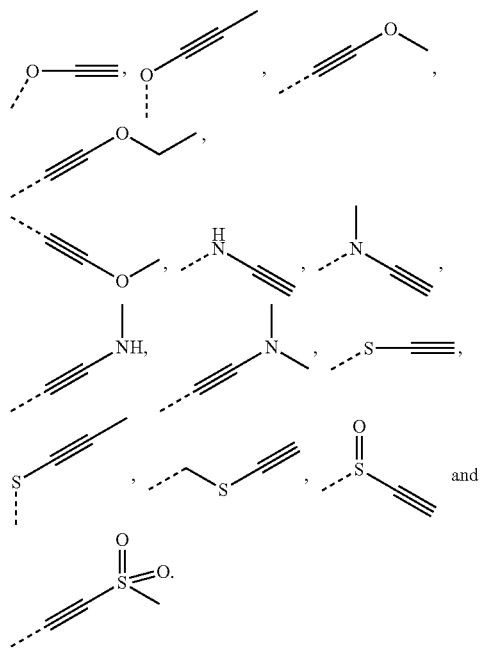

Up to two heteroatoms may be consecutive, for example,

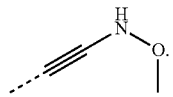

Unless otherwise specified, "cycloalkyl" includes any stable cyclic alkyl including a monocyclic, bicyclic or tricyclic ring system, wherein the bicyclic and tricyclic ring systems include a spiro ring, a fused ring, and a bridge ring. In some embodiments, the cycloalkyl is $C_{3-8}$ cycloalkyl. In other embodiments, the cycloalkyl is $C_{3-6}$ cycloalkyl. In other embodiments, the cycloalkyl is $C_{5-6}$ cycloalkyl. It may be mono-substituted or poly-substituted, and may be monovalent, divalent or polyvalent. Examples of the cycloalkyl include, but are not limited to, cyclopropyl, cyclobutyl, cyclopentyl, cyclohexyl, cycloheptyl, norbornyl, [2.2.2] bicyclooctane, and [4.4.0] bicyclodecane.

Unless otherwise specified, "cycloalkenyl" includes any stable cyclic alkenyl containing one or more unsaturated carbon-carbon double bonds at any position of the group, which includes a monocyclic, bicyclic or tricyclic system, wherein the bicyclic and tricyclic ring systems include a spiro ring, a fused ring, and a bridge ring, but any ring in the systems is non-aromatic. In some embodiments, the cycloalkenyl is $C_{3-8}$ cycloalkenyl. In other embodiments, the cycloalkenyl is $C_{3-6}$ cycloalkenyl. In other embodiments, the cycloalkenyl is $C_{5-6}$ cycloalkenyl. It may be mono-substituted or poly-substituted, and may be monovalent, divalent or polyvalent. Examples of the cycloalkenyl include, but are not limited to, cyclopentenyl and cyclohexenyl.

Unless otherwise specified, "cycloalkynyl" includes any stable cyclic alkynyl containing one or more carbon-carbon triple bonds at any position of the group, which includes a monocyclic, bicyclic or tricyclic ring system, wherein the bicyclic and tricyclic ring systems include a spiro ring, a fused ring, and a bridge ring. It may be mono-substituted or poly-substituted, and may be monovalent, divalent or polyvalent.

Unless otherwise specified, the term "heterocycloalkyl" by itself or in combination with other terms respectively represents a cyclized "heteroalkyl" group, which includes a monocyclic, bicyclic or tricyclic ring system, wherein the bicyclic and tricyclic ring systems include a spiro ring, a fused ring, and a bridge ring. In addition, in terms of the "heterocycloalkyl", the heteroatom may occupy the connection position of the heterocyclic alkyl to the remainder of the molecule. In some embodiments, the heterocycloalkyl is 4- to 6-membered heterocycloalkyl. In other embodiments, the heterocycloalkyl is 5- to 6-membered heterocycloalkyl. Examples of heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl), tetrahydrofuranyl (including tetrahydrofuran-2-yl), tetrahydropyranyl, piperidinyl (including 1-piperidinyl, 2-piperidinyl and 3-piperidinyl), piperazinyl (including 1-piperazinyl and 2-piperazinyl), morpholinyl (including 3-morpholinyl and 4-morpholinyl), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "heterocycloalkenyl" by itself or in combination with other terms respectively represents a cyclized "heteroalkenyl" group, which includes a monocyclic, bicyclic and tricyclic ring system, wherein the bicyclic and tricyclic ring systems include a spiro ring, a fused ring, and a bridge ring, but any ring in the systems is non-aromatic. In addition, in terms of the "heterocycloalkenyl", the heteroatom may occupy the connection position of the heterocycloalkenyl to the remainder of the molecule. In some embodiments, the heterocycloalkenyl is 4- to 6-membered heterocycloalkenyl. In other embodiments, the heterocycloalkenyl is 5- to 6-membered heterocycloalkenyl. Examples of heterocycloalkenyl groups include but are not limited to,

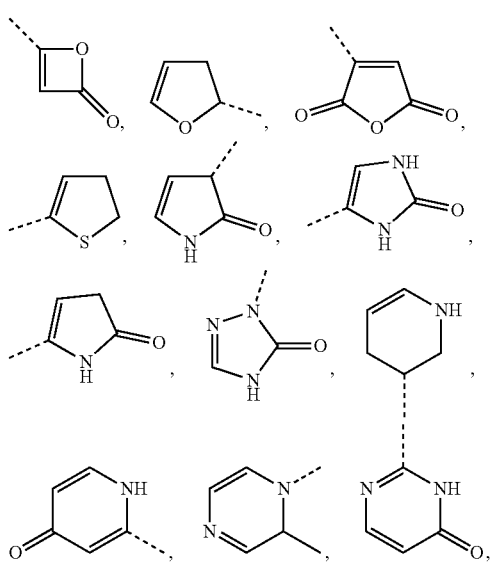

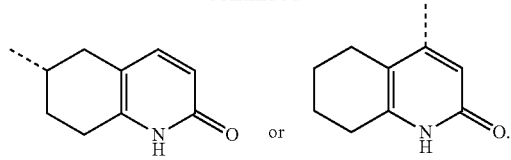

Unless otherwise specified, the term "heterocycloalkynyl" by itself or in combination with other terms respectively represents a cyclized "heteroalkynyl" group, which includes a monocyclic, bicyclic and tricyclic ring system, wherein the bicyclic and tricyclic ring systems include a spiro ring, a fused ring, and a bridge ring. In addition, in terms of the "heterocycloalkynyl", the heteroatom may occupy the connection position of the heterocycloalkynyl with the remainder of the molecule. In some embodiments, the heterocycloalkynyl is 4- to 6-membered heterocycloalkynyl. In other embodiments, the heterocycloalkynyl is 5- to 6-membered heterocycloalkynyl. Unless otherwise specified, the term "halo" or "halogen" by itself or as part of another substituent means a fluorine, chlorine, bromine or iodine atom. In addition, the term "haloalkyl" is intended to include monohaloalkyl and polyhaloalkyl. For example, the term "halo($C_1$-$C_4$) alkyl" is intended to include, but is not limited to, trifluoromethyl, 2,2,2-trifluoroethyl, 4-chlorobutyl and 3-bromopropyl. Unless otherwise specified, examples of haloalkyl include, but are not limited to: trifluoromethyl, trichloromethyl, pentafluoroethyl and pentachloroethyl.

"Alkoxy" represents the above alkyl having a specific number of carbon atoms connected via an oxygen bridge. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, the terms "aromatic ring" and "aryl" in the present invention can be used interchangeably. The term "aromatic ring" or "aryl" means a polyunsaturated carbocyclic system, which may be a monocyclic, bicyclic or tricyclic system, in which at least one ring is aromatic, and the rings in the bicyclic and polycyclic ring systems are fused together. It may be mono-substituted or poly-substituted, and may be monovalent, divalent, or polyvalent. In some embodiments, the aryl is $C_{6-12}$ aryl. In other embodiments, the aryl is $C_{6-10}$ aryl. Examples of aryl include, but are not limited to, phenyl, naphthyl (including 1-naphthyl and 2-naphthyl). The substituent of any one of the above aryl ring systems is selected from the acceptable substituents described in the present invention.

Unless otherwise specified, the terms "heteroaryl ring" and "heteroaryl" of the present invention can be used interchangeably. The term "heteroaryl" refers to aryl (or aromatic ring) containing 1, 2, 3 or 4 heteroatoms independently selected from B, N, O and S, which may be a monocyclic, bicyclic or tricyclic ring system, wherein the nitrogen atom may be substituted or unsubstituted (i.e., N or NR, wherein R is H or other substituents already defined herein), and optionally quaternized, and the nitrogen and sulfur heteroatoms may be optionally oxidized (i.e., NO and $S(O)_p$, wherein p is 1 or 2). Heteroaryl can be connected to the remainder of the molecule via a heteroatom. In some embodiments, the heteroaryl is a 5- to 10-membered heteroaryl. In other embodiments, the heteroaryl is a 5- to 6-membered heteroaryl. Examples of the heteroaryl include, but are not limited to, pyrrolyl (including N-pyrrolyl, 2-pyrrolyl and 3-pyrrolyl), pyrazolyl (including 2-pyrazolyl and 3-pyrazolyl), imidazolyl (including N-imidazolyl, 2-imidazolyl, 4-imidazolyl and 5-imidazolyl), oxazolyl (including 2-oxazolyl, 4-oxazolyl and 5-oxazolyl), triazolyl (1H-1,2,3-triazolyl, 2H-1,2,3-triazolyl, 1H-1,2,4-triazolyl and 4H-1,2,4-triazolyl), tetrazolyl, isoxazolyl (3-isoxazolyl, 4-isoxazolyl, and 5-isoxazolyl), thiazolyl (including 2-thiazolyl, 4-thiazole and 5-thiazolyl), furyl (including 2-furanyl and 3-furanyl), thienyl (including 2-thienyl and 3-thienyl), pyridyl (including 2-pyridyl, 3-pyridyl and 4-pyridyl), pyrazinyl, pyrimidinyl (including 2-pyrimidinyl and 4-pyrimidinyl), benzothiazolyl (including 5-benzothiazolyl), purinyl, benzimidazolyl (including 2-benzimidazolyl), indolyl (including 5-indolyl), isoquinolinyl (including 1-isoquinolinyl and 5-isoquinolinyl), quinoxalinyl (including 2-quinoxalinyl and 5-quinoxalinyl), quinolinyl (including 3-quinolinyl and 6-quinolinyl), pyrazinyl, purinyl, and benzoxazolyl. The substituent of any one of the above heteroaryl ring systems is selected from the acceptable substituents described in the present invention.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$; Similarly, n-membered to n+m-membered means that the number of atoms in the ring is n to n+m, for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring, and a 12-membered ring, and also includes any range from n to n+m, for example, a 3- to 12-membered ring includes a 3- to 6-membered ring, a 3- to 9-membered ring, a 5- to 6-membered ring, a 5- to 7-membered ring, a 6- to 7-membered ring, a 6- to 8-membered ring, and a 6- to 10-membered ring.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxy protecting group" or "mercapto protecting group". The term "amino protecting group" refers to a protecting group suitable for preventing side reactions occur at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TB S). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TB S).

In the test samples of the examples of the present invention, the formate of a compound is obtained by separation and purification of the compound by chromatography under the formic acid system (phase A: $H_2O$+0.225% formic acid, phase B: acetonitrile).

The compounds of the present invention can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present invention.

The solvents used in the present invention are commercially available.

The present invention uses the following abbreviations: DCM represents dichloromethane; DMF represents N,N-dimethylformamide; DMSO represents dimethyl sulfoxide; NMP represents N-methylpyrrolidone; Boc represents tert-butoxycarbonyl, which is an amine protecting group; THF represents tetrahydrofuran; NBS represents N-bromosuccinimide; TEA represents triethylamine; DIPEA represents N,N-diisopropylethylamine; NaOH represents sodium hydroxide; DBU represents 1,8-diazabicyclo-undec-7-ene; TFE represents trifluoroethanol; TFA represents trifluoroacetic acid; HOBt represents 1-hydroxybenzotriazole; EDCI.HCl represents 1-ethyl-(3-dimethylaminopropyl)carbodiimide hydrochloride; NCS represents N-chlorosuccinimide; $EDTA-K_2$ represents dipotassium ethylene diamine tetraacetate; PEG400 represents polyethylene glycol 400; PO represents oral administration; IV represents intravenous administration.

Compounds are named by hand or ChemDraw® software, and commercially available compounds are named by the supplier catalog names.

DETAILED DESCRIPTION OF THE PREFERRED EMBODIMENT

The present invention will be described in detail with the following examples, but not imply any adverse limitation to the present invention. The compounds of the present invention can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present invention. Various changes and improvements to the specific embodiments of the present invention would be obvious to a person skilled in the art without departing from the spirit and scope of the present invention.

Scheme A

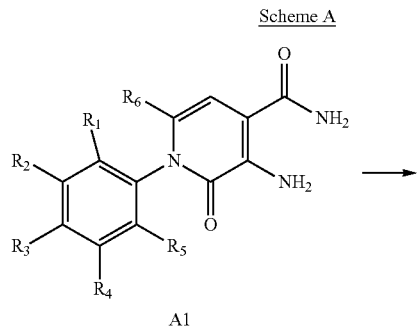

A1

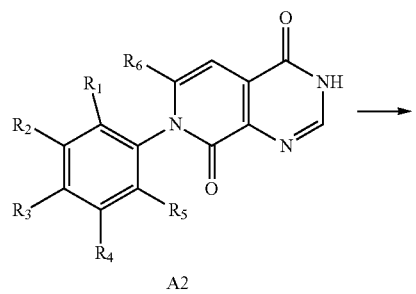

A2

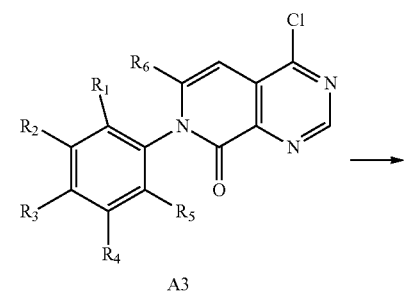

A3

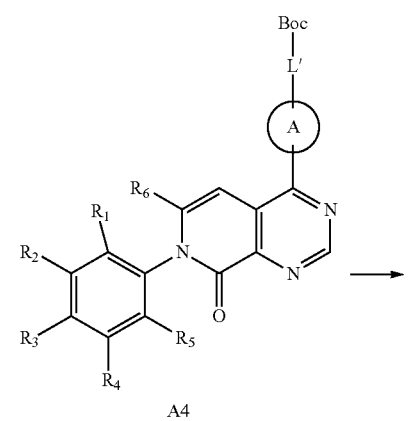

A4

A5

-continued

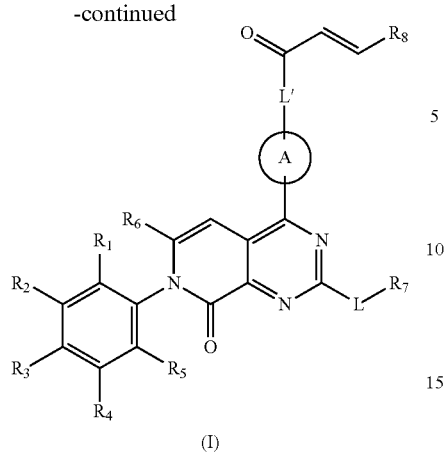

(I)

When L-$R_7$ is H and $R_1$, $R_2$, $R_3$, $R_4$ and $R_5$ are not OH, the reaction proceeds according to Scheme A.

Compound A1 and a suitable reagent (such as triethyl orthoformate and sulfuric acid/formic acid) are subjected to a ring closure reaction to obtain compound A2. The compound A2 is reacted with a suitable chlorinated reagent (e.g., phosphorus oxychloride) to obtain compound A3. The compound A3 is reacted with a Boc-protected amine under the action of a suitable base (such as TEA or DIPEA) to obtain compound A4. The compound A4 is subjected to a deprotection reaction under acidic conditions to obtain compound A5. If $R_1$, $R_2$, $R_3$, $R_4$ and $R_5$ in the compound A5 are not $NH_2$, the compound A5 is reacted with a suitable acylating reagent (e.g., alkenyl chloride) in the presence of a suitable base (e.g., TEA) to obtain compound (I); if any of $R_1$, $R_2$, $R_3$, $R_4$ and $R_5$ in the compound A5 is $NH_2$, the compound A5 is reacted with a suitable acylating reagent (e.g., alkenyl chloride) in the presence of a suitable base (e.g., TEA), and then the intermediate compound obtained is subjected to a reduction reaction on the nitro group at the corresponding position to obtain compound (I).

Scheme B

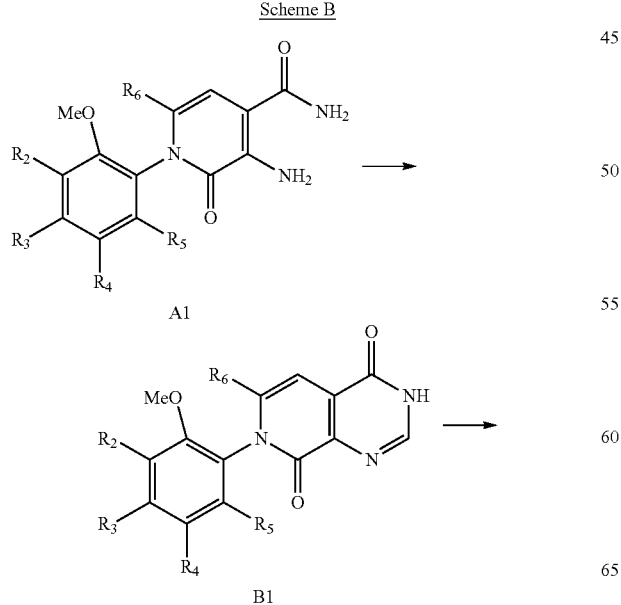

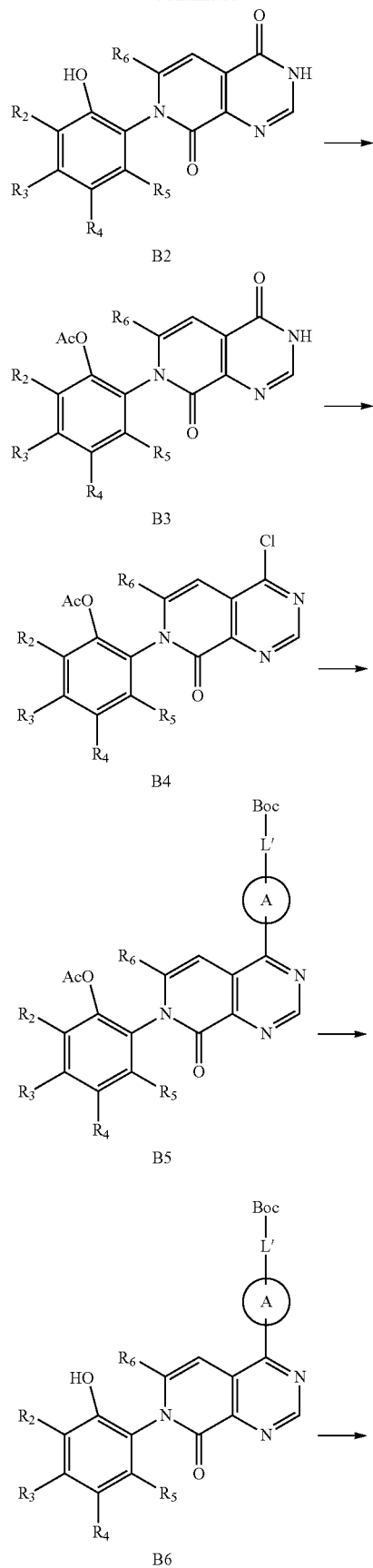

-continued

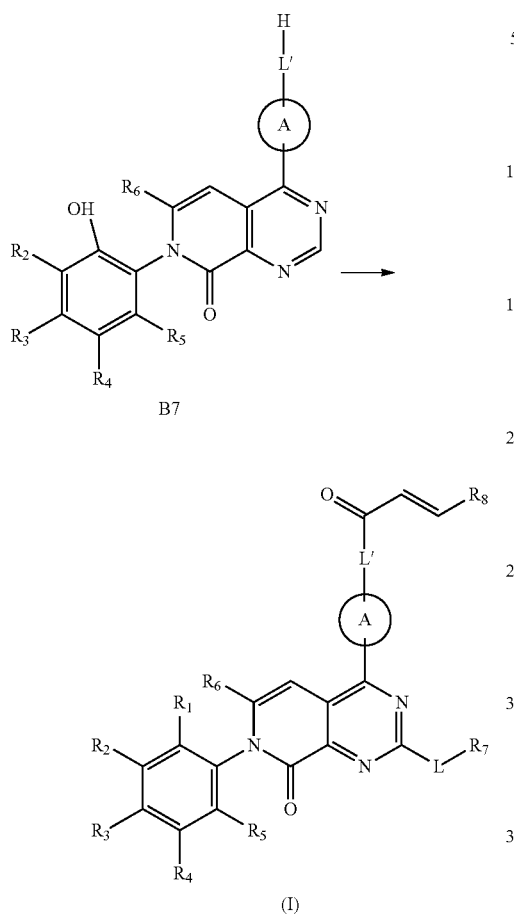

B7

(I)

When L-R$_7$ is H and any of R$_1$, R$_2$, R$_3$, R$_4$ and R$_5$ is OH (for example, R$_1$ is OH), the reaction proceeds according to Scheme B.

Compound A1 and a suitable reagent (such as triethyl orthoformate and sulfuric acid/formic acid) are subjected to a ring closure reaction to obtain compound B1, and then the compound B1 is treated with pyridine hydrochloride to obtain a demethylated product B2. The compound B2 is reacted with acetic anhydride in the presence of a suitable base (e.g., pyridine) to obtain compound B3. The compound B3 is reacted with a suitable chlorinated reagent (e.g., phosphorus oxychloride) to obtain compound B4, which is then reacted with a Boc-protected amine in the presence of a suitable base (e.g., DIPEA) to obtain compound B5. The compound B5 is subjected to deacetylation and deprotection of Boc to obtain compound B6 and compound B7, respectively. If R$_1$, R$_2$, R$_3$, R$_4$ and R$_5$ in the compound B7 are not NH$_2$, the compound B7 is reacted with a suitable acylating reagent (e.g., alkenyl chloride) in the presence of a suitable base (e.g., TEA) to obtain compound (I); if any of R$_1$, R$_2$, R$_3$, R$_4$ and R$_5$ in the compound B7 is NH$_2$, the compound B7 is reacted with a suitable acylating reagent (e.g., alkenyl chloride) in the presence of a suitable base (e.g., TEA), and then the intermediate compound obtained is subjected to a reduction reaction on the nitro group at the corresponding position to obtain compound (I).

Scheme C

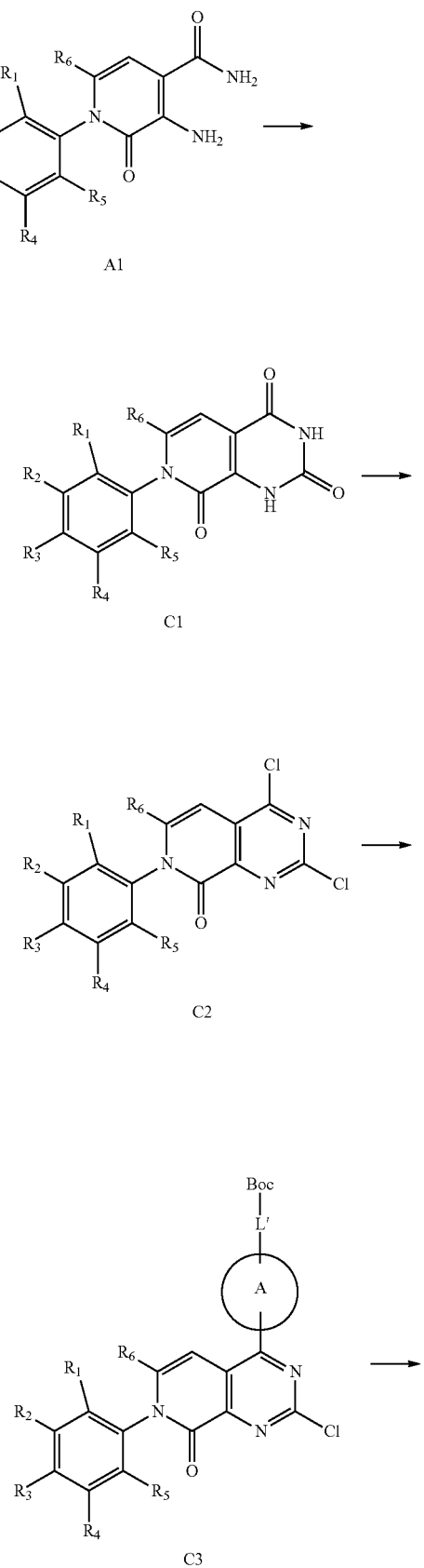

A1

C1

C2

C3

-continued

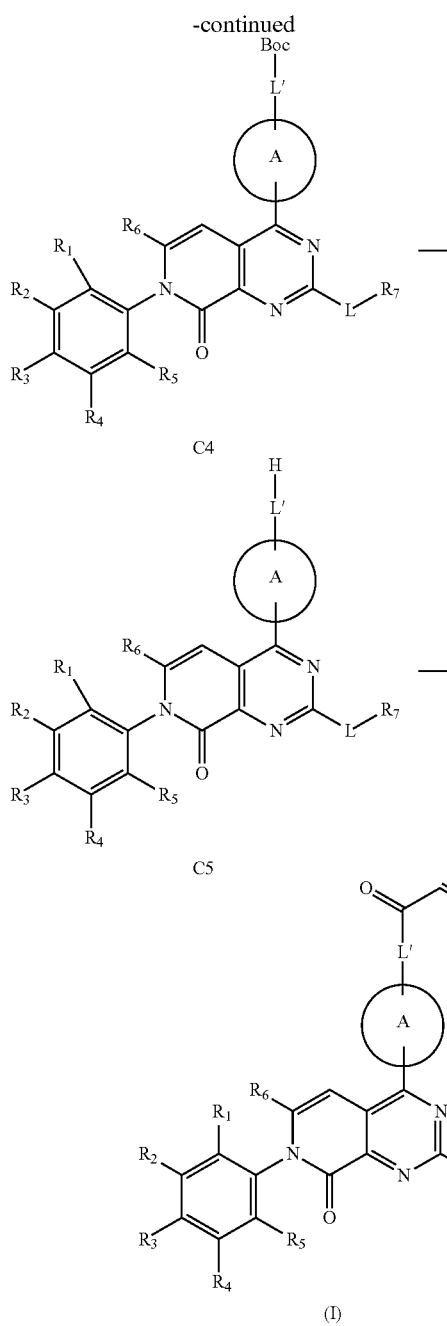

C4

C5

(I)

When L-R₇ is not H and $R_1$, $R_2$, $R_3$, $R_4$ and $R_5$ are not OH, the reaction proceeds according to Scheme C.

Compound A1 and a suitable reagent (such as urea, or plasma liquid [HDBU⁺][TFE⁻] prepared with DBU and TFE, and carbon dioxide gas) are subjected to a ring closure reaction to obtain compound C1. The compound C1 is reacted with a suitable chlorinated reagent (e.g., phosphorus oxychloride) to obtain a dichlorinated product C2, which is then reacted with a Boc-protected amine in the presence of a suitable base (e.g., DIPEA) to obtain compound C3. The compound C3 is reacted with a nucleophilic reagent (such as substituted amino, alcohol or potassium cyanide) in the presence of a suitable base (such as DIPEA or potassium fluoride) to obtain compound C4. The compound C4 is subjected to a deprotection reaction to obtain compound C5. If $R_1$, $R_2$, $R_3$, $R_4$ and $R_5$ in the compound C5 are not $NH_2$, the compound C5 is reacted with a suitable acylating reagent (e.g., alkenyl chloride) in the presence of a suitable base (e.g., TEA) to obtain compound (I); if any of $R_1$, $R_2$, $R_3$, $R_4$ and $R_5$ in the compound C5 is $NH_2$, the compound C5 is reacted with a suitable acylating reagent (e.g., alkenyl chloride) in the presence of a suitable base (e.g., TEA), and then the intermediate compound obtained is subjected to a reduction reaction on the nitro group at the corresponding position to obtain compound (I).

Scheme D

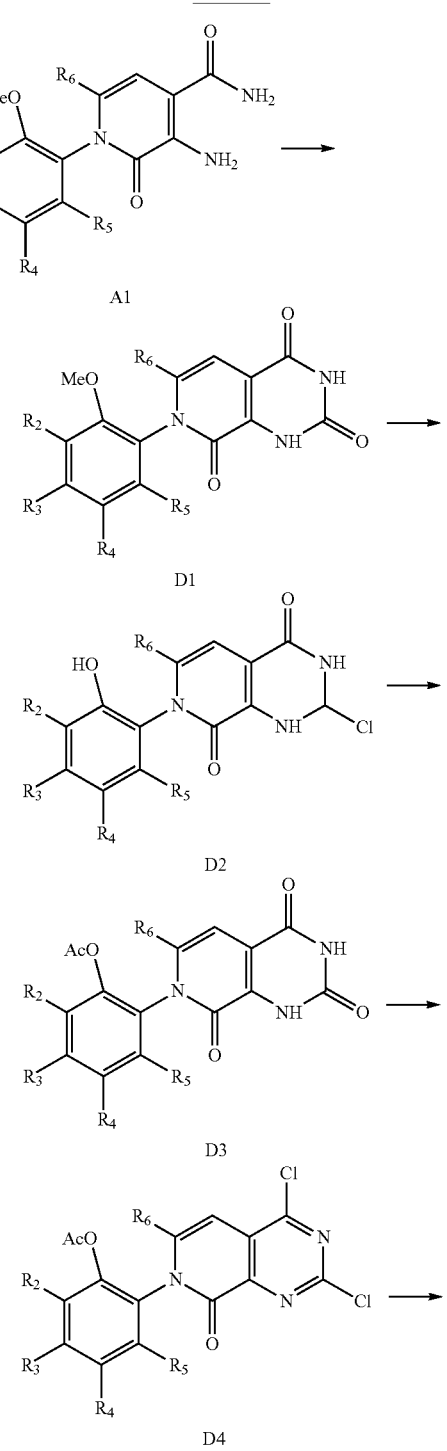

A1

D1

D2

D3

D4

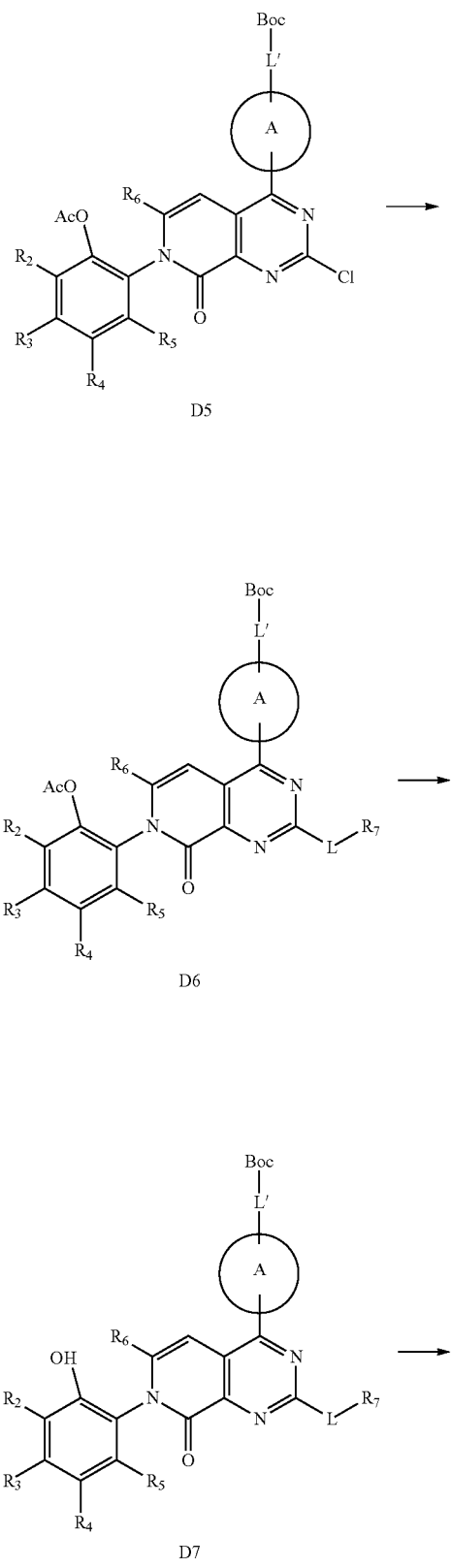

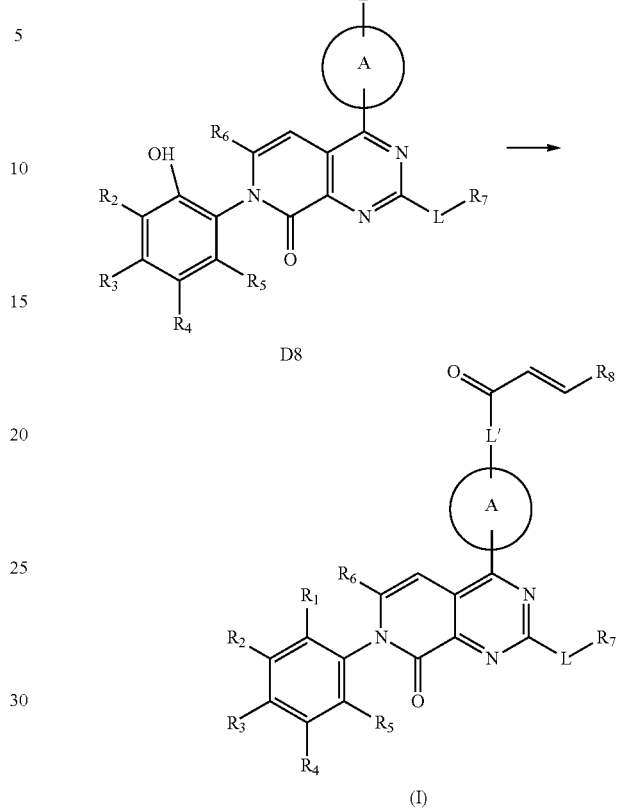

When L-R₇ is not H and any of $R_1$, $R_2$, $R_3$, $R_4$ and $R_5$ is OH (for example, $R_1$ is OH), the reaction proceeds according to Scheme D.

Compound A1 and a suitable reagent (such as urea, or plasma liquid [HDBU⁺][TFE⁻] prepared with DBU and TFE, and carbon dioxide gas) are subjected to a ring closure reaction to obtain compound D1, and then the compound D1 is treated with pyridine hydrochloride to obtain a demethylated product D2. The compound D2 is reacted with acetic anhydride in the presence of a suitable base (e.g., pyridine) to obtain compound D3. The compound D3 is reacted with a suitable chlorinated reagent (e.g., phosphorus oxychloride) to obtain compound D4, which is then reacted with a Boc-protected amine in the presence of a suitable base (e.g., DIPEA) to obtain compound D5. The compound D5 is reacted with a nucleophilic reagent (such as substituted amino, alcohol or potassium cyanide) in the presence of a suitable base (such as DIPEA or potassium fluoride) to obtain compound D6. The compound D6 is subjected to deacetylation and deprotection of Boc to obtain compound D7 and compound D8, respectively. If $R_1$, $R_2$, $R_3$, $R_4$ and $R_5$ in the compound D8 are not $NH_2$, the compound D8 is reacted with a suitable acylating reagent (e.g., alkenyl chloride) in the presence of a suitable base (e.g., TEA) to obtain compound (I); if any of $R_1$, $R_2$, $R_3$, $R_4$ and $R_5$ in the compound D8 is $NH_2$, the compound D8 is reacted with a suitable acylating reagent (e.g., alkenyl chloride) in the presence of a suitable base (e.g., TEA), and then the intermediate compound obtained is subjected to a reduction reaction on the nitro group at the corresponding position to obtain compound (I).

Scheme E

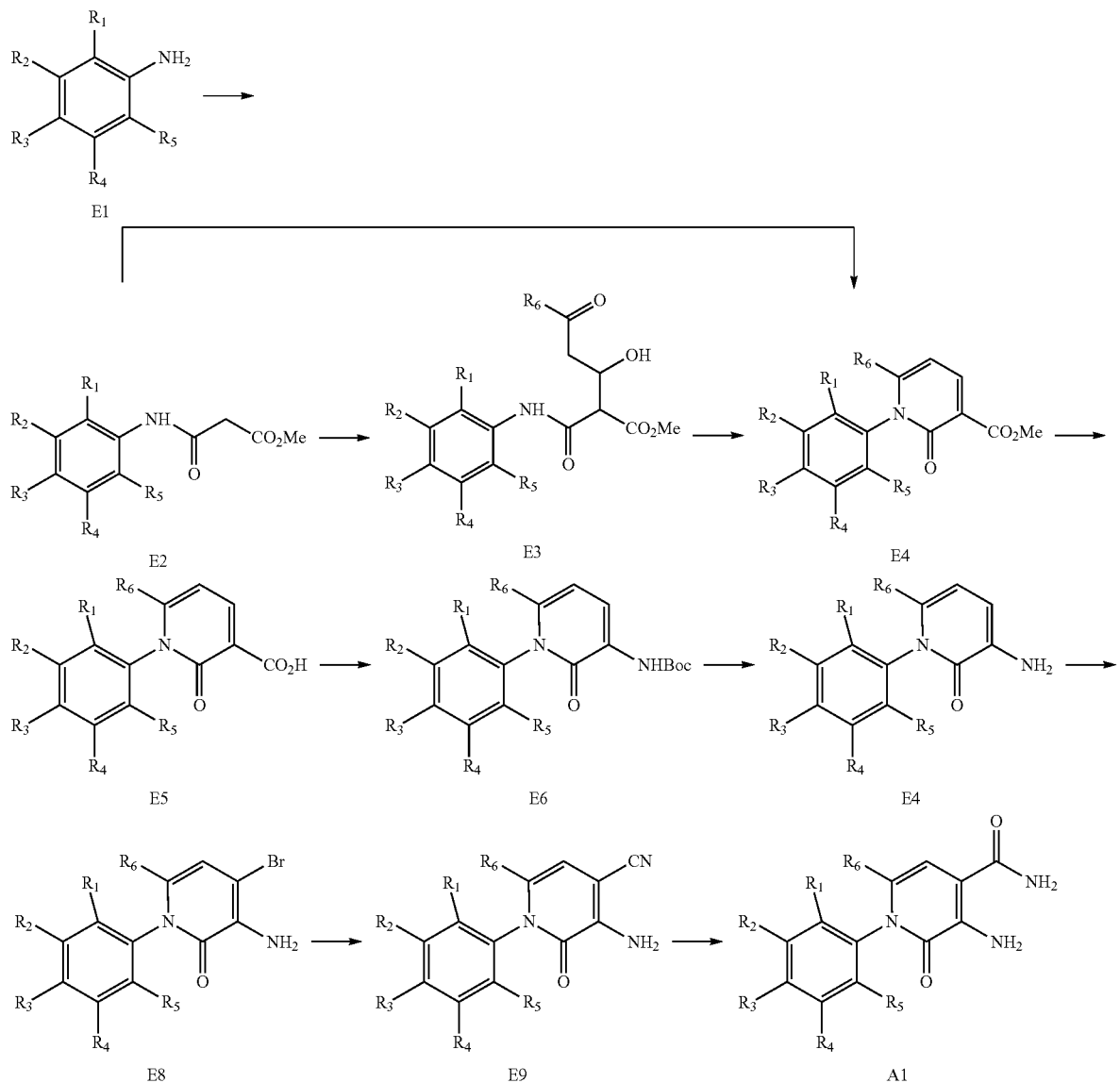

In Scheme E above, compound E1 is reacted with a suitable acyl chloride (e.g., methyl 3-chloro-3-oxopropionate) to obtain compound E2. Two methods can be used for the synthesis of compound E4: ① the compound E2 is condensed with a suitable enether (e.g., (E)-4-ethoxy-1,1,1-trifluoro-3-buten-2-one) to obtain compound E3. The compound E3 is heated to react under the action of a dehydrating agent like p-toluenesulfonic acid, and then the dehydrated compound is subjected to a ring closure reaction to obtain compound A4; ② the compound E2 is subjected to a direct ring closure reaction in the presence of a strong base (e.g., sodium methoxide) to obtain compound E4. The compound E4 is hydrolyzed to obtain compound E5, which is then subjected to a Curtius rearrangement reaction to obtain a Boc-protected amino compound E6. The compound E6 is deprotected to obtain compound E7, and then the compound E7 is brominated with a suitable brominating reagent (e.g., NBS) to obtain compound E8. The compound E8 is reacted with a suitable cyanation reagent (e.g., cuprous cyanide) to obtain compound E9. The compound E9 is hydrolyzed to obtain compound A1.

Example 1

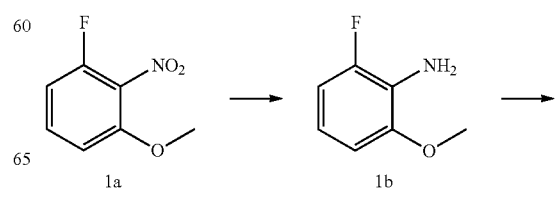

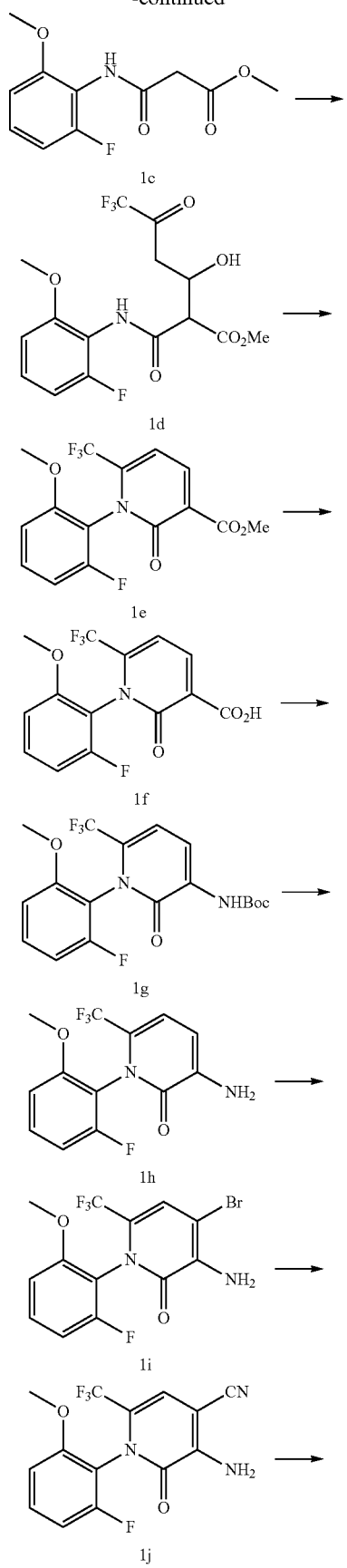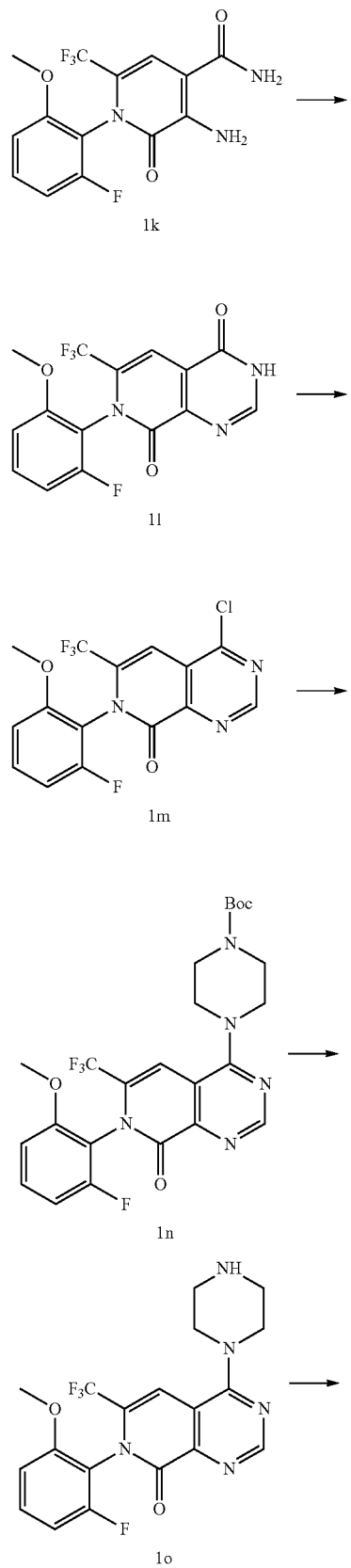

-continued

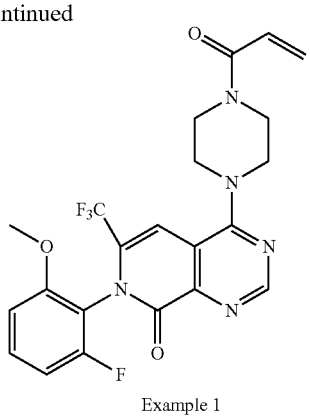

Example 1

First Step:

Compound 1a (4.8 g, 28.34 mmol) was dissolved in ethyl acetate (10 mL), and palladium/carbon (500 mg, 10%) was added thereto under the protection of nitrogen. The reaction solution was subjected to replacement with hydrogen several times, and then stirred under a hydrogen balloon at 15° C. for 6 hours. The reaction mixture was filtered, and the filtrate was concentrated to obtain compound 1b. $^1$H NMR (400 MHz, CDCl$_3$) δ 6.71-6.62 (m, 3H), 3.88 (s, 3H), 3.76 (brs, 2H).

Second Step:

The compound 1b (4.00 g, 28.34 mmol) and TEA (5.74 g, 56.68 mmol) were dissolved in DCM (50 mL), and methyl 3-chloro-3-oxopropionate (5.00 g, 36.62 mmol) was added dropwise thereto with stirring at 15° C. After the dropwise addition was completed, the reaction mixture was continued to be stirred at 15° C. for 5 minutes, and then diluted with DCM (50 mL). The reaction solution was washed respectively with 5% of diluted hydrochloric acid (50 mL) and saturated brine (50 mL), and the organic phase was dried over anhydrous sodium sulfate, and then filtered. The filtrate was concentrated to obtain compound 1c. LCMS (ESI) m/z: 264.0 (M+23).

Third Step:

The compound 1c (6.50 g, 26.95 mmol), (E)-4-ethoxy-1,1,1-trifluoro-3-buten-2-one (4.53 g, 26.95 mmol) and DBU (4.31 g, 28.30 mmol) were dissolved in THF (100 mL), and stirred at 15° C. for 2 hours and then concentrated. The residue was dissolved in ethyl acetate (100 mL), and washed respectively with 5% of diluted hydrochloric acid (100 mL) and saturated brine (100 mL). The organic phase was separated, and then dried over anhydrous sodium sulfate, and filtered. The filtrate was concentrated to obtain compound 1d.

Fourth Step:

The compound 1d (10.50 g, 27.54 mmol) and p-toluene-sulfonic acid monohydrate (314.32 mg, 1.65 mmol) were dissolved in toluene (150 mL), and heated to reflux. The water generated by the reaction was separated using a water separator. The reaction solution was refluxed for 1 hour before stopping, and cooled to 15° C., and then washed respectively with water (50 mL), saturated sodium bicarbonate solution (50 mL) and water (50 mL). The organic phase was collected, and then dried over anhydrous sodium sulfate, and filtered. The filtrate was concentrated to obtain compound 1e. LCMS (ESI) m/z: 345.9 (M+1).

Fifth Step:

The compound 1e (8.20 g, 23.75 mmol) was dissolved in THF (80 mL), and then aqueous NaOH solution (80 mL, 2 M) was added thereto. The reaction solution was stirred at 15° C. for 0.5 hour, then concentrated under increased pressure to remove some of the solvent, and then diluted with water (50 mL). The resulting mixture was washed with methyl tert-butyl ether (80 mL*2), and the aqueous phase was separated. The aqueous phase was adjusted to pH 2 with concentrated hydrochloric acid, and then extracted with ethyl acetate (100 mL*2). The combined organic phase was washed with saturated brine (120 mL), dried over anhydrous sodium sulfate, and filtered, and the filtrate was concentrated to obtain compound 1f. $^1$H NMR (400 MHz, CDCl$_3$) δ 8.61 (d, J=7.2 Hz, 1H), 7.49-7.43 (m, 1H), 7.05 (d, J=7.2 Hz, 1H), 6.86-6.81 (m, 2H), 3.76 (s, 3H); LCMS (ESI) m/z: 332.1 (M+1).

Sixth Step:

The compound if (6.30 g, 19.02 mmol) and TEA (2.89 g, 28.53 mmol) were dissolved in t-butanol (100.00 mL), and then diphenylphosphoryl azide (6.28 g, 22.82 mmol) was added thereto. The reaction solution was heated to 75° C. for 2 hours, and then concentrated under reduced pressure. The residue was purified by silica gel column chromatography (petroleum ether:ethyl acetate=10:1) to obtain compound 1g. LCMS (ESI) m/z: 425.0 (M+23).

Seventh Step:

The compound 1g (4.70 g, 11.68 mmol) was dissolved in hydrochloric acid/methanol solution (50 mL, 4 M), stirred at 12° C. for 13 hours, and then concentrated under reduced pressure. The residue was neutralized with saturated sodium carbonate solution (40 mL), and then extracted with ethyl acetate (50 mL*3). The extraction solution was combined, washed with saturated brine (80 mL), dried over anhydrous sodium sulfate, and filtered. The filtrate was concentrated to obtain compound 1h. LCMS (ESI) m/z: 303.0 (M+1).

Eighth Step:

The NBS (64.78 mg, 363.97 μmol) was added to the solution of the compound 1h (100 mg, 330.88 μmol) in DMF (2 mL), and then stirred at 20° C. for 0.5 hour, and the reaction was quenched with water (10 mL). The mixture was extracted with ethyl acetate (10 mL*3), and the combined extraction solution was washed with saturated brine (30 mL), dried over anhydrous sodium sulfate, and then filtered. The filtrate was concentrated under reduced pressure, and purified by preparative TLC (petroleum ether:ethyl acetate=3:1) to obtain compound 1i. $^1$H NMR (400 MHz, CDCl$_3$) δ 7.38-7.34 (m, 1H), 6.86 (s, 1H), 6.79-6.73 (m, 2H), 4.92 (brs, 2H), 3.72 (s, 3H); LCMS (ESI) m/z: 380.9 (M+1).

Ninth Step:

The compound 1i (2.60 g, 6.82 mmol) and copper cyanide (733.17 mg, 8.18 mmol) were dissolved in NMP (15 mL), and heated to 190° C. in a microwave reactor for 4.5 hours. The reaction solution was cooled to 20° C., and ethyl acetate (30 mL), water (30 mL) and concentrated ammonia water (10 mL) were added thereto. The organic phase was separated, and then washed with saturated brine (50 mL), dried over anhydrous sodium sulfate, and filtered and concentrated. The residue was purified by silica gel column chromatography (petroleum ether:ethyl acetate=3:1) to obtain compound 1j. LCMS (ESI) m/z: 328.0 (M+1).

Tenth Step:

The concentrated sulfuric acid (36.80 g, 375.22 mmol) was diluted with water (5 mL), and then the compound 1j (1.20 g, 3.67 mmol) was added thereto. The reaction mixture was heated to 80° C., stirred for 1 hour, then cooled, poured into ice water (200 g), and then adjusted to pH 8 with concentrated ammonia water. The mixture was extracted with ethyl acetate (40 mL*2), and the extraction solution was combined, washed with saturated brine (50 mL), dried over anhydrous sodium sulfate, and filtered and concentrated. The residue was purified by silica gel column chromatography (petroleum ether:ethyl acetate=1:1) to obtain compound 1k. LCMS (ESI) m/z: 346.0 (M+1).

Eleventh Step:

The compound 1k (0.9 g, 2.61 mmol) was added to triethyl orthoformate (30 mL), heated to 80° C. for 2 hours, and then concentrated under reduced pressure. The residue was dissolved in ethyl acetate (30 mL), washed respectively with saturated sodium bicarbonate solution (20 mL) and saturated brine, dried over anhydrous sodium sulfate, and filtered. The filtrate was concentrated to obtain compound 1l. LCMS (ESI) m/z: 356.0 (M+1).

Twelfth Step:

The compound 1l (0.9 g, 2.53 mmol) was added to phosphorus oxychloride (10 mL, 107.61 mmol), heated to 80° C. for 1 hour, and then concentrated under reduced pressure. Toluene (15 mL) was added to the residue, which was then concentrated under reduced pressure to obtain compound 1m. LCMS (ESI) m/z: 374.0 (M+1).

Thirteenth Step:

The compound 1m (1.00 g, 2.68 mmol), tert-butyl piperazine-1-carboxylate (498.41 mg, 2.68 mmol) and TEA (812.36 mg, 8.03 mmol) were dissolved in DCM (20 mL), and then reacted at 15° C. for 2 hours. Additional TEA (812.36 mg, 8.03 mmol) was added thereto, and the reaction was continued at 15° C. for 16 hours. The reaction solution was diluted with DCM (30 mL), washed respectively with 5% of diluted hydrochloric acid (50 mL) and water, dried over anhydrous sodium sulfate, and filtered and concentrated. The residue was purified by silica gel column chromatography (petroleum ether:ethyl acetate=2:1) to obtain compound 1n. $^1$H NMR (400 MHz, CDCl$_3$) δ 8.81 (s, 1H), 7.39-7.34 (m, 1H), 6.89 (s, 1H), 6.80-6.75 (m, 2H), 3.70-3.68 (m, 7H), 3.59-3.52 (m, 4H), 1.43 (s, 9H); LCMS (ESI) m/z: 524.3 (M+1).

Fourteenth Step:

The compound 1n (0.45 g, 859.63 μmol) was added to hydrochloric acid/methanol solution (20 mL, 4 mol/L), reacted at 15° C. for 2 hours, and concentrated to obtain compound 1o. LCMS (ESI) m/z: 424.1 (M+1).

Fifteenth Step:

The 1o (50 mg, 108.74 μmol) and TEA (33.01 mg, 326.21 μmol) were added to DCM (5 mL), and cooled to −30° C., and then acryloyl chloride (11.81 mg, 130.48 μmol) was added thereto. The reaction solution was stirred at −30° C. for 0.5 hour, and then the reaction was quenched with diluted hydrochloric acid (5 mL, 0.5 mol/L). The organic phase was separated, and then dried over anhydrous sodium sulfate, and filtered and concentrated. The residue was purified by preparative TLC (dichloromethane:methanol=20:1) to obtain a crude product. The crude product was purified by preparative HPLC (formic acid) to obtain example 1. $^1$H NMR (400 MHz, CD$_3$OD) δ 8.79 (s, 1H), 7.61-7.55 (m, 1H), 7.29 (s, 1H), 7.06 (d, J=8.8 Hz, 1H), 6.96 (t, J=8.8 Hz, 1H), 6.87-6.80 (m, 1H), 6.30 (dd, J=16.81, 1.88 Hz, 1H), 5.83 (dd, J=10.67, 1.88 Hz, 1H), 4.01 (brs, 4H), 3.91 (brs, 4H), 3.84 (s, 3H); LCMS (ESI) m/z: 478.0 (M+1).

Example 2 and Example 3

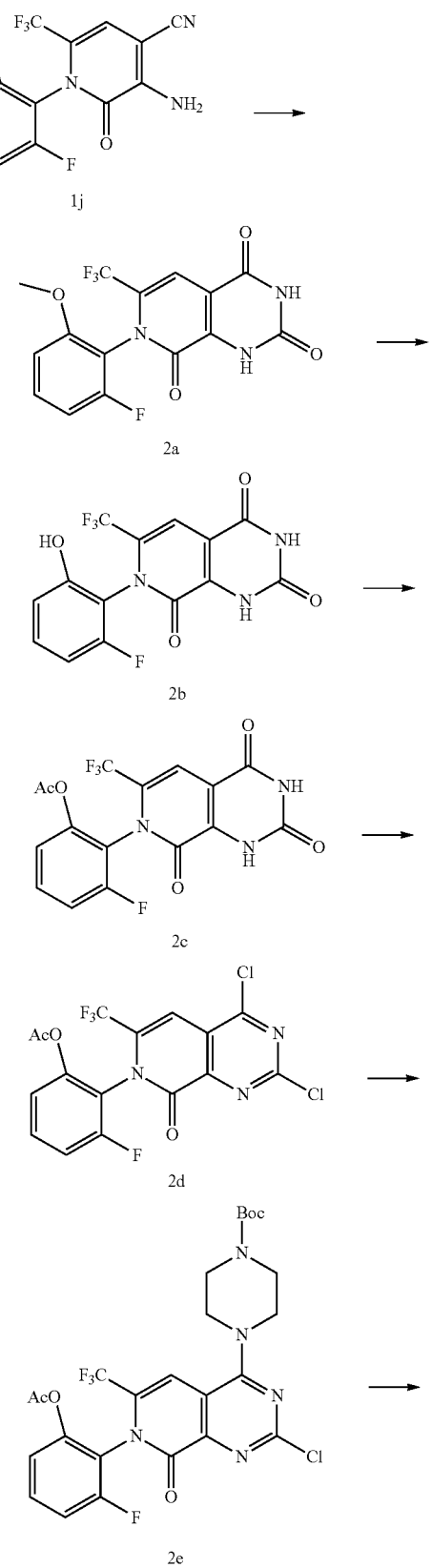

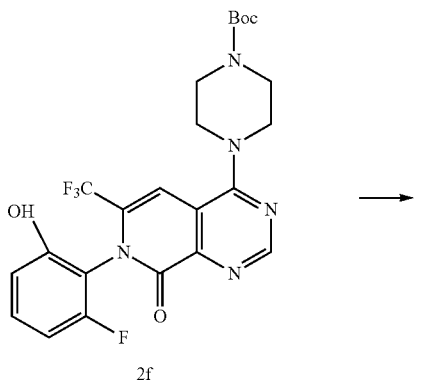

2f

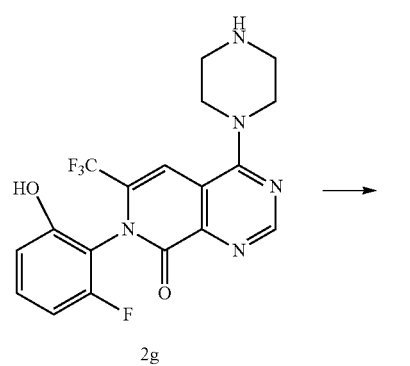

2g

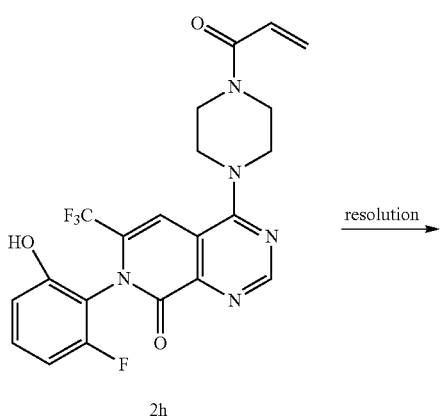

2h

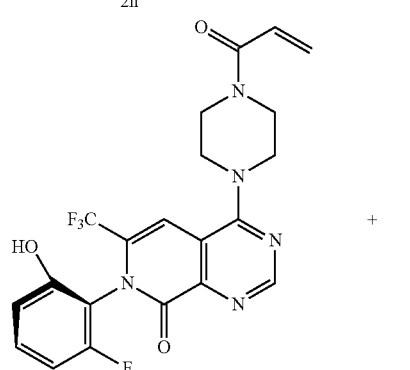

Example 2 or 3

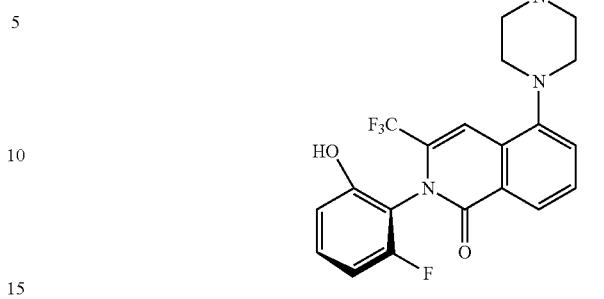

Example 3 or 2

First Step:

The compound 1j (18 g, 55.01 mmol) was dissolved in ionic liquid [HDBU$^+$][TFE$^-$] (30.44 g) at 25° C., and the reaction was carried out under a balloon filled with carbon dioxide gas for 12 hours, and then the reaction solution was poured into water (100 mL) and extracted with ethyl acetate (100 mL*3). The organic phases were combined, dried over anhydrous sodium sulfate, and concentrated under reduced pressure. The crude product was added to a mixed solvent of petroleum ether and ethyl acetate (petroleum ether:ethyl acetate=10:1; 15 mL), stirred and filtered. The filter cake was dried to obtain compound 2a. $^1$H NMR (400 MHz, DMSO-d$_6$) δ 12.03-11.34 (m, 2H), 7.67-7.55 (m, 1H), 7.19 (s, 1H), 7.17-7.04 (m, 2H), 3.79 (s, 3H).

Second Step:

The compound 2a (11.4 g, 30.71 mmol) and pyridine hydrochloride (35.49 g, 307.08 mmol) were mixed, heated to 180° C. and reacted for 15 minutes, and then cooled. The reaction mixture was poured into saturated aqueous sodium bicarbonate solution (100 mL), and extracted with ethyl acetate (100 mL*2). The organic phases were combined, dried over anhydrous sodium sulfate, and then filtered, and the filtrate was concentrated under reduced pressure to obtain compound 2b. LCMS (ESI) m/z: 358.1 (M+1).

Third Step:

The compound 2b (10 g, 27.99 mmol) was dissolved in acetic anhydride (109 g, 100 mL), and then pyridine (2.21 g, 27.99 mmol) was added dropwise thereto. The reaction mixture was reacted at 20° C. for 10 minutes, poured into water (50 mL), and extracted with ethyl acetate (50 mL*2). The extraction solution was combined, dried over anhydrous sodium sulfate, and filtered and concentrated under reduced pressure. The residue was added to a mixed solvent of petroleum ether and ethyl acetate (petroleum ether:ethyl acetate=8:1; 25 mL), stirred, filtered and dried to obtain compound 2c.

Fourth Step:

The compound 2c (1 g, 2.5 mmol) was dissolved in phosphorus oxychloride (3.84 g, 2.33 mL), heated to 120° C. and reacted for 0.5 hour. The reaction solution was concentrated under reduced pressure to obtain compound 2d.

Fifth Step:

The synthesis of compound 2e refers to that of compound 1n. $^1$H NMR (400 MHz, DMSO-d$_6$) δ 7.70 (dt, J=8.4, 6.4 Hz, 1H), 7.50-7.33 (m, 2H), 7.23 (s, 1H), 3.88 (d, J=3.2 Hz, 4H), 3.57 (s, 4H), 2.11 (s, 3H), 1.45 (s, 9H).

Sixth Step:

The compound 2e (150 mg, 0.256 mmol) and TEA (26 mg, 0.256 mmol) were dissolved in methanol (15 mL), and palladium carbon (2.76 mg, 10%) was added thereto. The reaction was carried out under a balloon filled with hydrogen at 30° C. for 1 hour. The reaction solution was filtered and concentrated under reduced pressure. The residue was purified by preparative TLC (petroleum ether:ethyl acetate=1:2) to obtain compound 2f. LCMS (ESI) m/z: 510.0 (M+1).

Seventh Step:

The synthesis of compound 2g refers to that of compound 1o. LCMS (ESI) m/z: 410.0 (M+1).

Eighth Step:

The compound 2g (80 mg, 0.195 mmol) and TEA (39.55 mg, 0.390 mmol) were dissolved in DCM (10 mL), and then acryloyl chloride (17.69 mg, 0.195 mmol) was added dropwise to the reaction solution at 0° C. After the dropwise addition was completed, the reaction solution was reacted at 20° C. for 10 minutes, then poured into water (20 mL), and extracted with ethyl acetate (20 mL*2), and the organic phases were combined, then dried over anhydrous sodium sulfate, and filtered and concentrated under reduced pressure. The residue was purified by preparative TLC (petroleum ether:ethyl acetate=1:2), and the resulting racemic mixture 2h was purified by SFC (column model: Chiralcel OJ-3, 100×4.6 mm I.D., 3 μm; mobile phase A: methanol (containing 0.05% of diethylamine); mobile phase B: carbon dioxide; flow rate: 3 mL/min; wavelength: 220 nm) to obtain example 2 ($t_R$=1.763 min) and example 3 ($t_R$=1.954 min). LCMS (ESI) m/z: 464.1 (M+1).

Example 2: $^1$H NMR (400 MHz, CD$_3$OD) δ 8.79 (s, 1H), 7.47-7.34 (m, 1H), 7.27 (s, 1H), 6.94-6.71 (m, 3H), 6.29 (dd, J=16.8, 1.6 Hz, 1H), 5.82 (dd, J=10.4, 1.6 Hz, 1H), 4.09-3.87 (m, 8H); LCMS (ESI) m/z: 464.1 (M+1).

Example 3: $^1$H NMR (400 MHz, CD$_3$OD) δ 8.79 (s, 1H), 7.48-7.33 (m, 1H), 7.27 (s, 1H), 6.94-6.72 (m, 3H), 6.29 (d, J=16.8 Hz, 1H), 5.83 (d, J=10.4 Hz, 1H), 4.13-3.88 (m, 8H); LCMS (ESI) m/z: 464.1 (M+1).

Example 4

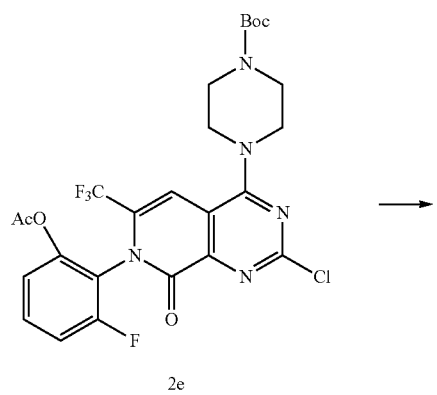

2e

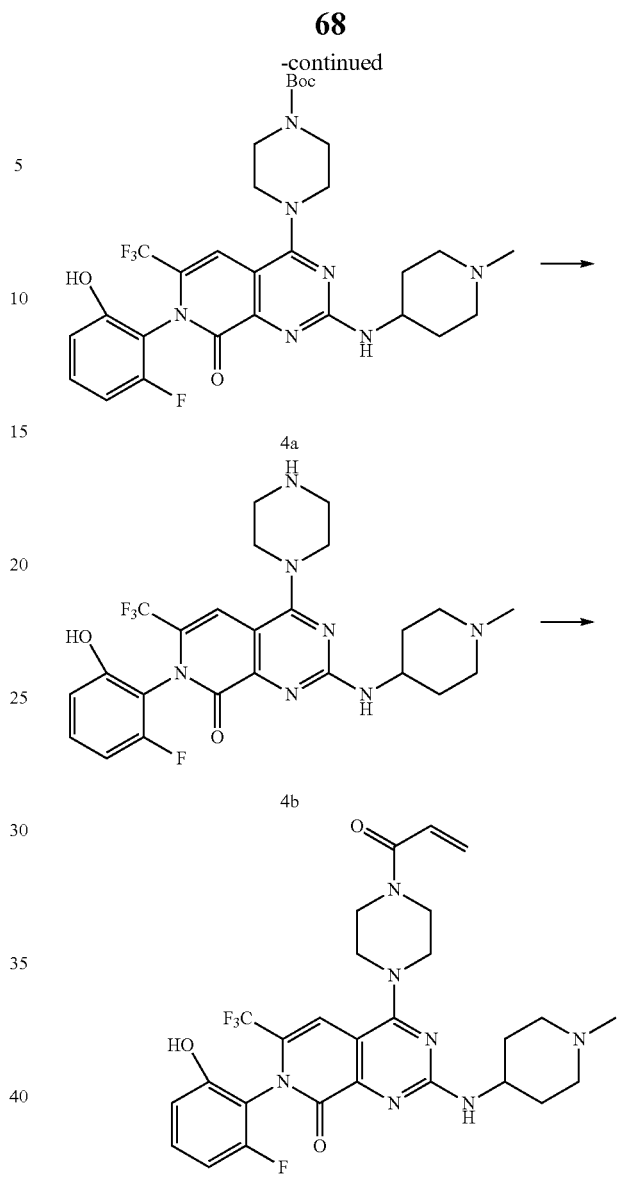

Example 4

First Step:

The 4-amino-1-methylpiperidine (38.98 mg, 341.34 μmol) was dissolved in DCM (3 mL), and TEA (51.81 mg, 512 μmol) and compound 2e (100 mg, 170.67 μmol) were added to this solution, and then stirred at 15° C. for 14 hours. The saturated aqueous ammonium chloride solution (20 mL) was added to the reaction solution to quench the reaction, and then extracted with ethyl acetate (20 mL*2). The organic phase was dried over anhydrous sodium sulfate and concentrated to obtain a crude product. The product was purified by preparative TLC (dichloromethane:methanol=10:1) to obtain compound 4a. $^1$H NMR (400 MHz, CDCl$_3$) δ 7.28-7.19 (m, 1H), 7.06 (br s, 1H), 6.92 (s, 1H), 6.66-6.62 (m, 1H), 4.22-4.11 (m, 1H), 3.62-3.59 (m, 9H), 2.70 (s, 3H), 2.05-2.00 (m, 4H), 1.48 (s, 9H), 1.48-1.38 (m, 4H); LCMS (ESI) m/z: 621.9 (M+1).

Second Step:

The synthesis of compound 4b refers to that of compound 1o. LCMS (ESI) m/z: 522.3 (M+1).

Third Step:

The formate of example 4 was obtained by synthesis referring to example 1. $^1$H NMR (400 MHz, CD$_3$OD) δ 8.54

(s, 1H), 7.40-7.36 (m, 1H), 7.16 (s, 1H), 6.86-6.77 (m, 3H), 6.28 (dd, J=2.0, 2.0 Hz, 1H), 5.82 (dd, J=2.0, 1.6 Hz, 1H), 3.97-3.87 (m, 9H), 3.21-3.18 (m, 2H), 2.92 (s, 2H), 2.71 (s, 3H), 2.22 (d, J=11.6 Hz, 2H), 1.84-1.81 (m, 2H), 2.49 (s, 3H); LCMS (ESI) m/z: 576.1 (M+1).

Example 5

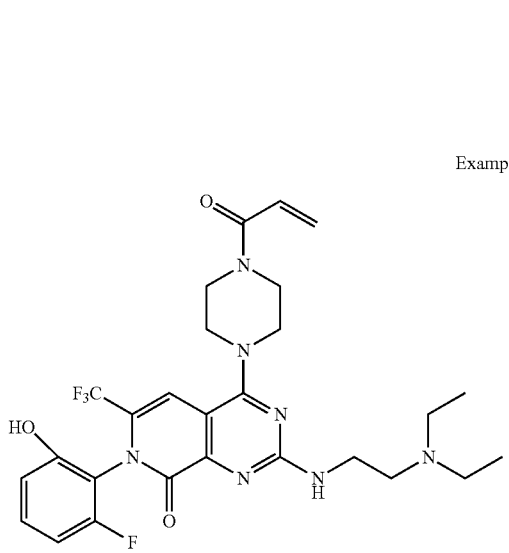

Example 5

The formate of example 5 was obtained by synthesis referring to example 4. $^1$H NMR (400 MHz, CD$_3$OD) δ 8.56 (s, 1H), 7.40-7.34 (m, 1H), 7.21 (s, 1H), 6.83-6.75 (m, 3H), 6.29 (dd, J=2.0, 2.0 Hz, 1H), 5.82 (dd, J=2.0, 1.6 Hz, 1H), 3.89 (s, 8H), 3.71-3.69 (m, 2H), 3.37 (s, 2H), 3.29-3.28 (m, 2H), 1.27 (t, J=5.8 Hz, 6H). LCMS (ESI) m/z: 578.1 (M+1).

Example 6

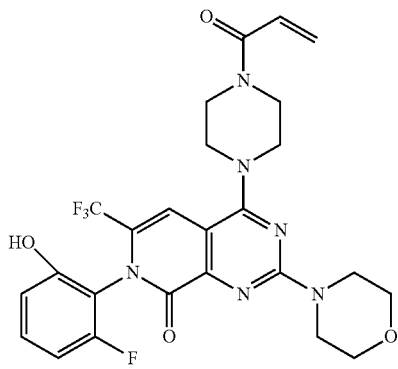

Example 6

The synthesis of example 6 refers to example 4. $^1$H NMR (400 MHz, CD$_3$OD) δ 7.39-7.33 (m, 1H), 7.15 (s, 1H), 6.86-6.74 (m, 3H), 6.28 (dd, J=2.0, 2.0 Hz, 1H), 5.81 (dd, J=2.0, 1.6 Hz, 1H), 3.95 (t, J=4.0 Hz, 9H), 3.90-3.86 (m, 4H), 3.85-3.81 (m, 4H), 3.77-3.75 (m, 4H); LCMS (ESI) m/z: 549.1 (M+1).

Example 7

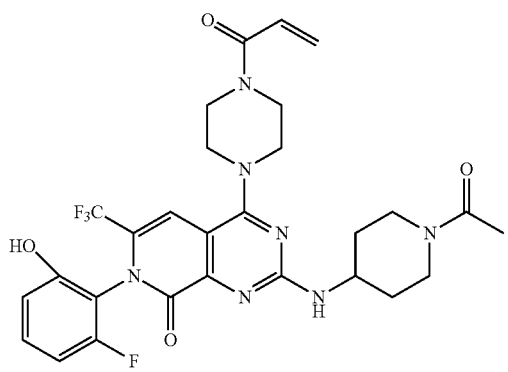

Example 7

The synthesis of example 7 refers to example 4. $^1$H NMR (400 MHz, CD$_3$OD) δ 7.39-7.33 (m, 1H), 7.15 (s, 1H), 6.86-6.76 (m, 3H), 6.29 (d, J=8.4 Hz, 1H), 5.82 (d, J=6.0 Hz, 1H), 4.43-4.16 (m, 2H), 3.96-3.77 (m, 10H), 2.98-2.90 (m, 1H), 2.14 (s, 3H), 2.06 (s, 2H), 1.49 (s, 2H); LCMS (ESI) m/z: 604.2 (M+1).

Example 8

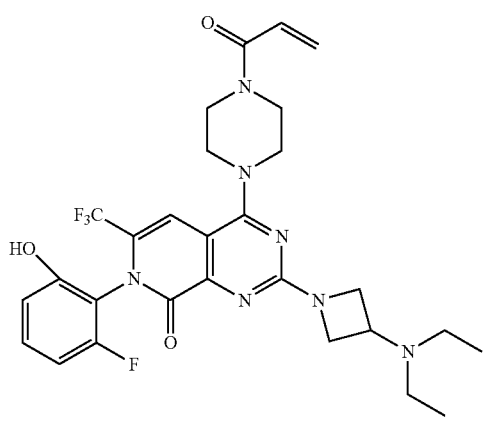

Example 8

The formate of example 8 was obtained by synthesis referring to example 4. $^1$H NMR (400 MHz, CD$_3$OD) δ 8.48 (s, 1H), 7.39-7.33 (m, 1H), 7.14 (s, 1H), 6.86-6.74 (m, 3H), 6.28 (dd, J=2.0, 1.6 Hz, 1H), 5.82 (dd, J=2.0, 2.0 Hz, 1H), 4.40-4.35 (m, 4H), 4.19-4.15 (m, 4H), 3.92-3.90 (m, 1H), 3.90-3.86 (m, 8H), 2.87-2.82 (m, 4H), 1.16 (t, J=6.8 Hz, 6H); LCMS (ESI) m/z: 590.1 (M+1).

Example 9 and Example 10

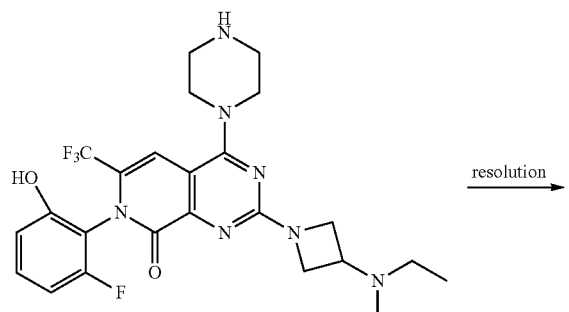

Example 8

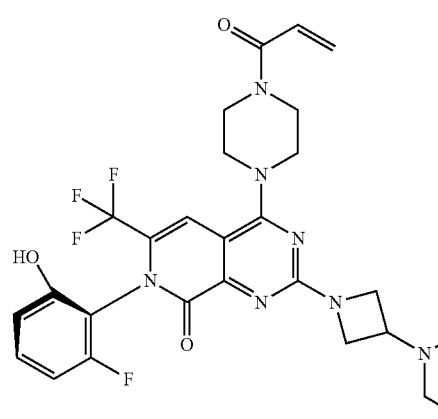

Example 9 or 10

+

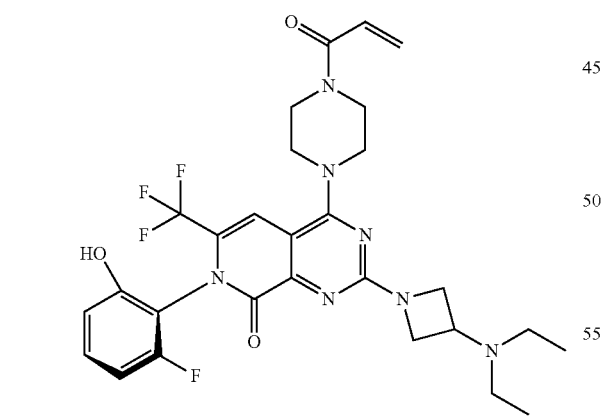

Example 10 or 9

Example 8 was purified by SFC (column model: Chiralcel OJ-3, 100×4.6 mm 3 μm; mobile phase A: methanol (containing 0.05% of diethylamine); mobile phase B: carbon dioxide; flow rate: 3 mL/min; wavelength: 220 nm) to obtain example 9 ($t_R$=2.90 min) and example 10 ($t_R$=3.11 min). LCMS (ESI) m/z: 590.1 (M+1).

Example 9: $^1$H NMR (400 MHz, CD$_3$OD) δ 7.36 (dt, J=8.4, 6.5 Hz, 1H), 7.13 (s, 1H), 6.89-6.71 (m, 3H), 6.28 (dd, J=16.8, 2.0 Hz, 1H), 5.81 (dd, J=10.6, 2.0 Hz, 1H), 4.59 (br s, 1H), 4.40-4.26 (m, 2H), 4.18-4.04 (m, 2H), 3.92-3.71 (s, 9H), 2.71 (q, J=7.2 Hz, 4H), 1.10 (t, J=7.2 Hz, 6H); LCMS (ESI) m/z: 590.1 (M+1).

Example 10: $^1$H NMR (400 MHz, CD$_3$OD) δ 7.36 (dt, J=8.4, 6.5 Hz, 1H), 7.13 (s, 1H), 6.89-6.71 (m, 3H), 6.28 (dd, J=16.8, 2.0 Hz, 1H), 5.81 (dd, J=10.6, 2.0 Hz, 1H), 4.59 (br s, 1H), 4.40-4.26 (m, 2H), 4.18-4.04 (m, 2H), 3.92-3.71 (s, 9H), 2.71 (q, J=7.2 Hz, 4H), 1.10 (t, J=7.2 Hz, 6H); LCMS (ESI) m/z: 590.1 (M+1).

Example 11

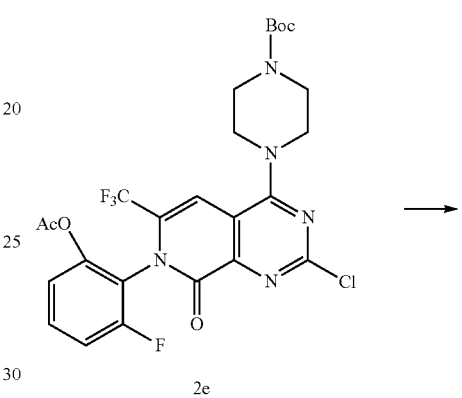

2e

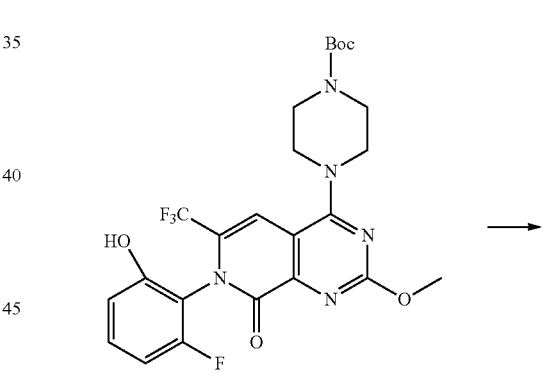

11a

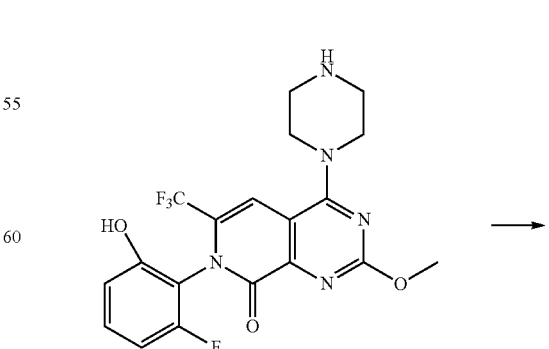

11b

Example 11

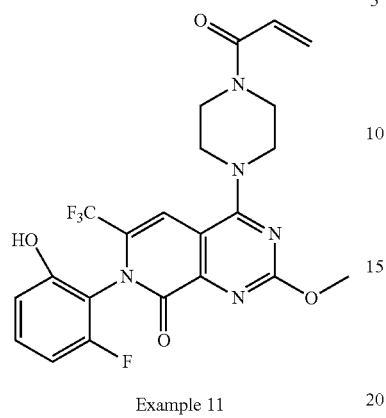

Example 11

First Step:

The compound 2e (80 mg, 136.53 μmol) and sodium methoxide (29.50 mg, 546.14 μmol) were dissolved in methanol (3 mL), and then stirred at 20° C. for 30 minutes. The reaction solution was concentrated to obtain a crude product. The product was purified by preparative TLC (dichloromethane:methanol=10:1) to obtain compound 11a. LCMS (ESI) m/z: 558.3 (M+1).

Second Step:

The synthesis of compound 11b refers to that of compound 10.

Third Step:

The synthesis of example 11 refers to example 1. $^1$H NMR (400 MHz, CD$_3$OD) δ 8.45 (brs, 1H), 7.29-7.21 (m, 1H), 7.13 (s, 1H), 6.77-6.60 (m, 3H), 6.21-6.14 (m, 1H), 5.73-5.68 (m, 1H), 3.96 (s, 3H), 3.92-3.83 (m, 4H), 3.83-3.75 (m, 4H); LCMS (ESI) m/z: 494.0 (M+1).

Example 12

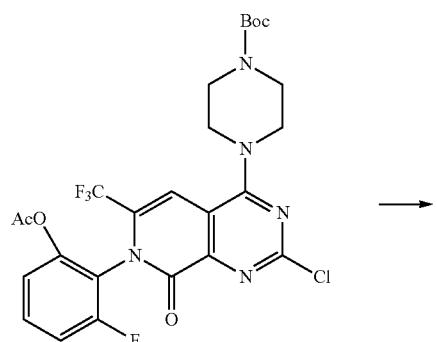

2e

First Step:

The compound 2e (100 mg, 170.67 μmol) and 1-methylpiperidine-4-ol (196.56 mg, 1.71 mmol) were dissolved in DMSO (2 mL) and dioxane (2 mL), and potassium fluoride (99.16 mg, 1.71 mmol) was added to this solution, and then heated to 120° C. and stirred for 2 hours. The water (10 mL) was added to the reaction solution to quench the reaction, and then extracted with ethyl acetate (20 mL*2). The organic phases were combined, washed with saturated brine (10 mL), dried over anhydrous sodium sulfate, and filtered. The filtrate was concentrated to obtain a crude product. The product was purified by preparative TLC (dichloromethane:methanol=10:1) to obtain compound 12a. LCMS (ESI) m/z: 623.1 (M+1).

Second Step:

The synthesis of compound 12b refers to that of compound 1o. LCMS (ESI) m/z: 523.1 (M+1).

Third Step:

The synthesis of example 12 refers to example 1. $^1$H NMR (400 MHz, CD$_3$OD) δ 7.30-7.21 (m, 1H), 7.14 (s, 1H), 6.75-6.61 (m, 3H), 6.18 (dd, J=16.0, 4.0 Hz, 1H), 5.74-5.68

(m, 1H), 5.28-5.14 (m, 1H), 3.91-3.75 (m, 8H), 2.95-2.80 (m, 2H), 2.70-2.55 (m, 2H), 2.41 (s, 3H), 2.15-2.00 (m, 2H), 1.97-1.85 (m, 2H); LCMS (ESI) m/z: 577.2 (M+1).

Example 13

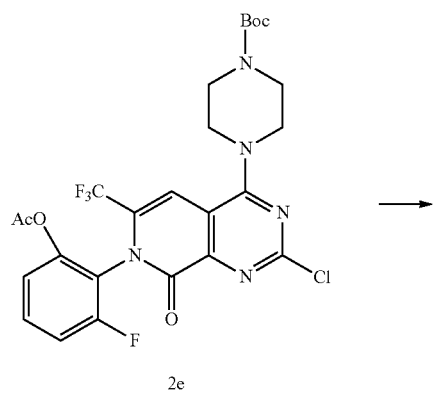

2e

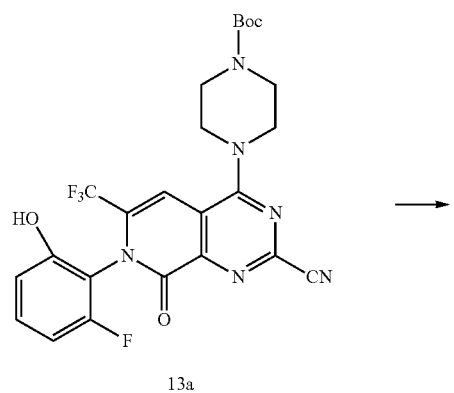

13a

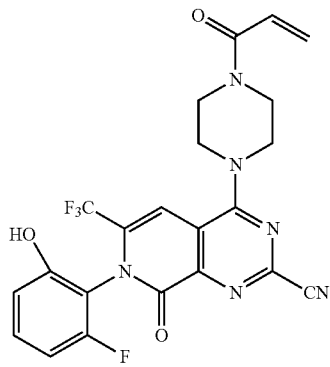

Example 13

First Step:

The potassium cyanide (0.2 g, 3.07 mmol) was dissolved in DMSO (4 mL), and 18-crown-6 (338.33 mg, 1.28 mmol) and compound 2e (150 mg, 256 μmol) were added to this solution, and then stirred at 15° C. for 15 hours. The reaction was quenched with saturated aqueous sodium bicarbonate solution (20 mL), and extracted with ethyl acetate (20 mL*2). The organic phase was dried over anhydrous sodium sulfate and concentrated to obtain a crude product. The product was purified by preparative TLC (petroleum ether:ethyl acetate=1:1) to obtain compound 13a. LCMS (ESI) m/z: 535.1 (M+1).

Second Step:

The synthesis of compound 13b refers to that of compound 1o. LCMS (ESI) m/z: 435.0 (M+1).

Third Step:

The synthesis of the formate of example 13 refers to example 1. $^1$H NMR (400 MHz, CD$_3$OD) δ 8.54 (s, 1H), 7.42-7.38 (m, 1H), 7.30 (s, 1H), 6.86-6.74 (m, 3H), 6.31 (dd, J=1.6, 1.6 Hz, 1H), 5.87-5.80 (dd, J=2.0, 2.0 Hz, 1H), 4.08-4.01 (m, 4H), 3.92-3.88 (m, 4H); LCMS (ESI) m/z: 489.0 (M+1).

Example 14

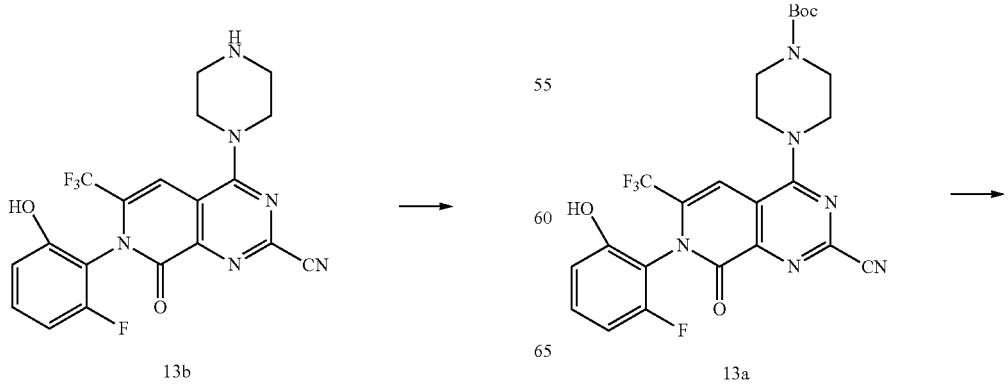

13b 13a

-continued

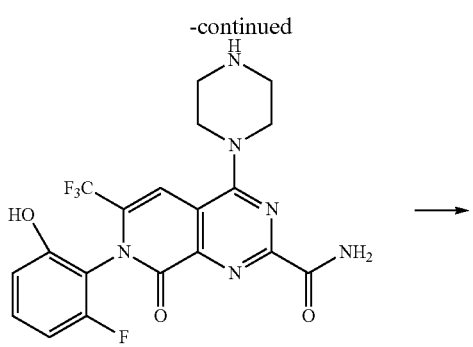

14a

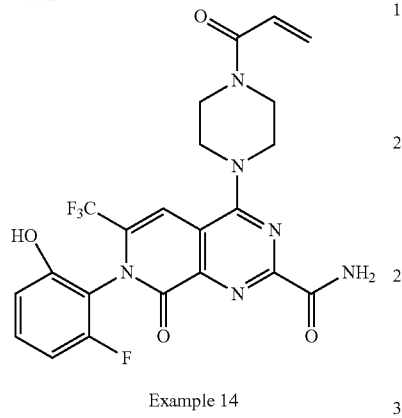

Example 14

First Step:

The compound 13a (55 mg, 102.91 μmol) was dissolved in dioxane solution (2 mL), and hydrochloric acid/dioxane solution (4.13 mL, 4M) was added to this solution, and then stirred at 15° C. for 1 hour and filtered. The filtrate was concentrated to obtain compound 14a. LCMS (ESI) m/z: 453.0 (M+1).

Second Step:

The formate of example 14 was obtained by synthesis referring to example 1. $^1$H NMR (400 MHz, CD$_3$OD) δ 8.55 (s, 1H), 7.31-7.27 (m, 1H), 6.84 (dd, J=10.4, 10.4 Hz, 1H), 6.70 (d, J=8.8 Hz, 1H), 6.57-6.22 (m, 1H), 6.32 (dd, J=2.0, 2.0 Hz, 1H), 5.85 (d, J=12.8 Hz, 1H), 4.30-4.16 (m, 4H), 3.99-3.91 (m, 4H); LCMS (ESI) m/z: 507.0 (M+1).

Example 15

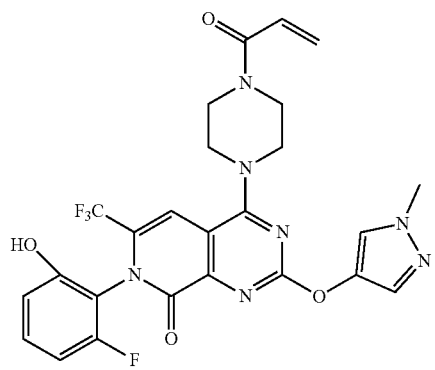 [SMILES: C=CC(=O)N1CCN(c2nc(Oc3cnn(C)c3)nc3c(=O)n(-c4c(O)cccc4F)c(C(F)(F)F)cc23)CC1]

The synthesis of example 15 refers to example 12. $^1$H NMR (400 MHz, CD$_3$OD) δ 7.91 (s, 1H), 7.59 (s, 1H), 7.43-7.34 (m, 1H), 7.28 (s, 1H), 6.86-6.74 (m, 3H), 6.33-6.25 (m, 1H), 5.85-5.79 (m, 1H), 3.99-3.94 (m, 4H), 3.91 (s, 3H), 3.90-3.85 (m, 4H); LCMS (ESI) m/z: 560.1 (M+1).

Example 16

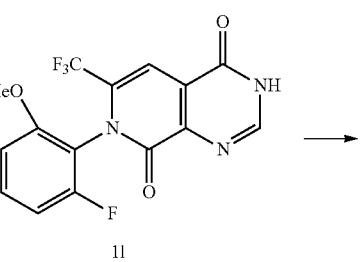

11

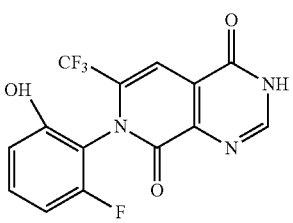

16a

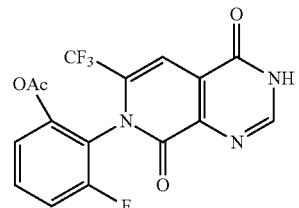

16b

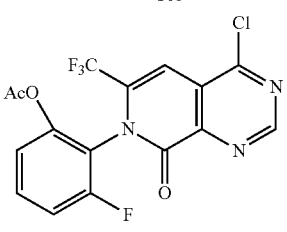

16c

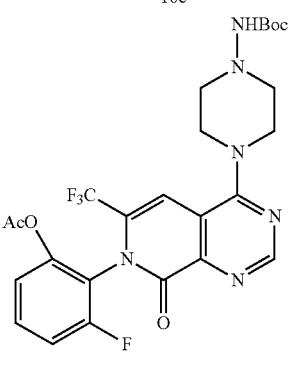

16d

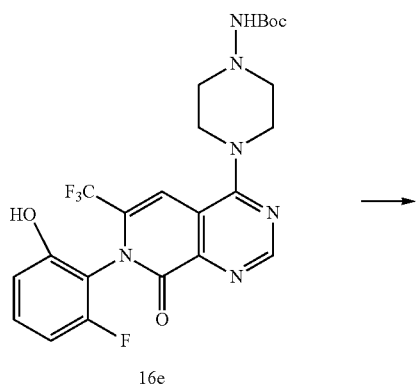

16e

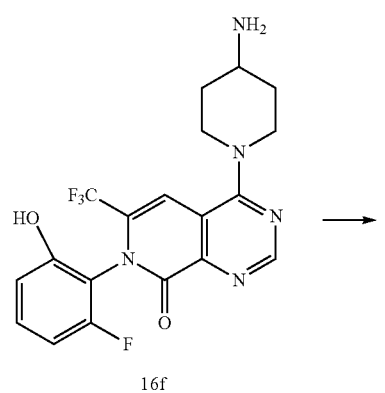

16f

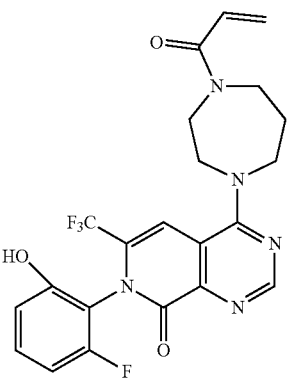 [SMILES: C=CC(=O)N1CCCN(c2ncnc3c(=O)n(-c4c(O)cccc4F)c(C(F)(F)F)cc23)CC1]

(1.39 g, 17.58 mmol) was added thereto. The reaction solution was reacted at 20° C. for 10 minutes, then poured into water (30 mL), and extracted with ethyl acetate (50 mL*2). The organic phases were combined, dried over anhydrous sodium sulfate, and filtered. The filtrate was concentrated under reduced pressure to obtain compound 16b.

Third Step:

The synthesis of compound 16c refers to that of compound 1m.

Fourth Step:

The synthesis of compound 16d refers to that of compound 1n. LCMS (ESI) m/z: 566.1 (M+1).

Fifth Step:

The compound 16d (60.0 mg, 106.1 μmol) was dissolved in THF (3 mL) and water (3 mL), and lithium hydroxide monohydrate (251.8 mg, 6.0 mmol) was added to this solution, and then stirred at 25° C. for 0.2 hour. The reaction mixture was quenched with diluted hydrochloric acid (10 mL, 1 mol/L), and extracted with ethyl acetate (15 mL*3). The organic phases were combined, dried over anhydrous sodium sulfate, and filtered. The filtrate was concentrated to obtain compound 16e. LCMS (ESI) m/z: 524.1 (M+1).

Sixth Step:

The synthesis of compound 16f refers to that of compound 1o. LCMS (ESI) m/z: 424.1 (M+1).

Seventh Step:

The synthesis of example 16 refers to example 1. $^1$H NMR (400 MHz, CD$_3$OD) δ 8.75 (s, 1H), 7.41-7.36 (m, 1H), 7.20 (s, 1H), 6.84-6.76 (m, 2H), 6.25 (d, J=6.0 Hz, 2H), 5.69 (t, J=2.0 Hz, 1H), 4.43 (d, J=10.0 Hz, 2H), 4.18-4.15 (m, 1H), 3.53-3.46 (m, 2H), 2.71 (s, 3H), 2.10 (d, J=11.2 Hz, 2H), 1.73-1.64 (m, 2H); LCMS (ESI) m/z: 478.2 (M+1).

Example 17

Example 16

First Step:

The compound 11 (7.00 g, 19.70 mmol) and pyridine hydrochloride (22.77 g, 197.05 mmol) were mixed, and then stirred at 180° C. for 15 minutes. The reaction mixture was poured into saturated sodium bicarbonate solution (50 mL), and extracted with ethyl acetate (80 mL*2). The organic phases were combined, dried over anhydrous sodium sulfate, and filtered. The filtrate was concentrated under reduced pressure to obtain compound 16a.

Second Step:

The compound 16a (6.00 g, 17.58 mmol) was dissolved in acetic anhydride (35.9 g, 351.68 mmol), and then pyridine The synthesis of example 17 refers to example 16. $^1$H NMR (400 MHz, CD$_3$OD) δ 8.68 (d, J=3.6 Hz, 1H), 7.41-7.29 (m, 2H), 6.88-6.67 (m, 3H), 6.21-6.08 (m, 1H), 5.80-5.64 (m, 1H), 4.61 (s, 4H), 4.20-4.13 (m, 2H), 4.12-3.94 (m, 4H), 3.87-3.71 (m, 2H), 2.15 (br s, 2H); LCMS (ESI) m/z: 478.1 (M+1).

Example 18

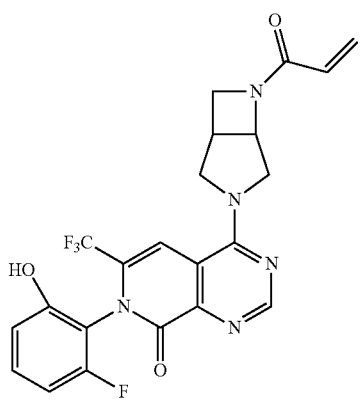 [SMILES: C=CC(=O)N1CC2CN(c3ncnc4c(=O)n(-c5c(O)cccc5F)c(C(F)(F)F)cc34)CC21]

The synthesis of example 18 refers to example 16. ¹H NMR (400 MHz, CD₃OD) δ 8.68 (s, 1H), 7.53 (s, 1H), 7.44-7.34 (m, 1H), 6.87-6.81 (m, 1H), 6.81-6.71 (m, 1H), 6.59-6.16 (m, 2H), 5.86-5.70 (m, 1H), 5.30-5.05 (m, 1H), 4.77-4.54 (m, 3H), 4.50-4.15 (m, 1H), 4.00-3.59 (m, 3H), 3.51-3.38 (m, 1H); LCMS (ESI) m/z: 476.0 (M+1).

Example 19

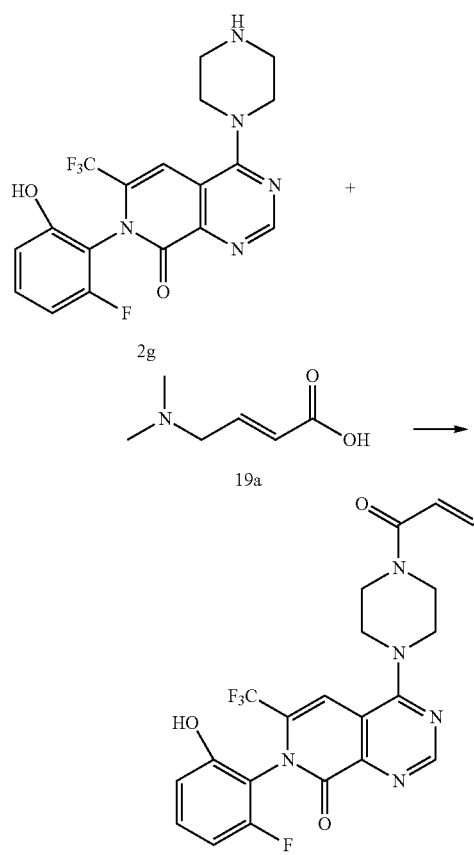

The compound 19a (22.29 mg, 134.59 μmol), HOBt (9.09 mg, 67.30 μmol) and EDCl.HCl (12.90 mg, 67.30 μmol) were dissolved in DMF (5 mL), and TEA (6.81 mg, 67.30 μmol) and compound 2g (30 mg, 67.30 μmol) were added to this solution under the protection of nitrogen, and then stirred at 25° C. for 2 hours. The reaction solution was quenched with water (10 mL) and extracted with DCM (20 mL*2). The organic phases were combined, washed with saturated brine (10 mL), dried over anhydrous sodium sulfate, and filtered. The filtrate was concentrated under reduced pressure to obtain a crude product. The crude product was purified successively by preparative TLC (dichloromethane:methanol=10:1) and preparative HPLC (formic acid) to obtain the formate of example 19. ¹HNMR (400 MHz, CD₃OD) δ 8.80 (s, 1H), 8.44 (s, 1H), 7.44-7.35 (m, 1H), 7.27 (s, 1H), 6.87-6.74 (m, 4H), 4.05-3.96 (m, 4H), 3.96-3.86 (m, 4H), 3.69-3.64 (m, 2H), 2.68 (s, 6H); LCMS (ESI) m/z: 521.1 (M+1).

Example 20

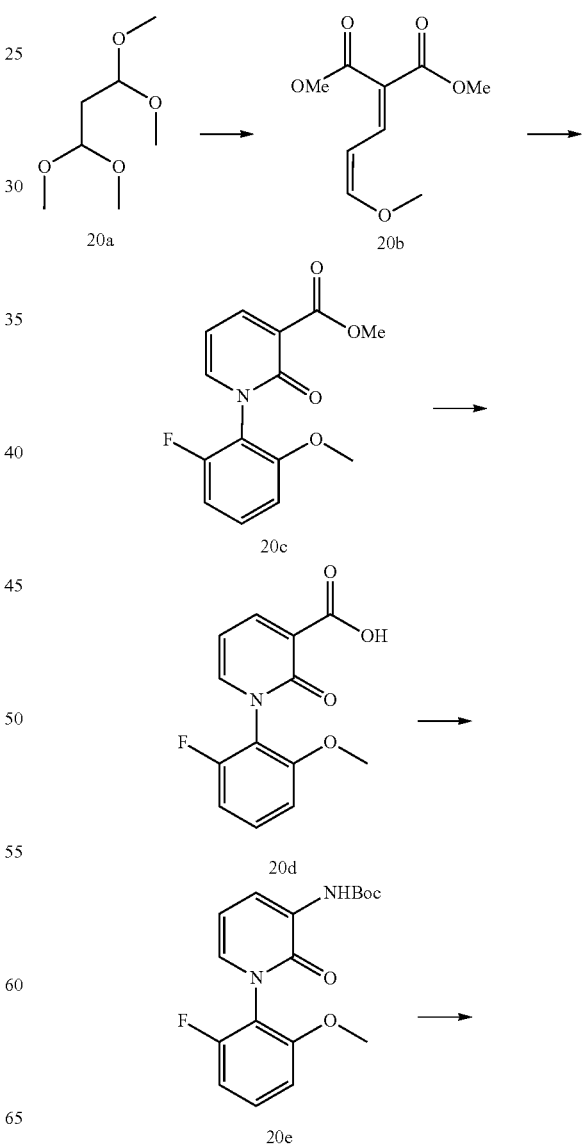

-continued

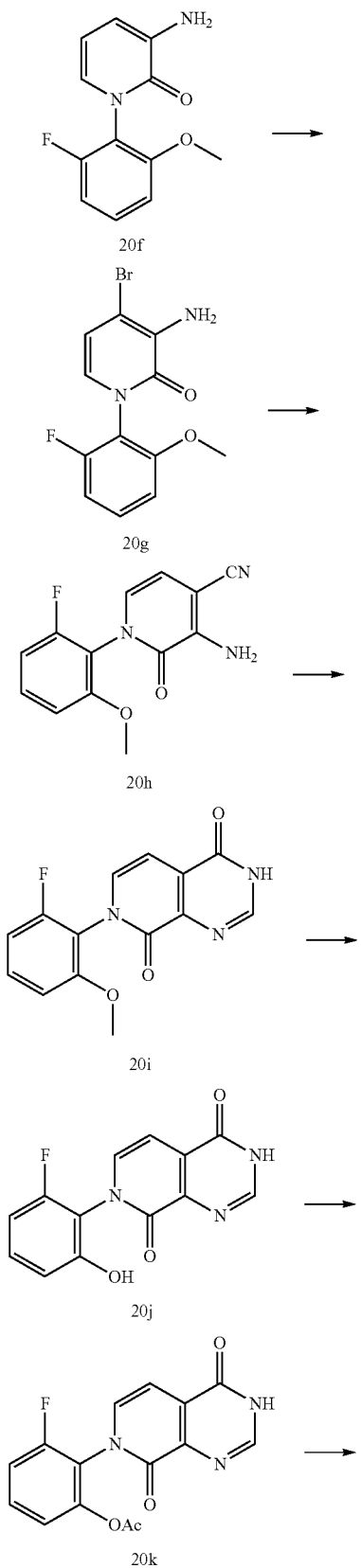

-continued

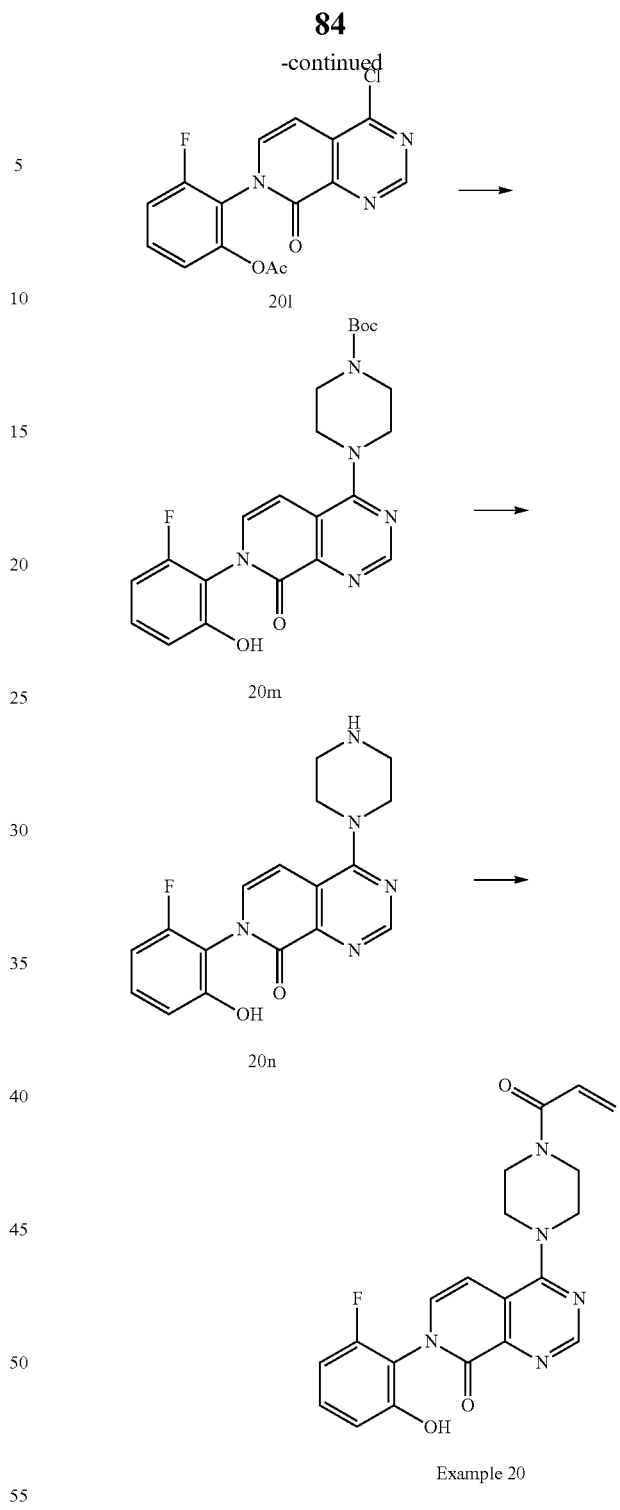

Example 20

First Step:

Dimethyl malonate (50 g, 378.46 mmol, 43.48 mL, 1 eq) was added dropwise to the mixed solution of compound 20a (93.21 g, 567.69 mmol, 93.97 mL, 1.5 eq) and zinc chloride (2.58 g, 18.92 mmol, 886.29 µl, 0.05 eq) in acetic anhydride (77.27 g, 756.92 mmol, 70.89 mL, 2 eq), and the dropwise addition was completed within 0.5 hour. The above reaction solution was heated to 140° C. and stirred for 1 hour. The reaction solution was concentrated under reduced pressure, and the resulting residue was dissolved in acetic anhydride (80 mL) and refluxed and reacted for 1 hour. TLC (petroleum ether:ethyl acetate=10:1) showed that new spots were generated. The reaction solution was concentrated, and the resulting residue was purified by silica gel column chromatography (petroleum ether:ethyl acetate=10:1) to obtain compound 20b. ¹H NMR (400 MHz, CDCl₃) δ 7.45 (d, J=12.0 Hz, 1H), 7.11 (d, J=12.4 Hz, 1H), 6.25 (t, J=12.4 Hz, 1H), 3.82 (s, 2H), 3.84-3.81 (m, 1H), 3.76 (d, J=4.0 Hz, 6H).

Second Step:

To a solution of compound 20b (28.37 g, 141.70 mmol, 1 eq) and 2-fluoro-6-methoxy-aniline (20 g, 141.70 mmol, 1 eq) in methanol (150 mL) was added p-toluenesulfonic acid monohydrate (2.70 g, 14.17 mmol, 0.1 eq), and the above mixture was heated to 80° C. and stirred for 12 hours. LCMS detected the MS of the target product. The reaction solution was concentrated, and the resulting residue was purified by silica gel column chromatography (petroleum ether:ethyl acetate=2:1) to obtain compound 20c. ¹H NMR (400 MHz, CDCl₃) δ 7.69-7.54 (m, 2H), 6.94-6.81 (m, 2H), 6.74-6.59 (m, 2H), 6.40 (dt, J=12.4, 2.4 Hz, 1H), 3.83 (s, 3H), 3.76 (s, 3H), 3.71 (s, 3H); LCMS (ESI) m/z: 278.0 (M+1).

Third Step:

The synthesis of compound 20d refers to that of compound 1f.

Fourth Step:

The synthesis of compound 20e refers to that of compound 1g. ¹H NMR (400 MHz, CDCl₃) δ 7.97 (d, J=7.0 Hz, 1H), 7.59 (s, 1H), 7.31 (dt, J=8.4, 6.4 Hz, 1H), 6.86-6.67 (m, 3H), 6.21 (t, J=7.2 Hz, 1H), 3.80-3.69 (m, 3H), 1.49-1.36 (m, 9H).

Fifth Step:

The synthesis of compound 20f refers to that of compound 1h.

Sixth Step:

The synthesis of compound 20g refers to that of compound 1i.

Seventh Step:

The synthesis of compound 20h refers to that of compound 1j.

Eighth Step:

A mixture of compound 20h (1.4 g, 5.40 mmol, 1 eq), formic acid (5.19 g, 108.01 mmol, 20 eq) and sulfuric acid (1.59 g, 16.20 mmol, 863.60 µl, 3 eq) was heated to 100° C. and stirred for 0.5 hour. TLC (petroleum ether:ethyl acetate=1:1) showed that new spots were generated. The above reaction solution was poured into water (30 mL) and extracted with ethyl acetate (30 mL*2). The combined organic phase was dried over anhydrous sodium sulfate and filtered, and the filtrate was concentrated to obtain a crude compound 20i, which was directly used in the next step without purification.

Ninth Step:

The synthesis of compound 20j refers to that of compound 2b. LCMS (ESI) m/z: 274.0 (M+1).

Tenth Step:

The synthesis of compound 20k refers to that of compound 2c. LCMS (ESI) m/z: 316.2 (M+1).

Eleventh Step:

The synthesis of compound 20l refers to that of compound 1m.

Twelfth Step:

The synthesis of compound 20m refers to that of compound 1n. LCMS (ESI) m/z: 442.2 (M+1).

Thirteenth Step:

The synthesis of compound 20n refers to that of compound 1o. LCMS (ESI) m/z: 342.2 (M+1).

Fourteenth Step:

The synthesis of example 20 refers to example 1. ¹H NMR (400 MHz, CD₃OD) δ 8.73 (s, 1H), 7.45-7.25 (m, 2H), 6.95-6.75 (m, 4H), 6.28 (dd, J=16.8, 2.0 Hz, 1H), 5.82 (dd, J=10.6, 2.0 Hz, 1H), 3.90 (s, 8H); LCMS (ESI) m/z: 396.1 (M+1).

Example 21

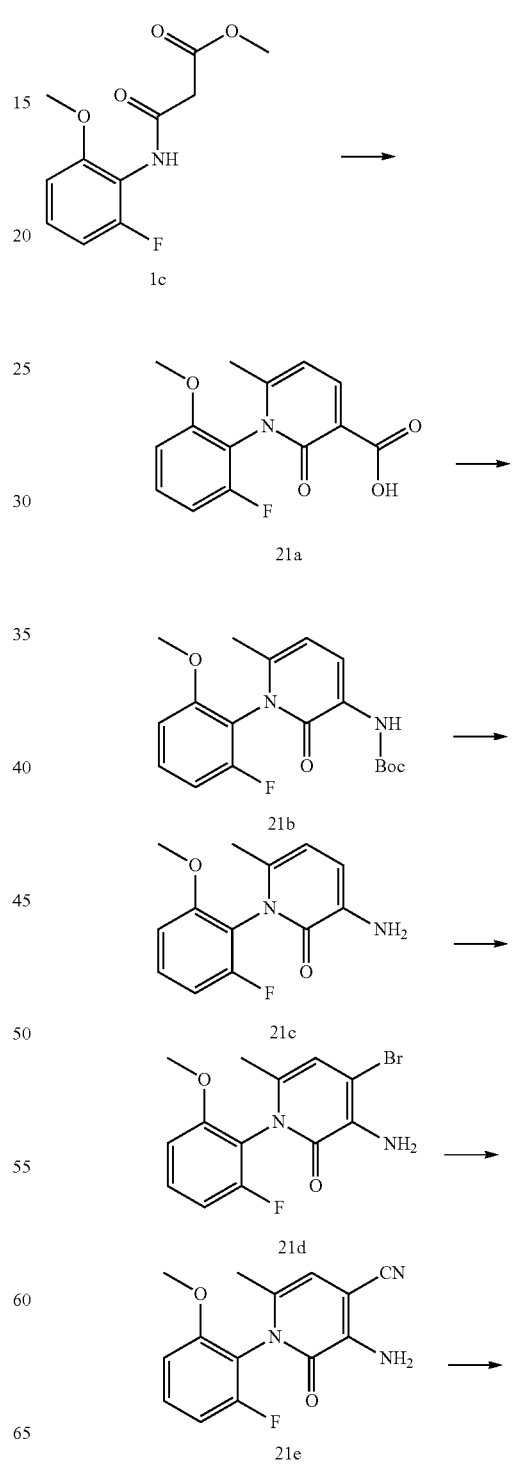

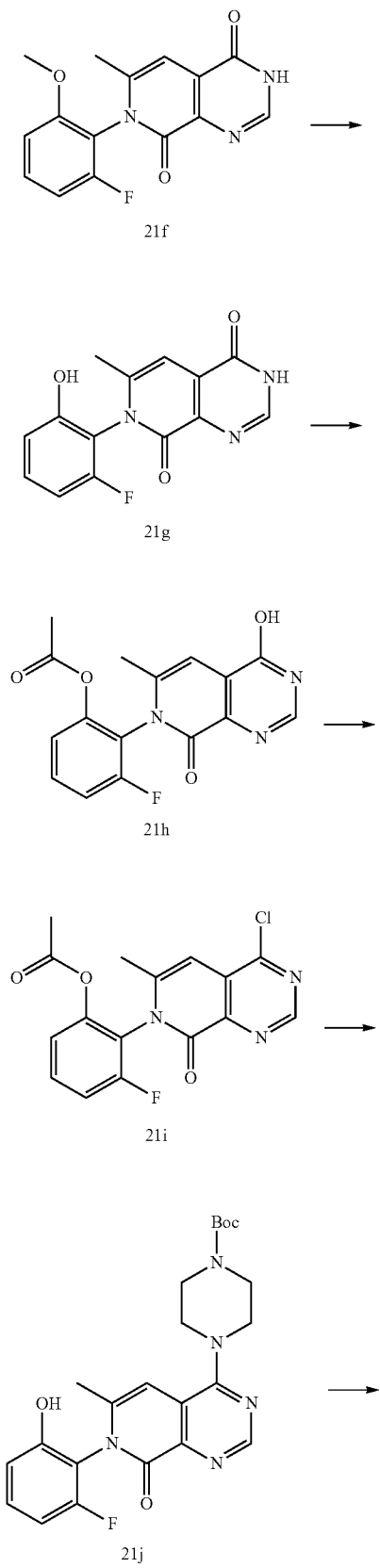

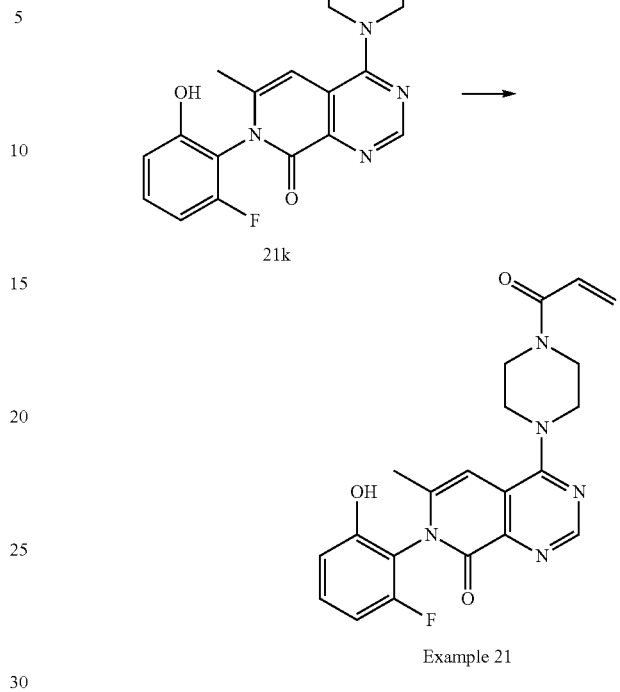

First Step:

To a solution of compound 1c (19.5 g, 80.84 mmol, 1 eq) in methanol (100 mL) was slowly added freshly prepared sodium methoxide (prepared from sodium (2.23 g, 97.01 mmol, 2.30 mL, 1.2 eq) and methanol (100 mL)). The reaction mixture was heated to 70° C. and reacted for 16 hours. LCMS showed that the reaction of the raw materials was complete and detected the MS of the target product. The reaction solution was concentrated, and the resulting residue was dissolved in water (300 mL) and stirred at 30° C. for 30 minutes, and then extracted with ethyl acetate (200 mL). The organic phase was adjusted to pH 2 with 35% of concentrated hydrochloric acid, and then extracted with ethyl acetate (200 mL*3). The combined organic phase was washed with saturated brine (100 mL), dried over anhydrous sodium sulfate and concentrated under reduced pressure. At 25° C., the resulting residue was stirred in a mixed solution of petroleum ether:ethyl acetate=1:2 (30 mL) for 16 hours and filtered, and the filter cake was dried in vacuo to obtain compound 21a. LCMS (ESI) m/z: 278.0 (M+1).

Second Step:

The synthesis of compound 21b refers to that of compound 1g. LCMS (ESI) m/z: 293.2 (M+1-56).

Third Step:

The synthesis of compound 21c refers to that of compound 1h. LCMS (ESI) m/z: 249.2 (M+1).

Fourth Step:

The synthesis of compound 21d refers to that of compound 1i. LCMS (ESI) m/z: 327.1 (M+1).

Fifth Step:

The synthesis of compound 21e refers to that of compound 1j. LCMS (ESI) m/z: 274.3 (M+1).

Sixth Step:

The synthesis of compound 21f refers to that of compound 20i. LCMS (ESI) m/z: 302.2 (M+1).

Seventh Step:

The synthesis of compound 21g refers to that of compound 2b. $^1$H NMR (400 MHz, DMSO-d$_6$) δ 8.10 (s, 1H), 7.44-7.22 (m, 1H), 6.96-6.78 (m, 2H), 6.71 (s, 1H), 2.01 (s, 3H); LCMS (ESI) m/z: 288.1 (M+1).

Eighth Step:

The synthesis of compound 21h refers to that of compound 2c. LCMS (ESI) m/z: 330.2 (M+1).

Ninth Step:

The synthesis of compound 21i refers to that of compound 1m. LCMS (ESI) m/z: 344.0 (M+1−35+31).

Tenth Step:

The synthesis of compound 21j refers to that of compound 1n. LCMS (ESI) m/z: 456.4 (M+1).

Eleventh Step:

The synthesis of compound 21k refers to that of compound 1o. LCMS (ESI) m/z: 356.3 (M+1).

Twelfth Step:

The synthesis of example 21 refers to example 1. 1H NMR (400 MHz, CD$_3$OD) δ 8.74-8.63 (m, 1H), 8.68 (s, 1H), 7.39 (dt, J=8.4, 6.6 Hz, 1H), 6.93-6.79 (m, 3H), 6.69 (s, 1H), 6.29 (dd, J=16.8, 2.0 Hz, 1H), 5.89-5.78 (m, 1H), 3.89 (s, 8H), 2.17 (s, 3H); LCMS (ESI) m/z: 410.0 (M+1).

Example 22

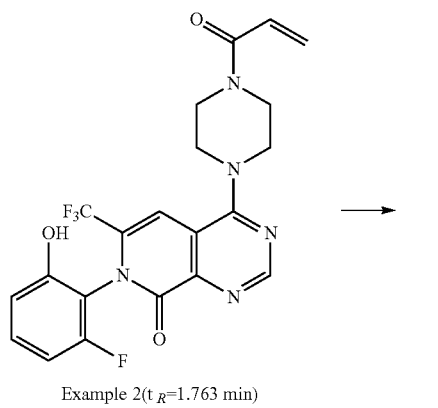

Example 2(t$_R$=1.763 min)

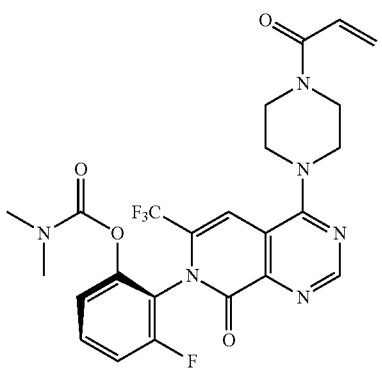

or

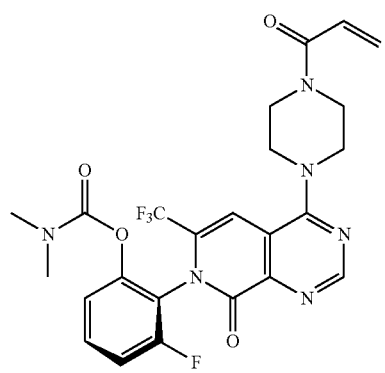

Example 22

At 0° C. and under the protection of nitrogen, to a solution of example 2 (20 mg, 43.16 μmol, 1 eq) and TEA (5 mg, 49.41 μmol, 6.88 μl, 1.14 eq) in DCM (2 mL) was added dimethyl carbamoyl chloride (5 mg, 46.49 μmol, 4.27 μl, 1.08 eq). The above reaction solution was stirred at 0° C. for 0.5 hour. LCMS detected the production of the target product. The reaction solution was concentrated under reduced pressure, and the resulting residue was purified by preparative HPLC (formic acid) to obtain example 22. $^1$H NMR (400 MHz, CD$_3$OD) δ 8.79 (s, 1H), 7.69-7.60 (m, 1H), 7.48-7.41 (m, 1H), 7.33 (s, 1H), 7.28-7.19 (m, 1H), 6.88-6.78 (m, 1H), 6.30 (dd, J=16.8, 2.0 Hz, 1H), 5.83 (dd, J=10.6, 1.9 Hz, 1H), 4.09-3.96 (m, 4H), 3.95-3.85 (m, 4H), 2.89 (s, 3H), 2.74 (s, 3H); LCMS (ESI) m/z: 535.0 (M+1).

Example 23

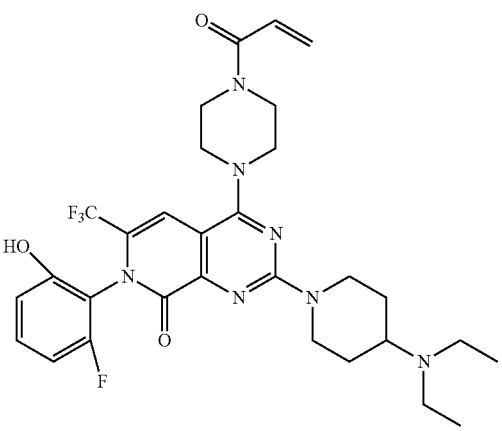 [SMILES: C=CC(=O)N1CCN(c2nc(N3CCC(N(CC)CC)CC3)nc3c(=O)n(-c4c(O)cccc4F)c(C(F)(F)F)cc23)CC1]

The synthesis of example 23 refers to example 4. $^1$H NMR (400 MHz, DMSO-d$_6$) δ 7.40-7.28 (m, 1H), 7.01 (s, 1H), 6.90-6.76 (m, 3H), 6.17 (dd, J=16.8, 2.4 Hz, 1H), 5.83-5.66 (m, 1H), 4.95-4.79 (m, 2H), 4.86 (br d, J=12.0 Hz, 1H), 3.88-3.48 (m, 8H), 3.04-2.91 (m, 4H), 2.78 (br s, 5H), 1.92 (br d, J=11.2 Hz, 2H), 1.47 (br d, J=8.8 Hz, 2H), 1.09 (br t, J=7.2 Hz, 6H); LCMS (ESI) m/z: 618.5 (M+1).

Example 24

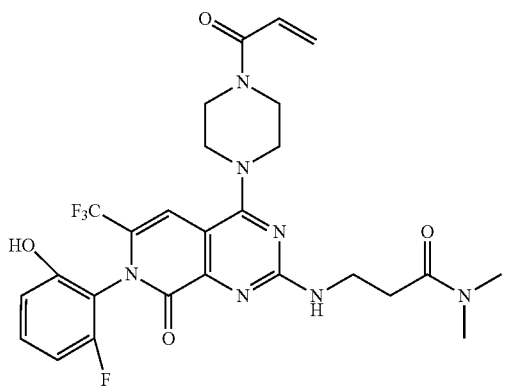 [SMILES: C=CC(=O)N1CCN(c2nc(NCCC(=O)N(C)C)nc3c(=O)n(-c4c(O)cccc4F)c(C(F)(F)F)cc23)CC1]

The synthesis of example 24 refers to example 4. $^1$H NMR (400 MHz, CDCl$_3$) δ 7.23 (br d, J=6.8 Hz, 1H), 6.93 (s, 1H), 6.80 (br d, J=7.9 Hz, 1H), 6.67 (br t, J=8.3 Hz, 1H), 6.57 (dd, J=16.8, 10.6 Hz, 1H), 6.41-6.28 (m, 1H), 5.83-5.71 (m, 1H), 3.81-3.65 (m, 9H), 3.52 (br s, 2H), 2.96-2.75 (m, 7H), 2.65-2.47 (m, 2H); LCMS (ESI) m/z: 578.4 (M+1).

Example 25

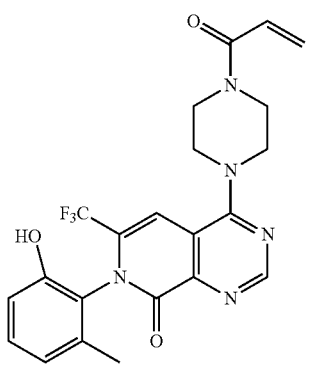 [SMILES: C=CC(=O)N1CCN(c2ncnc3c(=O)n(-c4c(C)cccc4O)c(C(F)(F)F)cc23)CC1]

The synthesis of example 25 refers to example 1 and example 20. $^1$H NMR (400 MHz, CD$_3$OD) δ 8.79 (s, 1H), 7.33-7.20 (m, 2H), 6.91-6.74 (m, 3H), 6.30 (dd, J=16.8, 2.0 Hz, 1H), 5.83 (dd, J=10.8, 2.0 Hz, 1H), 4.00 (br s, 4H), 3.91 (br s, 4H), 2.09 (s, 3H); LCMS (ESI) m/z: 460.3 (M+1).

Example 26

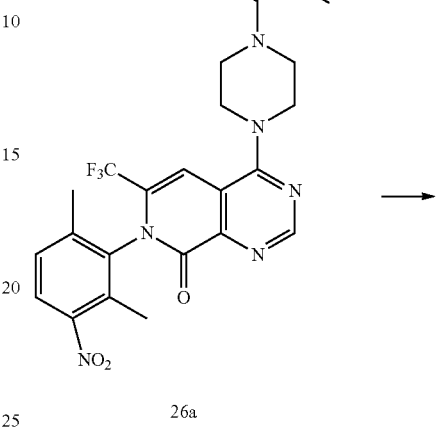

26a

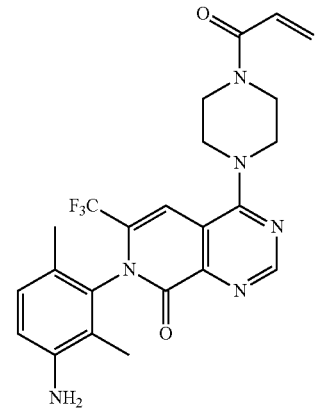

Example 26

The synthesis of compound 26a refers to example 1. LCMS (ESI) m/z: 503.2 (M+1).

The compound 26a (1.1 g, 2.19 mmol) was dissolved in ethanol (10 mL) and water (5 mL), and iron powder (611.36 g, 10.95 mmol) and ammonium chloride (1.17 g, 21.89 mmol) were added to this solution, and then stirred at 70° C. for 1 hour. LCMS showed that the target product was detected. The mixture was filtered through celite; the filter cake was washed with water (20 mL*2); the mixed filtrate was extracted with DCM (40 mL*3); and the combined organic layer was washed with saturated brine (100 mL*2), dried over anhydrous sodium sulfate (50 g), filtered, and concentrated to obtain a crude product. The product was purified by preparative HPLC (formic acid) to obtain example 26. $^1$H NMR (400 MHz, DMSO-d$_6$) δ 8.75 (s, 1H), 7.19 (s, 1H), 6.90 (d, J=8.0 Hz, 1H), 6.78 (dd, J=10.4, 16.4 Hz, 1H), 6.71 (d, J=8.0 Hz, 1H), 6.17 (dd, J=16.8, 2.0 Hz, 1H), 5.72 (dd, J=10.4, 2.0 Hz, 1H), 3.88-3.86 (m, 4H), 3.79 (br d, J=13.6 Hz, 4H), 1.82 (s, 3H), 1.72 (s, 3H); LCMS (ESI) m/z: 473.3 (M+1).

Example 27 and Example 28

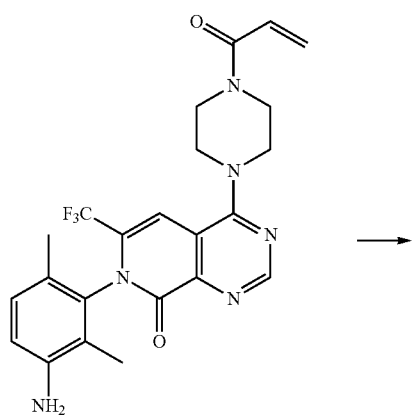

27a

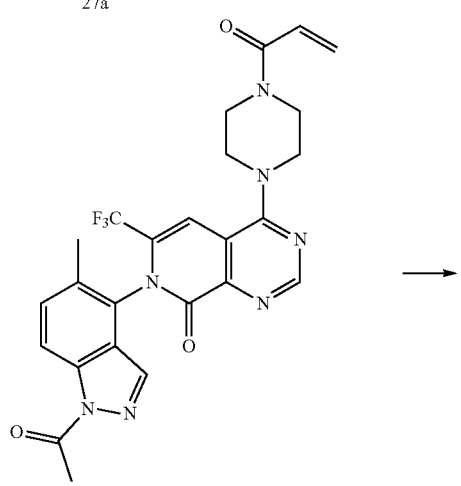

Example 27

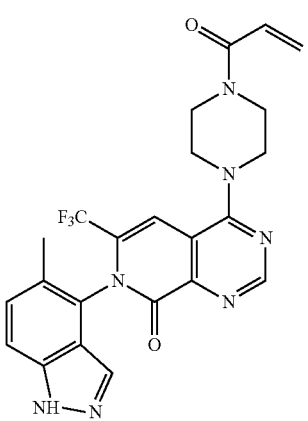

Example 28

First Step:

The compound 27a (500 mg, 8.12 mmol), acetic anhydride (209.92 mg, 2.06 mmol), 18-crown-6 (27.17 mg, 102.81 mmol) and potassium acetate (100.9 mg, 1.03 mmol) were dissolved in chloroform (10 mL), and stirred at 25° C. for 15 minutes, and then isoamyl nitrite (361.32 mg, 3.08 mmol) was added, and the mixture was stirred at 75° C. for 18 hours. LCMS showed the production of the target product; TLC (ethyl acetate:methanol=20:1) showed that the reaction was complete. The mixture was concentrated under reduced pressure to obtain a crude product, which is dissolved in ethyl acetate (30 mL) and extracted with saturated sodium bicarbonate (15 mL*3), and the combined organic layer was washed with saturated brine (20 mL*1), dried over anhydrous sodium sulfate, filtered, and concentrated to obtain a crude product. The product was purified by column chromatography (ethyl acetate:methanol=1:0 to 20:1), and the resulting residue was purified by preparative HPLC (formic acid) to obtain example 27. $^1$H NMR (400 MHz, DMSO-$d_6$) δ 8.82 (s, 1H), 8.45 (s, 1H), 8.37 (d, J=8.4 Hz, 1H), 7.70 (d, J=8.8 Hz, 1H), 7.26 (s, 1H), 6.91-6.78 (m, 1H), 6.19 (dd, J=16.8, 2.0 Hz, 1H), 5.80-5.70 (m, 1H), 3.95-3.73 (m, 8H), 2.73 (s, 3H), 2.18 (s, 3H); LCMS (ESI) m/z: 484.2 (M+1).

Second Step:

The example 27 (150 mg, 250.46 μmol) was dissolved in methanol (3 mL), and a mixed solution of hydrochloric acid solution (0.66 mL) dissolved in water (0.66 mL) was added thereto, and then stirred at 25° C. for 30 minutes. LCMS showed the production of the target product; the mixture was concentrated to obtain a crude product, which was purified by preparative HPLC (formic acid) to obtain example 28. $^1$H NMR (400 MHz, DMSO-$d_6$) δ 8.80 (s, 1H), 7.88 (s, 1H), 7.62 (d, J=8.4 Hz, 1H), 7.39 (d, J=8.4 Hz, 1H), 7.23 (s, 1H), 6.84 (dd, J=16.8, 10.4 Hz, 1H), 6.18 (dd, J=16.8, 2.4 Hz, 1H), 5.75 (dd, J=10.4, 2.0 Hz, 1H), 3.92 (br s, 4H), 3.87-3.74 (m, 4H), 2.12 (s, 3H); LCMS (ESI) m/z: 526.2 (M+1).

Example 29, Example 30 and Example 31

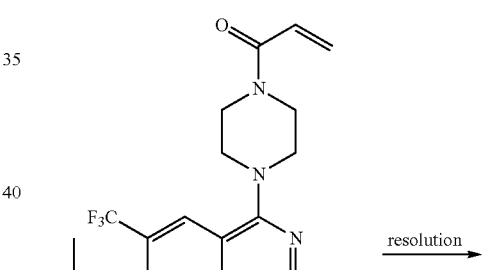

Example 29

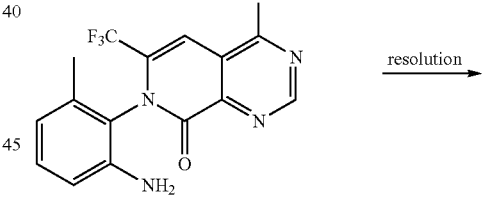

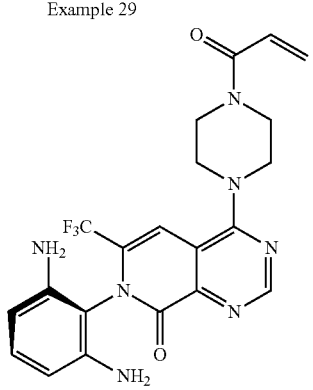

Example 30 or 31

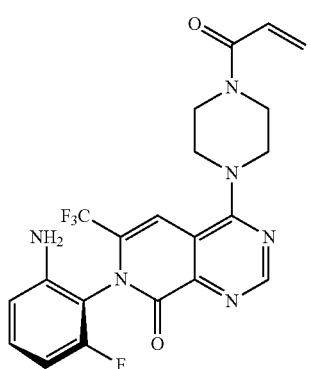

Example 31 or 30

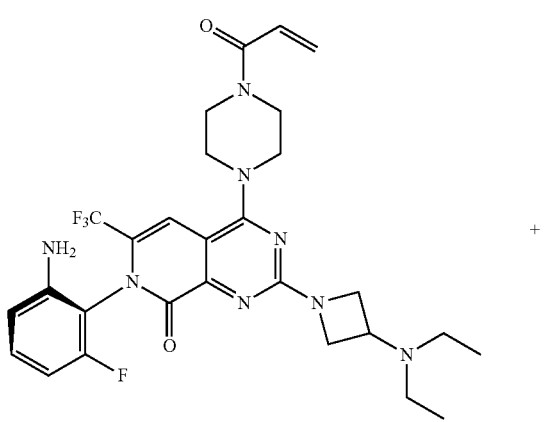

Example 32 or 33

The synthesis of example 29 refers to example 26. $^1$H NMR (400 MHz, CD$_3$OD) δ 8.78 (s, 1H), 7.28-7.16 (m, 2H), 6.83 (dd, J=16.8, 10.6 Hz, 1H), 6.66 (d, J=8.4 Hz, 1H), 6.49-6.42 (m, 1H), 6.29 (dd, J=16.8, 1.9 Hz, 1H), 5.82 (dd, J=10.6, 2.0 Hz, 1H), 4.05-3.95 (m, 4H), 3.94-3.86 (m, 4H); LCMS (ESI) m/z: 463.2 (M+1).

The example 29 was separated and purified by SFC (column model: Chiralpak AS-350×4.6 mm I.D., 3 μm; mobile phase A: methanol (containing 0.05% of diethylamine); mobile phase B: carbon dioxide; flow rate: 3 mL/min; wavelength: 220 nm) to obtain example 30 ($t_R$=1.45 min) and example 31 ($t_R$=1.76 min).

Example 30: $^1$H NMR (400 MHz, CD$_3$OD) δ 8.78 (s, 1H), 7.28-7.17 (m, 2H), 6.83 (dd, J=16.7, 10.6 Hz, 1H), 6.66 (d, J=8.4 Hz, 1H), 6.45 (t, J=8.8 Hz, 1H), 6.34-6.26 (m, 1H), 5.87-5.79 (m, 1H), 4.04-3.95 (m, 4H), 3.94-3.85 (m, 4H); LCMS (ESI) m/z: 463.2 (M+1).

Example 31: $^1$H NMR (400 MHz, CD$_3$OD) δ 8.66 (s, 1H), 7.15-7.04 (m, 2H), 6.71 (dd, J=16.8, 10.6 Hz, 1H), 6.54 (d, J=8.3 Hz, 1H), 6.33 (t, J=8.9 Hz, 1H), 6.22-6.13 (m, 1H), 5.76-5.62 (m, 1H), 3.90-3.83 (m, 4H), 3.82-3.73 (m, 4H); LCMS (ESI) m/z: 463.2 (M+1).

Example 32 and Example 33

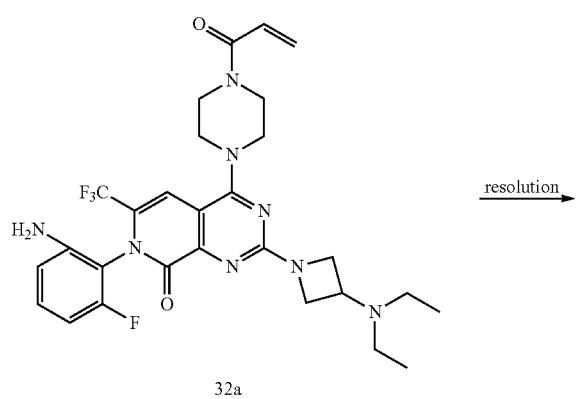

32a

→ resolution

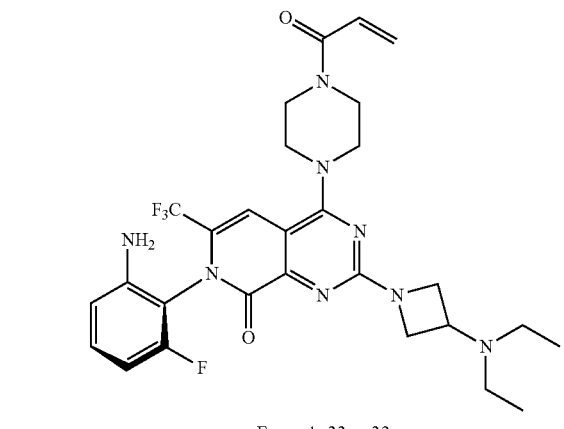

Example 33 or 32

The synthesis of compound 32a refers to example 1, example 2 and example 26. The compound 32a was separated and purified by SFC (column model: Chiralpak AS-350×4.6 mm I.D., 3 μm; mobile phase A: methanol (containing 0.05% of diethylamine); mobile phase B: carbon dioxide; flow rate: 3 mL/min; wavelength: 220 nm) to obtain example 32 ($t_R$=2.03 min) and example 33 ($t_R$=2.50 min).

Example 32: $^1$H NMR (400 MHz, CD$_3$OD) δ 7.13-6.98 (m, 2H), 6.70 (dd, J=16.8, 10.6 Hz, 1H), 6.53 (d, J=8.3 Hz, 1H), 6.32 (t, J=8.7 Hz, 1H), 6.16 (d, J=16.6 Hz, 1H), 5.70 (d, J=10.8 Hz, 1H), 4.25-4.12 (m, 2H), 4.03-3.88 (m, 2H), 3.80-3.67 (m, 8H), 3.64-3.56 (m, 1H), 2.53 (q, J=6.9 Hz, 4H), 0.96 (t, J=7.1 Hz, 6H); LCMS (ESI) m/z: 589.4 (M+1).

Example 33: $^1$H NMR (400 MHz, CD$_3$OD) δ 7.13-6.97 (m, 2H), 6.70 (dd, J=16.8, 10.6 Hz, 1H), 6.53 (d, J=8.2 Hz, 1H), 6.32 (t, J=8.8 Hz, 1H), 6.16 (d, J=16.8 Hz, 1H), 5.69 (d, J=10.6 Hz, 1H), 4.25-4.12 (m, 2H), 4.03-3.90 (m, 2H), 3.80-3.67 (m, 8H), 3.64-3.56 (m, 1H), 2.53 (q, J=6.9 Hz, 4H), 0.96 (t, J=7.0 Hz, 6H); LCMS (ESI) m/z: 589.4 (M+1).

Example 34, Example 35 and Example 36

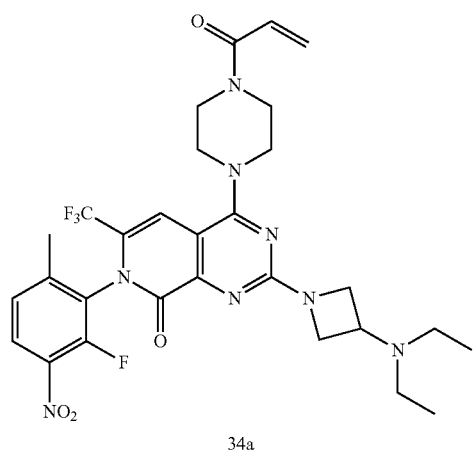

34a

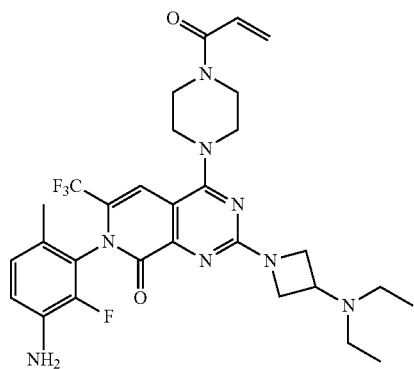

Example 34

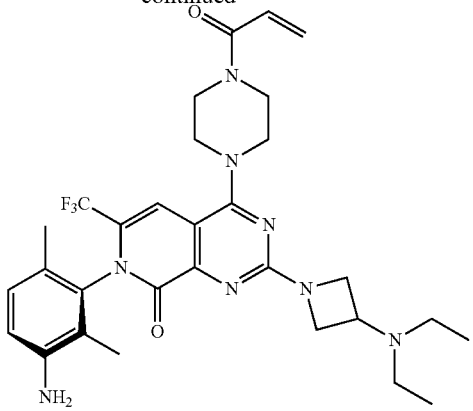

Example 36 or 35

The formate of example 34 was obtained by synthesis referring to example 2 and example 26. $^1$H NMR (400 MHz, CD$_3$OD) δ 8.50 (br s, 1H), 7.22 (s, 1H), 6.99 (d, J=8.4 Hz, 1H), 6.87-6.76 (m, 2H), 6.29 (dd, J=16.8, 2.0 Hz, 1H), 5.85-5.77 (m, 1H), 4.45-4.32 (m, 2H), 4.17 (dd, J=9.6, 5.6 Hz, 2H), 3.97-3.83 (m, 9H), 2.82 (q, J=7.2 Hz, 4H), 1.93 (s, 3H), 1.86 (s, 3H), 1.16 (t, J=7.2 Hz, 6H); LCMS (ESI) m/z: 599.2 (M+1).

The example 34 was separated and purified by SFC (column model: Chiralpak AS-350×4.6 mm I.D., 3 μm; mobile phase A: methanol (containing 0.05% of diethylamine); mobile phase B: carbon dioxide; flow rate: 3 mL/min; wavelength: 220 nm) to obtain example 35 (t$_R$=2.41 min) and example 36 (t$_R$=3.04 min).

Example 35: $^1$H NMR (400 MHz, CD$_3$OD) δ 7.22 (s, 1H), 6.99 (d, J=8.4 Hz, 1H), 6.88-6.74 (m, 2H), 6.29 (dd, J=16.8, 2.0 Hz, 1H), 5.82 (dd, J=10.8, 2.0 Hz, 1H), 4.40-4.23 (m, 2H), 4.11 (br d, J=9.6 Hz, 2H), 3.96-3.73 (m, 9H), 2.73 (br d, J=7.2 Hz, 4H), 1.93 (s, 3H), 1.86 (s, 3H), 1.18-1.16 (m, 1H), 1.18-1.08 (m, 6H); LCMS (ESI) m/z: 590.3 (M+1).

Example 36: $^1$H NMR (400 MHz, CD$_3$OD) δ 7.22 (s, 1H), 6.99 (d, J=8.4 Hz, 1H), 6.88-6.74 (m, 2H), 6.29 (dd, J=16.8, 2.0 Hz, 1H), 5.82 (dd, J=10.8, 2.0 Hz, 1H), 4.40-4.23 (m, 2H), 4.11 (br d, J=9.6 Hz, 2H), 3.96-3.73 (m, 9H), 2.73 (br d, J=7.2 Hz, 4H), 1.93 (s, 3H), 1.86 (s, 3H), 1.18-1.16 (m, 1H), 1.18-1.08 (m, 6H); LCMS (ESI) m/z: 590.3 (M+1).

Example 37

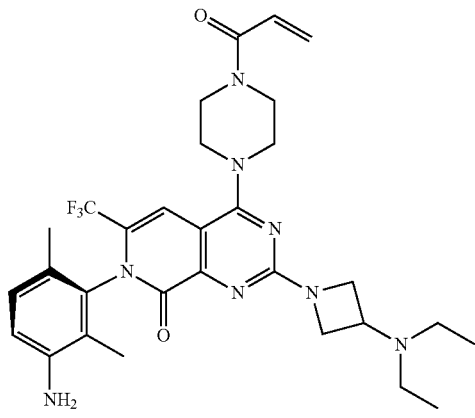

Example 35 or 36

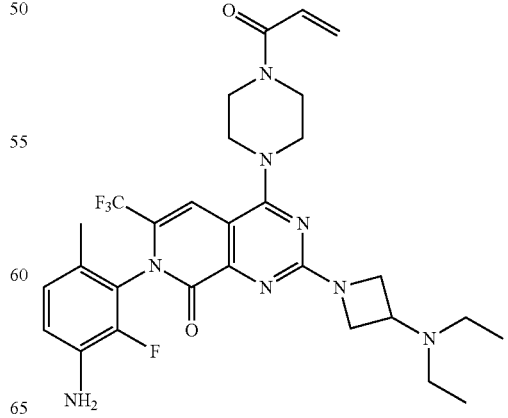

Example 34

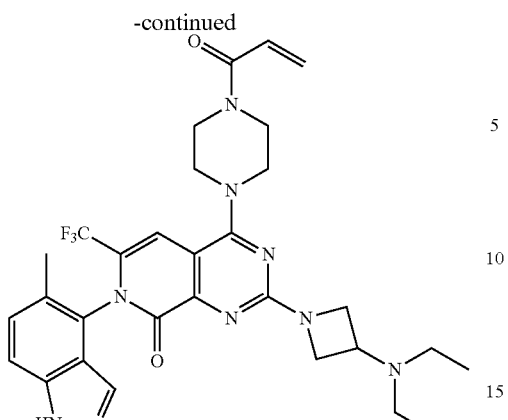

Example 37

To a solution of the example 34 (40 mg, 66.82 μmol, 1 eq) in chloroform (1 mL) was added acetic acid (12.04 mg, 200.45 μmol, 11.46 μl, 3 eq), and the resulting mixture was stirred at 0° C. for 1 hour, and then potassium acetate (1.97 mg, 20.04 μmol, 0.3 eq) and isoamyl nitrite (15.65 mg, 133.63 μmol, 17.99 μl, 2 eq) were added to the above reaction solution. The above mixture was stirred at 0° C. for 0.5 hour, and then stirred at 25° C. for 1.4 hours. TLC (dichloromethane:methanol=12:1) showed that the reaction of the raw materials was complete, and LCMS detected the MS of the target compound. The reaction solution was quenched with saturated aqueous sodium bicarbonate solution (25 mL), and then extracted with ethyl acetate (10 mL*3). The combined organic phase was washed with saturated brine (10 mL*2), dried over anhydrous sodium sulfate and then concentrated. The resulting residue was purified by preparative TLC (dichloromethane:methanol=12:1), and the resulting crude product was further purified by preparative HPLC (formic acid) to obtain example 37. $^1$H NMR (400 MHz, CD$_3$OD) δ 7.77 (s, 1H), 7.65 (d, J=8.0 Hz, 1H), 7.44 (d, J=8.8 Hz, 1H), 7.26 (s, 1H), 6.84 (dd, J=16.8, 10.8 Hz, 1H), 6.29 (dd, J=16.8, 2.0 Hz, 1H), 5.83 (dd, J=10.8, 2.0 Hz, 1H), 4.63 (br s, 4H), 4.42-4.29 (m, 2H), 4.14 (dd, J=5.2, 9.6 Hz, 2H), 3.90-3.847 (m, 9H), 2.77 (q, J=7.2 Hz, 4H), 2.20 (s, 3H), 1.13 (t, J=7.2 Hz, 6H); LCMS (ESI) m/z: 610.4 (M+1).

Example 38

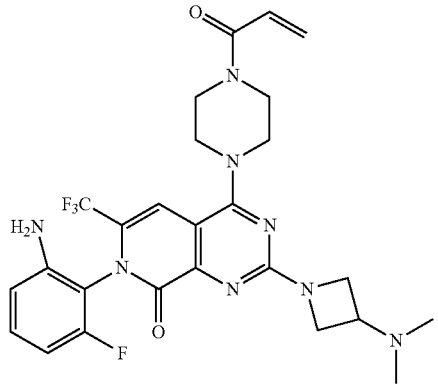 [SMILES: C=CC(=O)N1CCN(c2nc(N3CC(N(C)C)C3)nc3c(=O)n(-c4c(N)cccc4F)c(C(F)(F)F)cc23)CC1]

The formate of example 38 was obtained by synthesis referring to example 1, example 2 and example 26. $^1$H NMR (400 MHz, CD$_3$OD) δ 8.28 (br s, 1H), 7.26-7.11 (m, 2H), 6.82 (dd, J=16.8, 10.6 Hz, 1H), 6.66 (d, J=8.3 Hz, 1H), 6.45 (t, J=8.9 Hz, 1H), 6.28 (dd, J=16.7, 1.8 Hz, 1H), 5.82 (dd, J=10.6, 1.7 Hz, 1H), 4.48-4.34 (m, 2H), 4.21 (br dd, J=10.2, 4.8 Hz, 2H), 3.86 (br s, 8H), 3.78-3.66 (m, 1H), 2.59 (s, 6H); LCMS (ESI) m/z: 561.4 (M+1).

Example 39

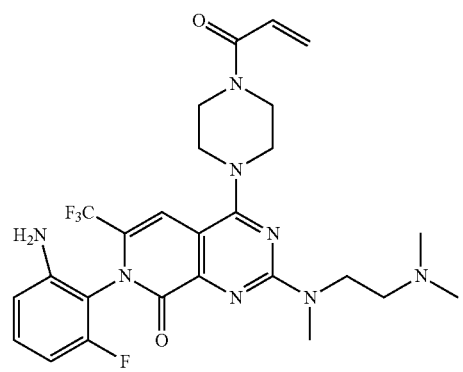 [SMILES: C=CC(=O)N1CCN(c2nc(N(C)CCN(C)C)nc3c(=O)n(-c4c(N)cccc4F)c(C(F)(F)F)cc23)CC1]

The synthesis of the formate of example 39 refers to example 1, example 2 and example 26. $^1$H NMR (400 MHz, CD$_3$OD) δ 8.43 (br s, 1H), 7.30-7.14 (m, 2H), 6.83 (dd, J=16.8, 10.6 Hz, 1H), 6.68 (br d, J=8.4 Hz, 1H), 6.47 (br t, J=8.9 Hz, 1H), 6.30 (br d, J=16.9 Hz, 1H), 5.83 (br d, J=10.7 Hz, 1H), 4.01-3.85 (m, 10H), 3.42 (br d, J=4.9 Hz, 2H), 3.35 (s, 3H), 2.92 (s, 6H); LCMS (ESI) m/z: 563.1 (M+1).

Example 40

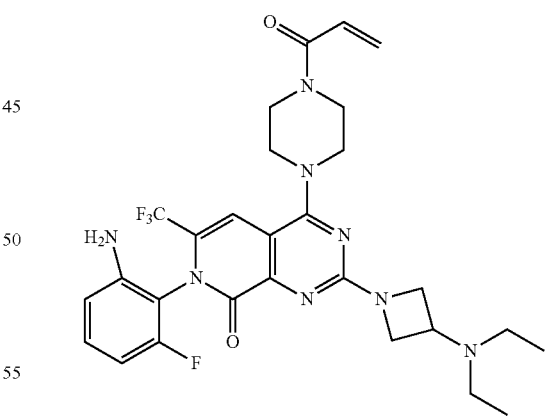

The synthesis of the formate of example 40 refers to example 2 and example 26. $^1$H NMR (400 MHz, CD$_3$OD) δ 8.43 (br s, 1H), 7.20 (s, 1H), 7.11 (t, J=7.8 Hz, 1H), 6.83 (dd, J=16.8, 10.6 Hz, 1H), 6.73 (d, J=7.5 Hz, 1H), 6.63 (d, J=7.3 Hz, 1H), 6.29 (dd, J=16.8, 1.8 Hz, 1H), 5.87-5.74 (m, 1H), 4.46-4.32 (m, 2H), 4.21 (dd, J=10.0, 5.6 Hz, 2H), 4.10-3.92 (m, 1H), 3.87 (br s, 8H), 2.93 (q, J=7.2 Hz, 4H), 1.97 (s, 3H), 1.20 (t, J=7.3 Hz, 6H); LCMS (ESI) m/z: 585.2 (M+1).

Example 41 and Example 42

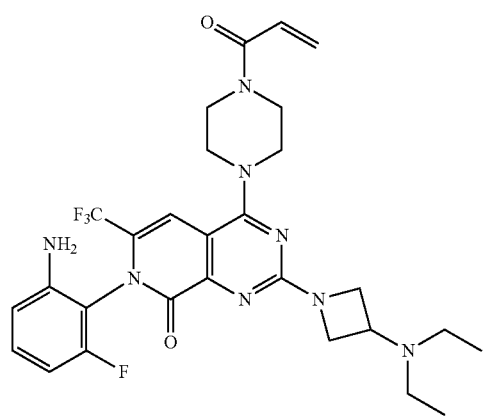

Example 32
($t_R$ = 2.03 min)

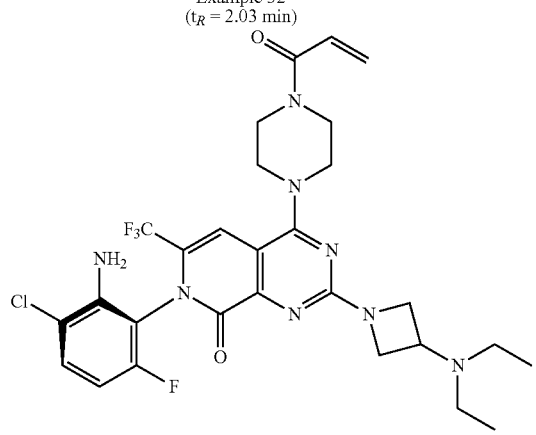

Example 41

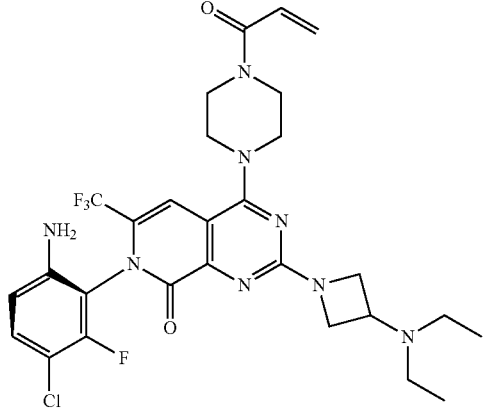

Example 42

The example 32 (102.32 mg, 164.07 μmol, 1 eq, $t_R$=2.03 min) was dissolved in acetonitrile (15 mL), and then NCS (28.48 mg, 213.29 μmol, 1.3 eq) was added thereto, and the resulting reaction solution was stirred at 70° C. for 13 hours. LCMS detected the production of the target product. The reaction was quenched by adding water (20 mL) and extracted with EtOAc (30 mL*2), and the organic phase was dried over anhydrous sodium sulfate, and then filtered and concentrated. The resulting crude product was purified by preparative HPLC (formic acid), and the resulting mixture was further purified by preparative TLC (dichloroethane:methanol=10:1) to obtain example 41 and example 42.

Example 41: $^1$H NMR (400 MHz, CD$_3$OD) δ 7.26 (dd, J=8.93, 5.62 Hz, 1H), 7.03 (s, 1H), 6.71 (dd, J=16.87, 10.64 Hz, 1H), 6.38 (t, J=8.99 Hz, 1H), 6.17 (dd, J=16.81, 1.90 Hz, 1H), 5.63-5.76 (m, 1H), 4.20 (br t, J=8.01 Hz, 2H), 3.98 (br d, J=5.50 Hz, 2H), 3.55-3.81 (m, 9H), 2.57 (q, J=7.09 Hz, 4H); 0.98 (t, J=7.15 Hz, 6H); LCMS (ESI) m/z: 623.4 (M+1).

Example 42: $^1$H NMR (400 MHz, CD$_3$OD) δ 7.14 (t, J=8.56 Hz, 1H), 7.04 (s, 1H), 6.71 (dd, J=16.75, 10.64 Hz, 1H), 6.53 (dd, J=8.99, 1.53 Hz, 1H), 6.17 (dd, J=16.75, 1.83 Hz, 1H), 5.70 (dd, J=10.64, 1.83 Hz, 1H), 4.18-4.34 (m, 2H), 3.94-4.11 (m, 2H), 2.70 (br s, 4H), 1.04 (br t, J=7.09 Hz, 6H); LCMS (ESI) m/z: 563.1 (M+1).

Example 43, Example 44 and Example 45

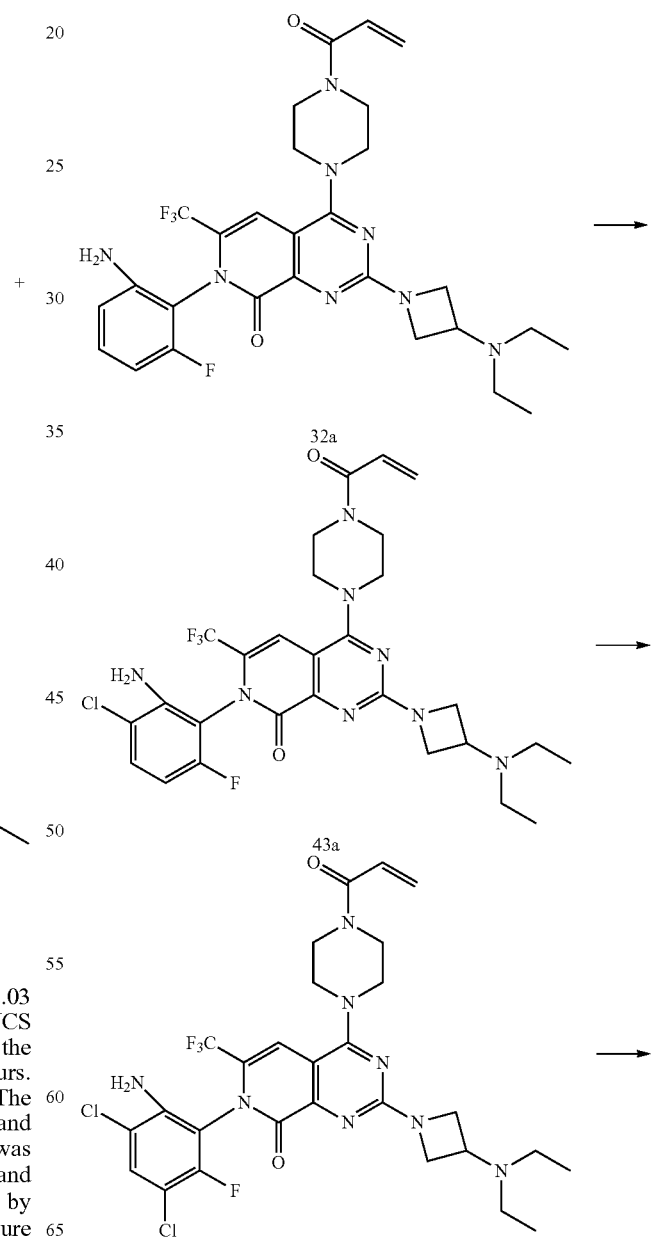

-continued

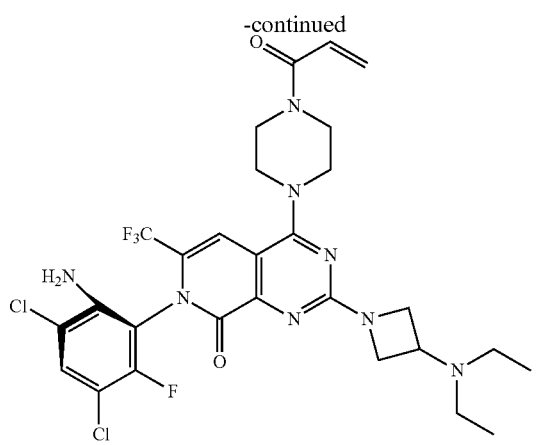

Example 44 or 45

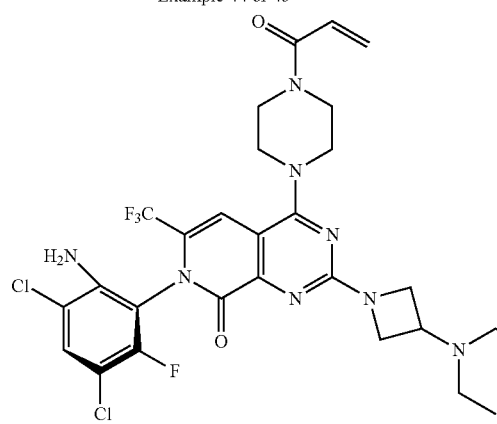

Example 44 or 45

First Step:

To a solution of the compound 32a (5.5 g, 8.67 mmol, 1 eq) in acetonitrile (70 mL) was added dropwise NCS (1.39 g, 10.41 mmol, 1.2 eq) over 30 minutes, and the resulting mixture was stirred at 80° C. for 15.5 hours. HPLC showed that 46.86% of the raw material remained and 34.22% of the target product was produced. NCS (694.75 mg, 5.201 mmol, 0.6 eq) was further added to the reaction system, and the resulting mixture was stirred at 80° C. for 2 hours. HPLC showed that 4.11% of the raw material remained and 53.36% of the target product was produced. The above reaction solution was quenched with water (20 mL); the concentrated residue was dissolved with dichloroethane (200 mL) and filtered; the filtrate was washed with water (50 mL) and dried; and the resulting crude product was purified by silica gel column chromatography (dichloroethane:methanol=50:1 to 20:1) to obtain compound 43a.

Second Step:

To a solution of the compound 43a (200 mg, 241.56 µmol, 1 eq) in acetonitrile (10 mL) was added dropwise NCS (64.51 mg, 483.11 µmol, 2 eq), and the resulting mixture was stirred at 80° C. for 1 hour. HPLC showed that there were raw materials remained. The mixture was continuously stirred at 80° C. for 12 hours. TLC (dichloroethane:methanol=10:1) showed that the reaction of the raw materials was complete, and the target product was produced. The above reaction solution was quenched with water (100 mL) and extracted with dichloromethane (40 mL*3), and the combined organic phase was washed with saturated brine (100 mL), dried over anhydrous sodium sulfate, then filtered and concentrated.

The resulting crude product was purified by preparative HPLC (formic acid) to obtain example 43. LCMS (ESI) m/z: 657.2 (M+1).

Third Step:

The example 43 was chirally resolved by SFC (column model: Cellucoat 50×4.6 mm I.D., 3 um; mobile phase A: ethanol (containing 0.1% of ammonia water) mobile phase B: carbon dioxide; flow rate: 3 mL/min; wavelength: 220 nm) to obtain example 44 ($t_R$=2.155 min) and example 45 ($t_R$=2.361 min).

Example 44: $^1$H NMR (400 MHz, CD$_3$OD) δ 7.41 (br d, J=7.2 Hz, 1H), 7.04 (s, 1H), 6.70 (dd, J=16.8, 10.6 Hz, 1H), 6.16 (d, J=16.4 Hz, 1H), 5.69 (d, J=10.4 Hz, 1H), 4.17 (d, J=7.6 Hz, 2H), 3.97 (s, 2H), 3.73 (d, J=8.8 Hz, 8H), 3.65-3.54 (m, 1H), 2.53 (q, J=7.2 Hz, 4H), 0.96 (br t, J=7.2 Hz, 6H); LCMS (ESI) m/z: 657.2 (M+1).

Example 45: $^1$H NMR (400 MHz, CD$_3$OD) δ 7.41 (br d, J=7.2 Hz, 1H), 7.04 (s, 1H), 6.70 (dd, J=16.8, 10.6 Hz, 1H), 6.16 (d, J=16.4 Hz, 1H), 5.69 (d, J=10.8 Hz, 1H), 4.18 (d, J=7.6 Hz, 2H), 3.97 (s, 2H), 3.73 (d, J=8.8 Hz, 8H), 3.65-3.54 (m, 1H), 2.53 (q, J=7.2 Hz, 4H), 0.96 (br t, J=7.2 Hz, 6H); LCMS (ESI) m/z: 657.2 (M+1).

Example 46

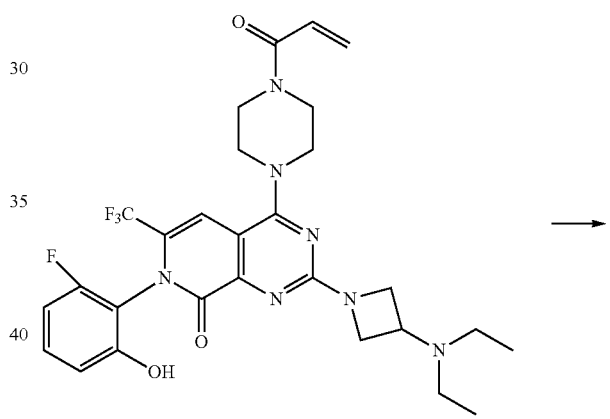

Example 8

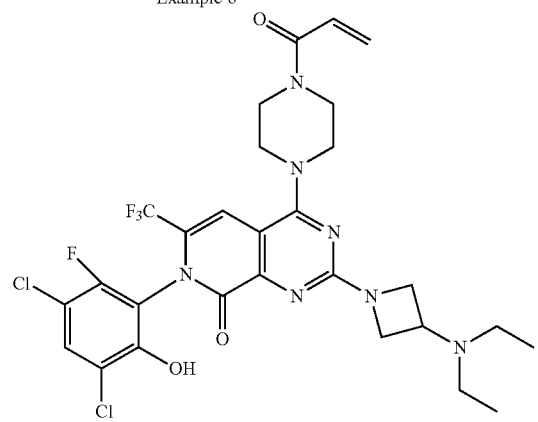

Example 46

To a solution of the example 8 (400 mg, 678.45 µmol, 1 eq) in acetic acid (10 mL) was added dropwise NCS (181.19 mg, 1.36 mmol, 2 eq), and the resulting mixture was stirred at 15° C. for 3 hours. LC-MS showed that there were raw materials remained and there was target product produced.

TLC (dichloroethane:methanol=10:1) showed that the reaction of the raw materials was complete, and three new spots were generated. The above reaction solution was quenched with saturated aqueous sodium bicarbonate solution (500 mL) and extracted with ethyl acetate (30 mL*3); the organic phase was washed with saturated brine (50 mL*2) and dried over anhydrous sodium sulfate; the resulting mixture was purified by preparative TLC (dichloroethane:methanol=10:1); and the resulting crude product was further purified by preparative HPLC (formic acid) to obtain example 46. LCMS (ESI) m/z: 658.0 (M+1).

Example 47 and Example 48

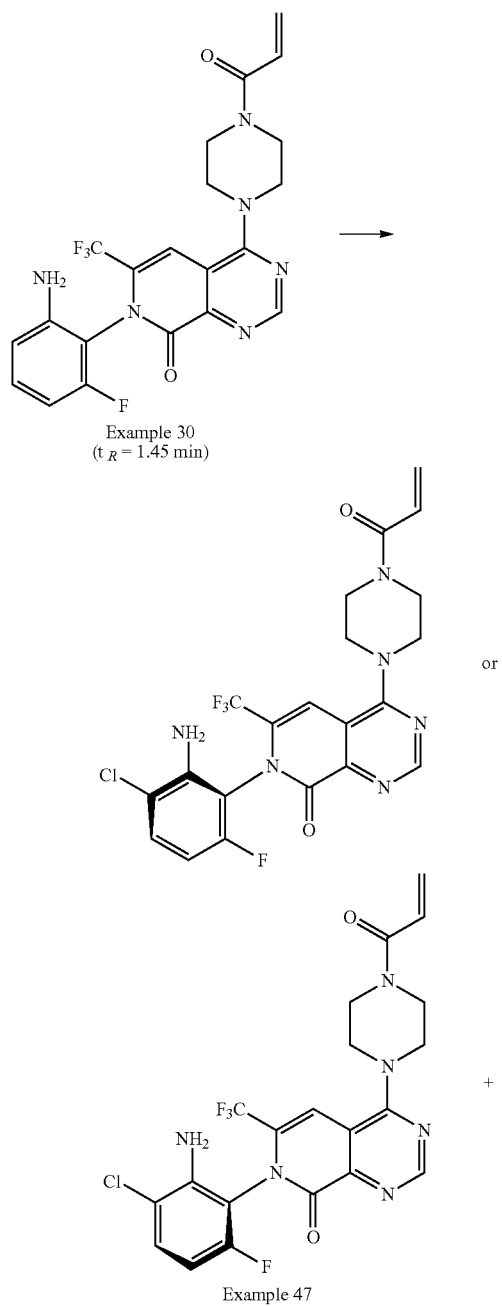

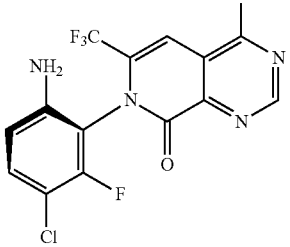

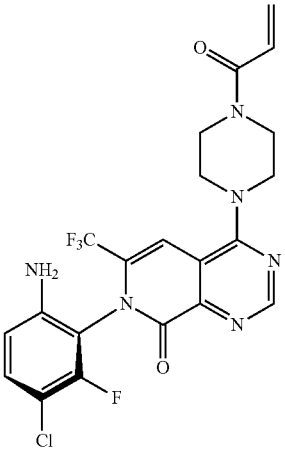

Example 48

To a solution of the example 30 (150 mg, 316.04 μmol, 1 eq, $t_R$=1.45 min) in acetonitrile (8 mL) was added NCS (33.76 mg, 252.83 μmol, 0.8 eq) under the protection of nitrogen, and the resulting mixture was stirred at 70° C. for 1 hour. LC-MS showed that the target product was produced, and TLC showed that new spots were generated. The above reaction solution was poured into water (30 mL); the aqueous phase was extracted with dichloromethane (50 mL*3); the resulting combined organic layer was washed with saturated brine (20 mL), dried over anhydrous sodium sulfate (30 g), then filtered and concentrated. The resulting residue was purified by preparative TLC (dichloromethane:methanol=12:1), and the resulting crude product was further purified by preparative HPLC (formic acid) to obtain example 47 and example 48.

Example 47: $^1$HNMR (400 MHz, CD$_3$OD) δ 8.66 (s, 1H), 7.28 (dd, J=5.6, 8.9 Hz, 1H), 7.16 (s, 1H), 6.71 (dd, J=16.8, 10.6 Hz, 1H), 6.40 (t, J=9.0 Hz, 1H), 6.17 (dd, J=16.8, 1.2 Hz, 1H), 5.76-5.64 (m, 1H), 3.92-3.84 (m, 4H), 3.82-3.73 (m, 4H); LCMS (ESI) m/z: 497.3 (M+1).

Example 48: $^1$HNMR (400 MHz, CD$_3$OD) δ 8.78 (br s, 1H), 7.35-7.20 (m, 2H), 6.83 (br dd, J=16.8, 11.4 Hz, 1H), 6.66 (br d, J=8.2 Hz, 1H), 6.29 (br d, J=16.9 Hz, 1H), 5.82 (br d, J=10.3 Hz, 1H), 4.06-3.95 (m, 4H), 3.94-3.82 (m, 4H); LCMS (ESI) m/z: 497.1 (M+1).

Example 49

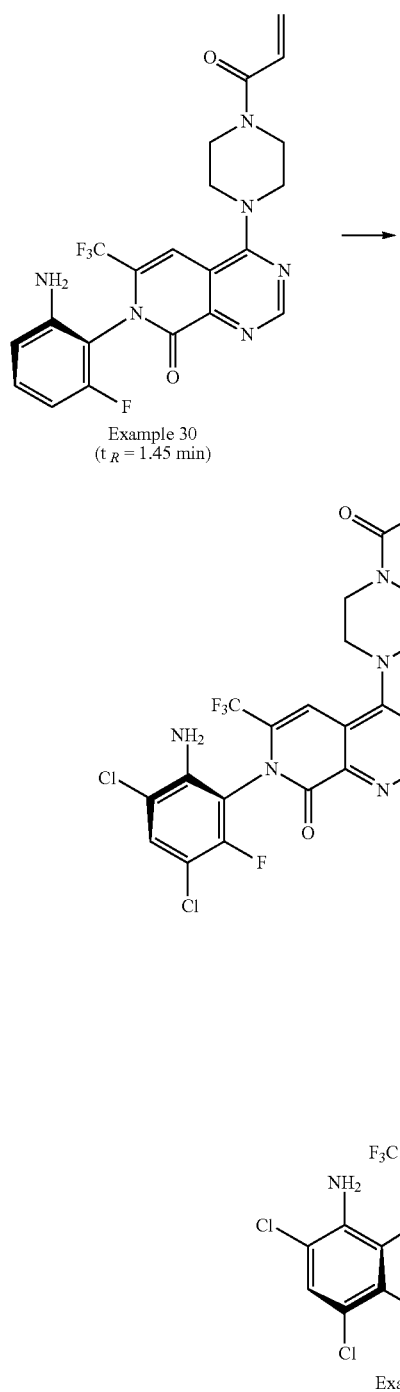

Example 50

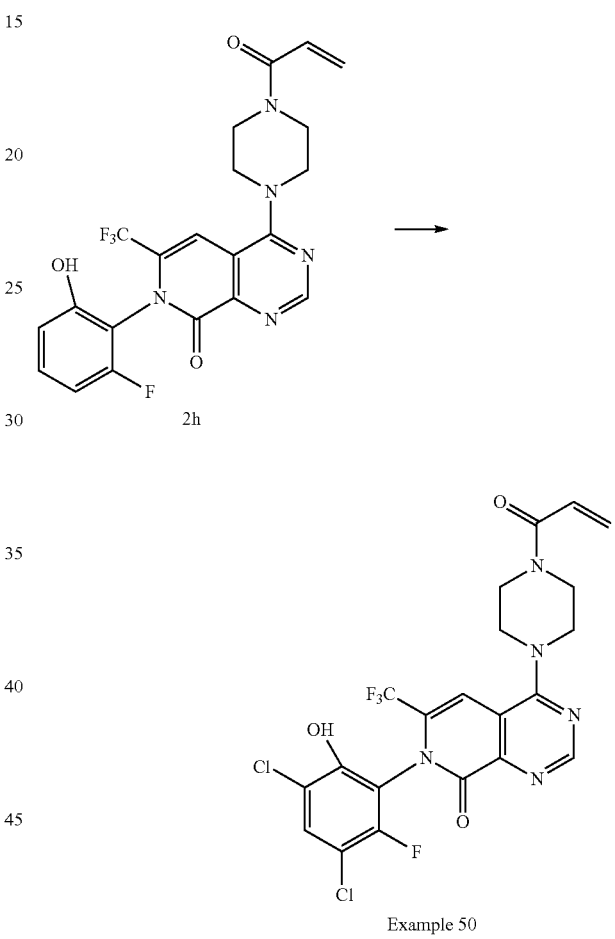

Under the protection of nitrogen, to a solution of the example 30 or 31 (100 mg, 210.69 µmol, 1 eq, $t_R$=1.45 min) in acetonitrile (5 mL) was added NCS (28.13 mg, 210.69 µmol, 1 eq), and the resulting mixture was stirred at 15° C. for 2 hours. LC-MS showed that the reaction of the raw materials was not complete. Then the mixture was stirred at 70° C. for 2 hours. LC-MS showed that the product was detected. The above reaction solution was poured into water (30 mL); the aqueous phase was extracted with dichloromethane (50 mL*3); the resulting combined organic layer was washed with saturated brine (20 mL), dried over anhydrous sodium sulfate (30 g), then filtered and concentrated. The resulting residue was purified by preparative HPLC (formic acid) to obtain example 49. $^1$HNMR (400 MHz, CD$_3$OD) δ 8.80 (s, 1H), 7.56 (br d, J=7.2 Hz, 1H), 7.30 (s, 1H), 6.83 (br dd, J=16.6, 10.6 Hz, 1H), 6.30 (br d, J=16.6 Hz, 1H), 5.83 (br d, J=10.6 Hz, 1H), 4.06-3.95 (m, 4H), 3.95-3.83 (m, 4H); LCMS (ESI) m/z: 531.2 (M+1).

The compound 2h (800 mg, 1.73 mmol, 1 eq) was dissolved in acetic acid (30 mL), and then NCS (691.59 mg, 5.18 mmol, 3 eq) was added thereto, and the resulting reaction solution was stirred at 25° C. for 36 hours. LCMS detected the production of the target product. The reaction was quenched by adding water (100 mL) and extracted with ethyl acetate (200 mL), and the organic phase was washed successively with water (100 mL*3), saturated brine (100 mL) and saturated aqueous sodium bicarbonate solution (100 mL), dried over anhydrous sodium sulfate, then filtered and concentrated. The resulting crude product was separated by preparative HPLC (formic acid) to obtain example 50. $^1$H NMR (400 MHz, DMSO-d$_6$) δ 11.37 (br s, 1H), 8.90-8.73 (m, 1H), 7.96 (br s, 1H), 7.22 (s, 1H), 6.83 (dd, J=16.7, 10.5 Hz, 1H), 6.18 (dd, J=16.8, 2.3 Hz, 1H), 5.85-5.62 (m, 1H), 3.99-3.70 (m, 8H); LCMS (ESI) m/z: 532.2 (M+1).

Example 51 and Example 52

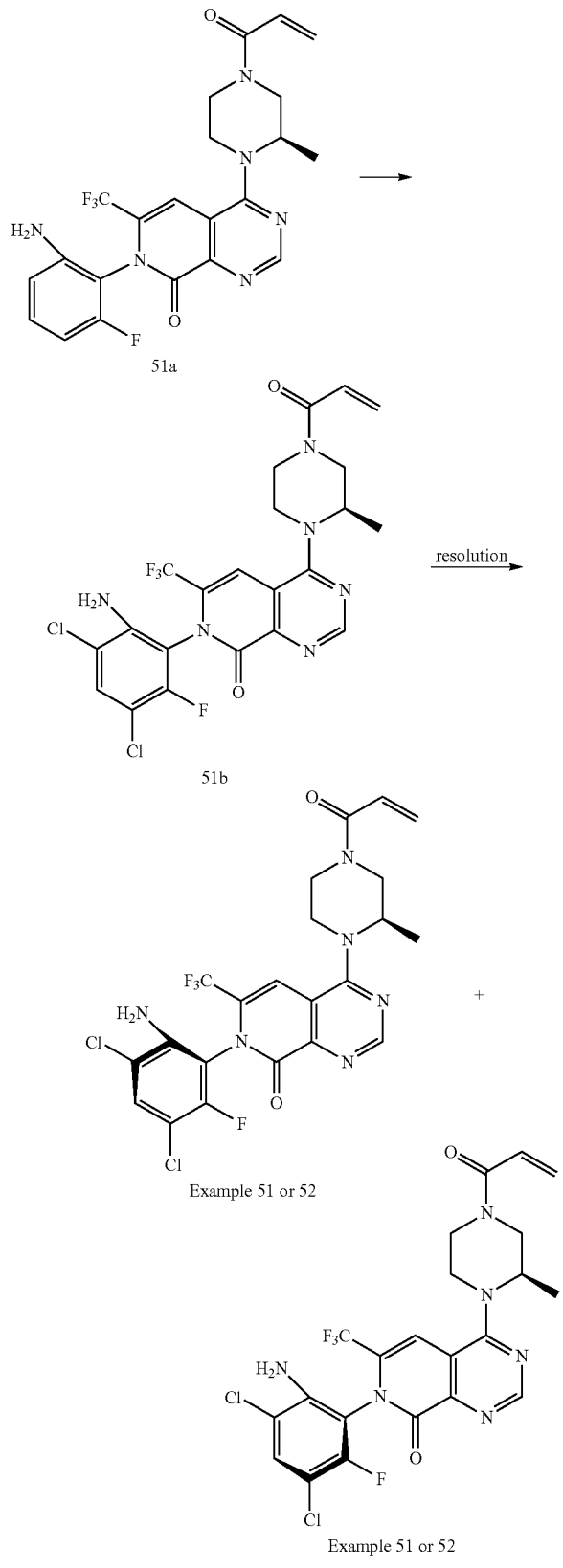

First Step:

The synthesis of compound 51a refers to example 29. LCMS (ESI) m/z: 477.1 (M+1).

Second Step:

To a solution of the compound 51a (340 mg, 713.65 μmol, 1 eq) in acetonitrile (10 mL) was added NCS (200.12 mg, 1.50 mmol, 2.1 eq), and the resulting mixture was heated to 90° C. for 2 hours. LC-MS and HPLC showed that the conversion of raw materials was complete, and detected the production of the target product. The reaction was quenched by adding saturated aqueous sodium bicarbonate solution (50 mL) and extracted with ethyl acetate (30 mL*3), and the organic phase was washed with saturated brine (50 mL), dried over anhydrous sodium sulfate, then filtered and concentrated. The resulting crude product was separated by preparative HPLC (formic acid) to obtain compound 51b. LCMS (ESI) m/z: 545.3 (M+1).

Third Step:

The compound 51b was chirally resolved by SFC (column model: DAICEL CHIRALPAK AS (250 mm*30 mm, 10 um; mobile phase A: ethanol (containing 0.1% of ammonia water); mobile phase B: carbon dioxide) to obtain example 51 ($t_R$=1.569 min) and example 52 ($t_R$=2.350 min).

Example 51: $^1$H NMR (400 MHz, CD$_3$OD) δ 8.68 (s, 1H), 7.44 (d, J=7.2 Hz, 1H), 7.07 (s, 1H), 6.81-6.58 (m, 1H), 6.19 (br dd, J=16.8, 6.4 Hz, 1H), 5.71 (br d, J=10.6 Hz, 1H), 4.70-4.64 (m, 1H), 4.53-3.90 (m, 3H), 3.72-3.34 (m, 2H), 3.17-2.95 (m, 1H), 1.33 (br s, 3H); LCMS (ESI) m/z: 545.1 (M+1).

Example 52: $^1$H NMR (400 MHz, CD$_3$OD) δ 8.8 (s, 1H), 7.44 (d, J=7.2 Hz, 1H), 7.07 (s, 1H), 6.81-6.46 (m, 1H), 6.19 (br d, J=16.4 Hz, 1H), 5.71 (dd, J=10.8, 1.2 Hz, 1H), 4.64 (br s, 1H), 4.51-4.24 (m, 1H), 4.26-3.84 (m, 2H), 3.68-3.36 (m, 2H), 3.17-2.95 (m, 1H), 1.34 (br s, 3H); LCMS (ESI) m/z: 545.1 (M+1).

Example 53 and Example 54

111

-continued

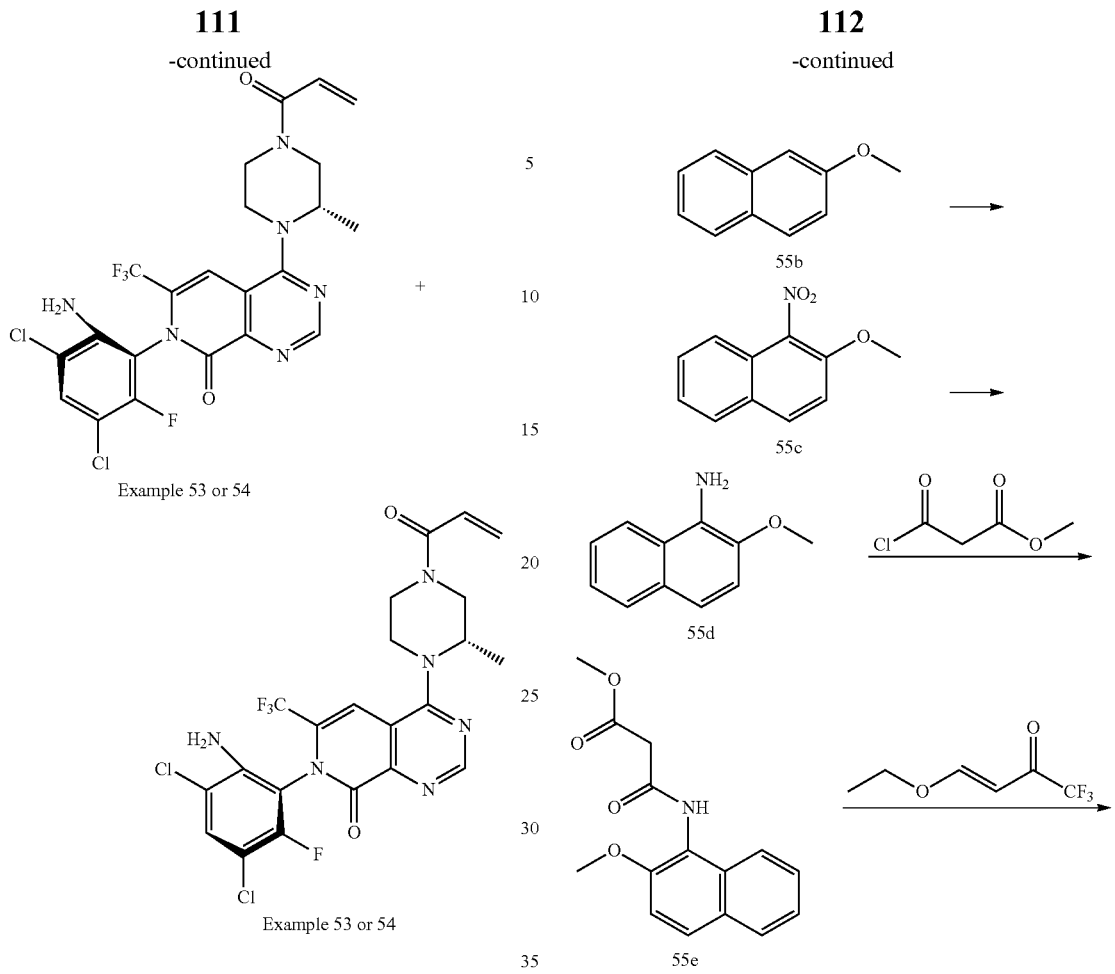

Example 53 or 54

Example 53 or 54

First Step:
The synthesis of compound 53a refers to that of compound 51b.

Second Step:
The compound 53a was chirally resolved by SFC (column model: DAICEL CHIRALPAK AS (250 mm*30 mm, 10 um; mobile phase A: ethanol (containing 0.1% of ammonia water); mobile phase B: carbon dioxide) to obtain example 53 ($t_R$=1.429 min) and example 52 ($t_R$=2.028 min).

Example 53: $^1$H NMR (400 MHz, $CD_3OD$) δ 8.79 (s, 1H), 7.56 (br d, J=7.2 Hz, 1H), 7.19 (s, 1H), 6.97-6.70 (m, 1H), 6.31 (br d, J=16.0 Hz, 1H), 5.83 (br d, J=10.4 Hz, 1H), 4.75 (br s, 1H), 4.62-4.27 (m, 2H), 4.26-3.97 (m, 1H), 3.79-3.48 (m, 2H), 3.30-3.09 (m, 1H), 1.46 (br s, 3H); LCMS (ESI) m/z: 545.1 (M+1).

Example 54: $^1$H NMR (400 MHz, $CD_3OD$) δ 8.80 (s, 1H), 7.56 (d, J=7.2 Hz, 1H), 7.20 (s, 1H), 6.93-6.71 (m, 1H), 6.31 (br dd, J=6.0, 16.4 Hz, 1H), 5.83 (dd, J=10.4, 1.7 Hz, 1H), 4.82-4.77 (m, 1H), 4.61-4.24 (m, 2H), 4.22-4.02 (m, 1H), 3.83-3.48 (m, 2H), 3.30-3.12 (m, 1H), 1.45 (br d, J=5.2 Hz, 3H); LCMS (ESI) m/z: 545.1 (M+1).

Example 55

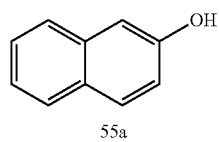

55a

112

-continued

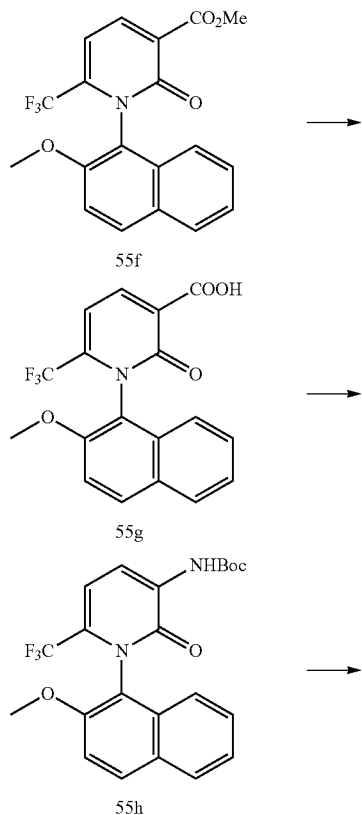

113
-continued
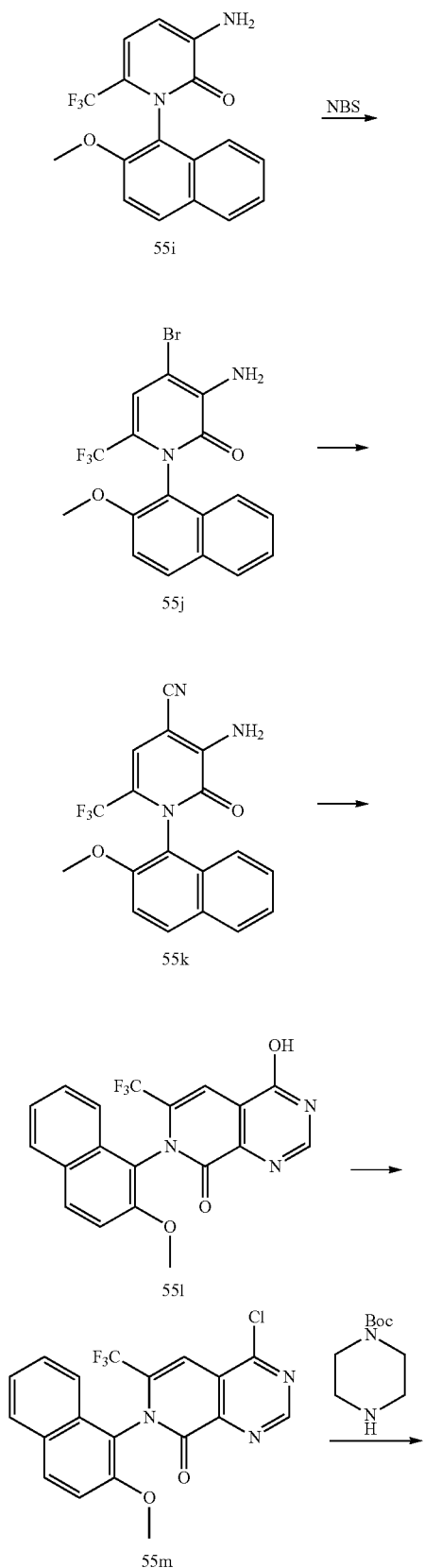
114
-continued
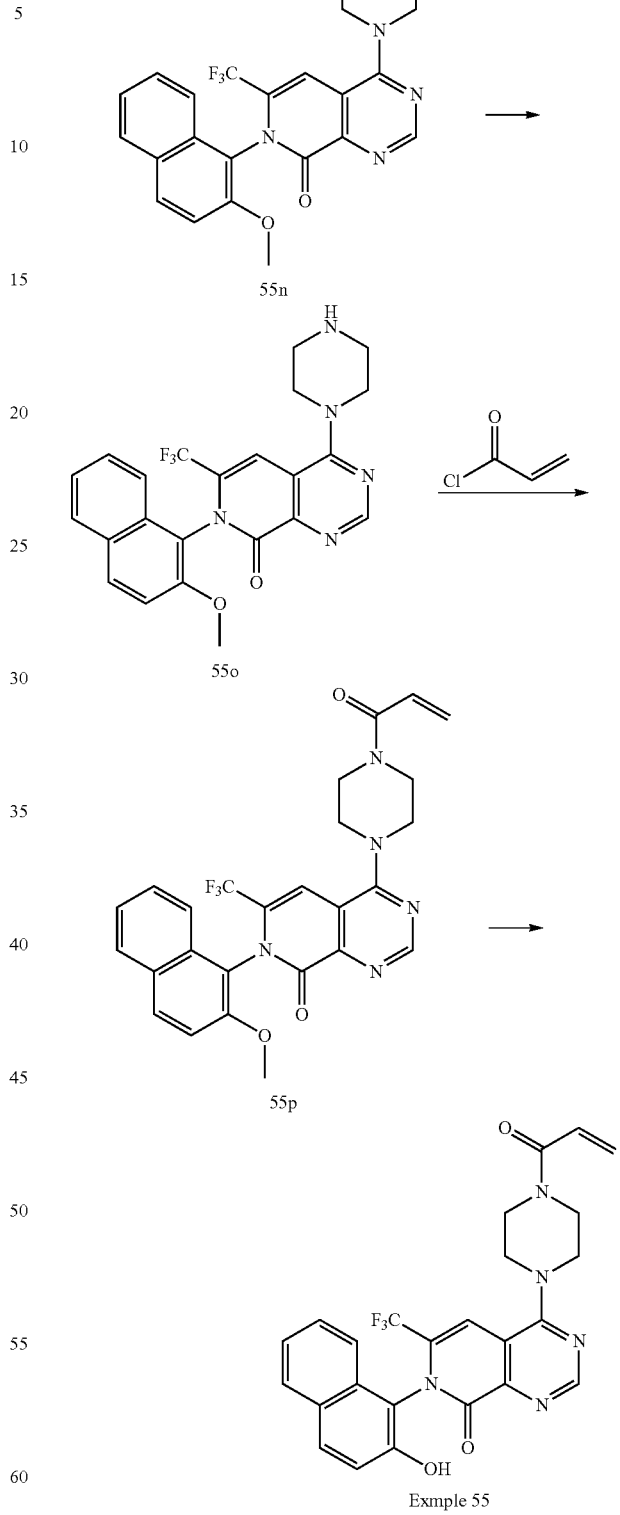
First Step:
The compound 55a (20 g, 138.73 mmol, 57.14 mL, 1 eq) was dissolved in THF (200 mL), sodium hydride (11.10 g, 277.45 mmol, purity: 60%, 2 eq) was added thereto at 0° C., stirred at 0° C. for 30 minutes, and then methyl iodide (29.54 g, 208.09 mmol, 12.95 mL, 1.5 eq) was added, and the resulting mixture was continued to react at 25° C. for 18 hours. LC-MS showed that a small amount of raw materials remained, and the target product was produced. Water (200 mL) was added to the reaction system, which was extracted with ethyl acetate (300 mL*3). The organic phases were combined, dried over anhydrous sodium sulfate, and concentrated under reduced pressure to obtain a crude compound 55b. LCMS (ESI) m/z: 159.0 (M+1); $^1$H NMR (400 MHz, CDCl$_3$) δ 7.92-7.85 (m, 3H), 7.59-7.54 (m, 1H), 7.50-7.44 (m, 1H), 7.32-7.25 (m, 2H), 4.05 (s, 3H). LCMS (ESI) m/z: 159.0 (m+1).

Second Step:

The compound 55b (10 g, 63.21 mmol, 1 eq) was dissolved in acetic anhydride (100 mL), and concentrated nitric acid (6.37 g, 101.14 mmol, 4.55 mL, 1.6 eq) was added dropwise thereto at 0° C.; after the dropwise addition was completed, the reaction system was cooled to 0° C. and stirred for 1 hour. TLC (petroleum ether:ethyl acetate=5:1) showed that the reaction of the raw materials was complete. The reactant was poured into saturated sodium bicarbonate solution (1 L), and extracted with ethyl acetate (500 mL*3). The organic phases were combined and concentrated under reduced pressure, and the resulting residue was purified by silica gel column chromatography (silicon oxide, ethyl acetate:petroleum ether=1:10) to obtain compound 55c. $^1$H NMR (400 MHz, CDCl$_3$) δ 7.97 (d, J=9.17 Hz, 1H), 7.85 (d, J=8.31 Hz, 1H), 7.73-7.67 (m, 1H), 7.65-7.57 (m, 1H), 7.51-7.43 (m, 1H), 7.35 (d, J=9.17 Hz, 1H), 4.04 (s, 3H).

Third Step:

The compound 55c (3 g, 14.76 mmol, 1 eq) was dissolved in a mixed solution of ethanol (40 mL) and water (20 mL), ammonium chloride (7.9 g, 147.64 mmol, 10 eq) and iron powder (8.25 g, 147.64 mmol, 10 eq) were added thereto, and stirred at 90° C. for 2 hours. LCMS showed that the reaction was complete, and detected the target product. The reaction system was filtered and concentrated under reduced pressure to obtain compound 55d. LCMS (ESI) m/z: 174.0 (M+1).

Fourth Step:

The compound 55d (2.5 g, 14.43 mmol, 1 eq) and potassium carbonate (5.98 g, 43.30 mmol, 3 eq) were dissolved in acetonitrile (50 mL), and monomethyl malonyl chloride (2.96 g, 21.65 mmol, 2.31 mL, 1.5 eq) was added thereto at 0° C., and stirred at 25° C. for 12 hours. LCMS showed that some raw materials remained; additional monomethyl malonyl chloride (2.96 g, 21.65 mmol, 2.31 mL, 1.5 eq) was added, and continuously stirred at 25° C. for 2 hours. LCMS showed that the reaction was complete, and detected the production of the product. The reaction was quenched by adding water (100 mL) and extracted with ethyl acetate (100 mL*3), and the organic phases were combined, dried over anhydrous sodium sulfate, and concentrated under reduced pressure. The concentrated crude product was slurried (ethyl acetate:petroleum ether=1:1, 12 mL) for 2 hours and filtered, and the filter cake was dried under reduced pressure. Compound 55e was thereby obtained. LCMS (ESI) m/z: 274.0 (M+1).

Fifth Step:

The compound 55e (3.8 g, 11.19 mmol, 1 eq) was dissolved in methanol (50 mL), and 4-ethoxy-1, 1, 1-trifluoro-3-buten-2-one (2.82 g, 16.79 mmol, 2.39 mL, 1.5 eq) and sodium methoxide (907.01 mg, 16.79 mmol, 1.5 eq) were added thereto, and the reaction system was stirred at 90° C. for 12 hours. LCMS showed that there were raw materials remained; the reaction system was continuously stirred at 90° C. for 6 hours. LCMS showed that there were still raw materials remained; additional 4-ethoxy-1, 1, 1-trifluoro-3-buten-2-one (940.89 mg, 5.60 mmol, 797.36 µl, 0.5 eq) and sodium methoxide (302.36 mg, 5.60 mmol, 0.5 eq) were added, and the reaction system was stirred at 90° C. for 15 hours. LCMS showed that the reaction was complete, and detected the production of the product. The reaction system was concentrated under reduced pressure, and saturated aqueous ammonium chloride solution (100 mL) was added thereto, and extracted with ethyl acetate (100 mL*2). The organic phases were combined and concentrated under reduced pressure to obtain a crude compound 55f. LCMS (ESI) m/z: 378.1 (M+1).

Sixth Step:

The compound 55f (4.6 g, 12.19 mmol, 1 eq) was dissolved in a mixed solvent of water (30 mL) and THF (30 mL), and lithium hydroxide monohydrate (1.02 g, 24.38 mmol, 2 eq) was added thereto, and stirred at 25° C. for 16 hours. LCMS showed that the reaction was complete, and detected the production of the target product. The reaction was quenched by adding water (100 mL), adjusted to pH 2 by adding diluted hydrochloric acid (1M), and extracted with ethyl acetate (200 mL*3). The organic phases were combined, dried over anhydrous sodium sulfate, and concentrated under reduced pressure to obtain a crude compound 55g. LCMS (ESI) m/z: 363.9 (M+1).

Seventh Step:

The compound 55g (4.4 g, 12.11 mmol, 1 eq) was dissolved in t-butanol (50 mL), and triethylamine (2.45 g, 24.22 mmol, 3.37 mL, 2 eq) and 4A molecular sieve (4 g) were added thereto, and the resulting mixture was stirred at 90° C. for 1 hour. Subsequently, DPPA (3.50 g, 12.72 mmol, 2.76 mL, 1.05 eq) was added and stirred at 90° C. for 1 hour. LCMS showed that the reaction was complete, and detected the target product. After filtration, the filtrate was concentrated under reduced pressure, and the resulting crude product was purified by silica gel column chromatography (silicon oxide, petroleum ether:ethyl acetate=10:1) to obtain compound 55h. LCMS (ESI) m/z: 379.1 (M+1-56); $^1$H NMR (400 MHz, CDCl$_3$-d) δ 8.14 (br d, J=7.70 Hz, 1H), 8.01 (d, J=9.05 Hz, 1H), 7.79-7.88 (m, 2H), 7.42-7.48 (m, 1H), 7.34-7.40 (m, 2H), 7.21 (d, J=8.56 Hz, 1H), 6.93 (d, J=7.95 Hz, 1H), 3.91 (s, 3H), 1.52 (s, 9H).

Eighth Step:

The compound 55h (300 mg, 690.60 µmol, 1 eq) was dissolved in 1,4-dioxane (4 mL), and hydrogen chloride/1, 4-dioxane solution (4M, 4 mL, 23.17 eq) was added thereto, then stirred at 25° C. for 12 hours. LCMS showed that some raw materials remained; the stirring was performed at the temperature raised to 45° C. for 2 hours. LCMS showed that few raw materials remained, and detected the production of the target product. The reaction solution was directly concentrated under reduced pressure, and further dissolved with ethyl acetate (10 mL). The organic phase was washed with saturated sodium bicarbonate solution (10 mL*2), and the resulting organic phase was concentrated under reduced pressure to obtain a crude compound 55i. LCMS (ESI) m/z: 335.1 (M+1).

Ninth Step:

The compound 55i (1.2 g, 3.59 mmol, 1 eq) was dissolved in DCM (20 mL), and bromosuccinimide (638.90 mg, 3.59 mmol, 1 eq) was added thereto at 0° C., and continuously stirred for 0.5 hour. TLC (petroleum ether:ethyl acetate=3:1) showed that the reaction was complete, and a new spot was generated. The reaction was quenched by adding saturated sodium sulfite solution (50 mL), and extracted with ethyl acetate (50 mL*2). The organic phases were combined and concentrated under reduced pressure, and the resulting residue was purified by silica gel column chromatography (silicon oxide, petroleum ether:ethyl acetate=5:1) to obtain compound 55j. $^1$H NMR (400 MHz, CDCl$_3$) δ 8.01 (d, J=9.05 Hz, 1H), 7.85 (d, J=8.19 Hz, 1H), 7.49-7.42 (m, 1H), 7.41-7.33 (m, 2H), 7.25 (d, J=8.44 Hz, 1H), 7.03 (s, 1H), 5.02 (br s, 2H), 3.92 (s, 3H).

Tenth Step:

Under the protection of nitrogen, the compound 55j (850 mg, 2.06 mmol, 1 eq) was dissolved in N,N-dimethylacetamide (20 mL), and zinc powder (1.75 g, 26.74 mmol), Pd$_2$(dba)$_3$ (376.76 mg, 411.43 μmol, 0.2 eq), 1,1'-bis(diphenylphosphine)ferrocene (456.18 mg, 822.87 μmol, 0.4 eq) and zinc cyanide (966.25 mg, 8.23 mmol, 522.30 μl, 4 eq) were added thereto and heated to 120° C. and stirred for 16 hours. LCMS showed that the reaction was complete, and detected the target product. The reaction solution was filtered, and ethyl acetate (50 mL) was added thereto and washed with water (50 mL*2). The organic phase was concentrated under reduced pressure, and the resulting residue was purified by silica gel column chromatography (silicon oxide, petroleum ether:ethyl acetate=4:1) to obtain a crude compound 55k. LCMS (ESI) m/z: 360.2 (M+1); $^1$H NMR (400 MHz, CDCl$_3$) δ 8.02 (d, J=9.17 Hz, 1H), 7.86 (d, J=8.07 Hz, 1H), 7.51-7.44 (m, 1H), 7.43-7.35 (m, 2H), 7.23 (d, J=8.44 Hz, 1H), 6.85 (s, 1H), 5.78 (br, s, 2H), 3.92 (s, 3H).

Eleventh Step:

The compound 55k (880 mg, 2.45 mmol, 1 eq) was dissolved in formic acid (10 mL), and concentrated sulfuric acid (1.20 g, 12.25 mmol, 652.75 μl, 5 eq) was added thereto and stirred at 100° C. for 1 hour. LCMS showed that the reaction was complete, and detected the production of the target product. The reaction solution was poured into ice water (100 mL) and filtered, and the filter cake was dried under reduced pressure. The filter cake was slurried (petroleum ether:ethyl acetate=1:1, 10 mL) for 1 hour and filtered, and the filter cake was dried under reduced pressure to obtain compound 55l. LCMS (ESI) m/z: 388.1 (M+1); $^1$H NMR (400 MHz, DMSO-d$_6$) δ 13.06 (br s, 1H), 8.36 (s, 1H), 8.17 (d, J=9.17 Hz, 1H), 7.99 (d, J=7.83 Hz, 1H), 7.65 (d, J=9.17 Hz, 1H), 7.52-7.35 (m, 3H), 7.32 (s, 1H), 3.87 (s, 3H).

Twelfth Step:

The compound 55l (600 mg, 1.55 mmol, 1 eq) was dissolved in phosphorus oxychloride (16.50 g, 107.61 mmol, 10 mL, 69.46 eq), and N,N-dimethylaniline (938.62 mg, 7.75 mmol, 981.82 μl, 5 eq) was added thereto and the reaction solution was heated and stirred for 2 hours. TLC (dichloromethane:methanol=10:1) showed that the reaction was complete. The reaction solution was concentrated under reduced pressure to obtain a crude compound 55m.

Thirteenth Step:

The compound 55m (700 mg, 1.73 mmol, 1 eq) was dissolved in 1,4-dioxane (20 mL), and TEA (2.79 g, 27.60 mmol, 3.84 mL, 16 eq) and N-Boc piperazine (2.57 g, 13.80 mmol, 8 eq) were added thereto at 0° C., then heated to 50° C. and stirred for 2 hours. LCMS showed that the reaction was complete, and detected the target product. The reaction was quenched by adding saturated aqueous ammonium chloride solution (100 mL) and extracted with ethyl acetate (50 mL*3), and the organic phase was concentrated under reduced pressure and purified by column chromatography (silicon oxide, petroleum ether:ethyl acetate=1:1) to obtain compound 55n. LCMS (ESI) m/z: 556.5 (M+1); $^1$H NMR (400 MHz, CDCl$_3$) δ 8.93 (s, 1H), 8.03 (d, J=9.05 Hz, 1H), 7.86 (d, J=7.46 Hz, 1H), 7.44-7.36 (m, 3H), 7.35-7.30 (m, 1H), 7.05 (s, 1H), 3.90 (s, 3H), 3.83-3.78 (m, 4H), 3.69 (dd, J=3.85, 6.30 Hz, 4H), 1.52 (s, 9H).

Fourteenth Step:

The compound 55n (800 mg, 1.44 mmol, 1 eq) was dissolved in DCM (10 mL), TFA (4.62 g, 40.52 mmol, 3 mL, 28.14 eq) was added thereto and the reaction solution was stirred for 1 hour. LCMS showed that the reaction was complete, and detected the target product. The reaction solution was concentrated under reduced pressure to obtain the trifluoroacetate of compound 55o. LCMS (ESI) m/z: 456.2 (M+1);

Fifteenth Step:

The trifluoroacetate of the compound 55o (800 mg, 1.40 mmol, 1 eq) was dissolved in DCM (15 mL), TEA (1.42 g, 14.05 mmol, 1.96 mL, 10 eq) and acryloyl chloride (254.30 mg, 2.81 mmol, 229.10 μl, 2 eq) were added thereto at 0° C. and stirred for 0.5 hour at 0° C. LCMS showed that the reaction was complete, and detected the target product.

The reaction was quenched by adding saturated ammonium chloride (20 mL) and extracted with ethyl acetate (20 mL*2). The organic phases were combined and concentrated under reduced pressure. The resulting crude product was slurried (ethyl acetate:petroleum ether=1:2, 12 mL) and filtered, and the filter cake was dried under reduced pressure to obtain compound 55p. LCMS (ESI) m/z: 510.2 (M+1);

Sixteenth Step:

The compound 55p (200 mg, 392.56 μmol, 1 eq) was dissolved in DCM (10 mL), boron tribromide (2.95 g, 11.78 mmol, 1.13 mL, 30 eq) was added thereto at 0° C. and reacted for 1 hour at 25° C. LCMS showed that about 22.82% of the product was produced. The reaction was quenched by slowly adding water (30 mL) at 0° C. and extracted with ethyl acetate (30 mL*2); the organic phases were combined and concentrated under reduced pressure; the resulting residue was purified by preparative TLC (dichloromethane:methanol=20:1) and then by preparative HPLC (0.075% trifluoroacetic acid) to obtain the trifluoroacetate of example 55. LCMS (ESI) m/z: 496.2 (M+1); $^1$H NMR (400 MHz, DMSO-d$_6$) δ 10.33 (br s, 1H), 8.82 (s, 1H), 8.01-7.87 (m, 2H), 7.44-7.2344 (m, 5H), 6.83 (dd, J=16.69, 10.45 Hz, 1H), 6.18 (dd, J=16.69, 2.14 Hz, 1H), 5.81-5.70 (m, 1H), 3.99-3.73 (m, 8H).

Experimental Example 1: Cell Experiment

Experiment Purpose:

This experiment is intended to verify that the compounds of the present invention have an inhibitory effect on the proliferation of NCI-H358 human non-small cell lung cancer cells with KRAS G12C mutation, MIA PaCa2 human pancreatic cancer cells with KRAS G12C mutation and wild-type A375 human malignant melanoma cells.

Main Reagents:

cell line NCI-H358, cell line A375, cell line MIA Paca2, Cell Titer-Glo detection kit, RPMI1640 culture medium, DMEM cell culture medium, fetal bovine serum, 0.25% trypsin-EDTA digestion solution, DPBS, cell culture grade DMSO, and mycillin Main Instruments:

multi-label microplate detector Envision, cell culture flask, 384 cell culture microplate, Vi-cell XR cell viability analyzer, CO$_2$ constant temperature incubator, 300 μL 12-channel electric pipette, and Echo ultrasonic nanoliter-level liquid workstation Experiment Method:

40 μl of phosphate buffer was added to the peripheral wells of three 384-well microplates respectively, and 40 μl of cell suspension to be tested was added to the other wells of each plate respectively (plate 1: NCI-H358 cell suspension containing 500 NCI-H358 cells; plate 2: MIAPaCa2 cell suspension containing 300 MIAPaCa2 cells; plate 3: A375 cell suspension containing 300 A375 cells). The three cell plates were then placed in a carbon dioxide incubator and incubated overnight. Echo was used to perform a 3-fold gradient dilution of the compounds to be tested, and each compound was diluted with 10 concentration gradients (diluted from 50 μM to 0.003 μM), 100 nl of which was respectively added to the corresponding wells of the cell plates; after dosing, 40 μL of phosphate buffer was added to each well of rows A and P and columns 1 and 24, and then the cell plates were put back to the carbon dioxide incubator for culturing for 5 days. 20 μl of Promega CellTiter-Glo reagent per well was added to the cell plates, which was shaken at room temperature for 10 minutes in the dark to stabilize the luminescence signal. A PerkinElmer Envision multi-label analyzer was used for reading.

Data analysis: $IC_{50}$ results were analyzed by GraphPad Prism 5.0 software from IDBS.

Experiment Results:

The data of the anti-proliferative activity $IC_{50}$ of the compounds of the present invention on the NCI-H358 (G12C mutation) cell, A375 (wild-type) cell and MIA PaCa2 (G12C mutation) cell were shown in Table 1 and Table 2.

Conclusion: The compounds of the present invention show higher cellular anti-proliferative activity against the KRAS G12C mutant cell NCI-H358 and MIA PaCa2, and weaker anti-proliferative activity against the wild-type A375 cell, reflecting high selectivity.

TABLE 1

| Test compounds | NCI-H358 $IC_{50}$ (μM) | A375 $IC_{50}$ (μM) |
| --- | --- | --- |
| Example 1 | 5.3 | 17.8 |
| Example 2 | 5.36 | >50 |
| Example 6 | 14.64 | 39.85 |
| Formate of example 8 | 1.41 | 39.09 |
| Example 11 | 23.99 | 42.21 |
| Example 12 | 14.18 | 9.89 |
| Example 15 | 13.86 | >50 |
| Example 18 | 7.18 | 2.86 |
| Example 22 | 5.12 | 24.41 |
| Example 26 | 13.30 | 32.58 |
| Example 27 | 20.8 | 50 |
| Example 28 | 9.93 | 36.18 |
| Example 31 | 1.64 | 33.29 |
| Example 32 | 0.45 | 29.26 |
| Example 33 | 15.82 | 39.64 |
| Formate of example 34 | 1.05 | 28.30 |
| Example 37 | 1.05 | 19.69 |
| Example 41 | 0.15 | 12.24 |
| Example 42 | 0.01 | 4.57 |
| Example 44 | 3.67 | 9.02 |
| Example 45 | 0.01 | 6.24 |
| Example 46 | 1.95 | >50 |
| Example 47 | 1.00 | 27.88 |
| Example 48 | 0.18 | 20.79 |
| Example 49 | 0.05 | 7.32 |
| Example 50 | 5.49 | >50 |
| Example 51 | 2.04 | 8.82 |
| Example 52 | 0.06 | 7.39 |
| Example 53 | 2.27 | 8.91 |
| Example 54 | 0.29 | 6.66 |
| Trifluoroacetate of example 55 | 4.26 | 50 |

TABLE 2

| Test compounds | MIA PaCa2 $IC_{50}$ (μM) |
| --- | --- |
| Example 2 | 6.48 |
| Example 6 | 12.7 |
| Formate of example 8 | 2.31 |
| Example 25 | 15.27 |
| Example 31 | 1.25 |
| Example 32 | 0.37 |
| Example 35 | 12.04 |
| Example 36 | 1.11 |
| Example 37 | 1.44 |
| Example 41 | 0.16 |
| Example 42 | 0.02 |
| Example 44 | 2.97 |
| Example 45 | 0.01 |
| Example 46 | 1.79 |
| Example 47 | 0.82 |
| Example 48 | 0.13 |
| Example 49 | 0.07 |
| Example 50 | 3.90 |

Experimental Example 2: Liver Microsome Stability Test

Experiment Purpose:

To test the metabolic stability of the test article in mice, rats and human liver microsomes.

Experiment Materials:

test article (10 mM), testosterone (control article, 10 mM), diclofenac (control article, 10 mM), propafenone (control article, 10 mM), human liver microsomes, rat liver microsomes, and mouse liver microsomes.

Buffer System:

1. 100 mM potassium phosphate buffer (pH 7.4).
2. 10 mM magnesium dichloride solution.

Compound Dilution:

1. Intermediate solution: using 45 μL of DMSO (with 450 μL of 1:1 methanol/water) to dilute 5 μL of the test or control article.
2. Working solution: using 450 μL of 100 mM potassium phosphate buffer to dilute the intermediate solution.

NADPH Regeneration System:

1. β-Phosphoamide adenine dinucleotide, from Sigma, Cat. No. N0505.
2. Isocitrate, from Sigma, Cat. No. I1252.
3. Isocitrate dehydrogenase, from Sigma, Cat. No. I2002.

Preparation of Liver Microsome Solution (Final Concentration: 0.5 mg Protein/mL):

Stopping Solution:

Cold acetonitrile containing 100 ng/mL of tolbutamide and 100 ng/mL of labetalol as an internal standard substance.

Experiment Method:

1. 10 μL of the test or control article working solution was added to all plates (T0, T5, T10, T20, T30, T60, NCF60).
2. Liver microsome solution was dispensed into a 96-well plate at 680 μL/well, and addition was performed on each plate at 80 μL/well, and the above-mentioned incubation plate was placed at 37° C. for pre-incubation for about 10 minutes.
3. 10 μL of 100 mM potassium phosphate buffer was added to each well of the NCF60 plate.
4. After the pre-incubation, the NADPH regeneration system working solution was dispensed into the 96-well plate at 90 μL/well, and addition was performed on each plate at 10 μL/well to start the reaction.
5. Incubation was performed for an appropriate time (e.g., 5, 10, 20, 30 and 60 minutes).

6. 300 μL of the stopping solution (refrigerated at 4° C., containing 100 ng/mL of tolbutamide and 100 ng/mL of labetalol) was respectively added to each sample well.

7. The sample plate was shaken well for about 10 minutes and centrifuged at 4000 rpm for 20 minutes at 4° C.

8. During centrifugation, 300 μL of HPLC water was added to each well and 100 μL of supernatant was taken for LC-MS/MS analysis.

Data Analysis:

$T_{1/2}$ and $Cl_{int(mic)}$ were calculated by the following formula.

$$C_t = C_0 \cdot e^{-k_e \cdot t}$$

when $C_t = \frac{1}{2}C_0$, $$T_{1/2} = \frac{Ln2}{k_e} = \frac{0.693}{k_e}$$

$$CL_{int(mic)} = \frac{0.693}{T_{1/2}} \cdot \frac{1}{\text{microsomal protein concentration during incubation (mg/mL)}}$$

$$CL_{int(liver)} = CL_{int(mic)} \cdot \frac{\text{microsomal protein (mg)}}{\text{liver weigh (g)}} \cdot \frac{\text{liver weight (g)}}{\text{body weigt (kg)}}$$

Liver per gram contains 45 mg of microsomal proteins, and the liver weights of mice, rats, dogs, monkeys and humans are 88 g/kg, 40 g/kg, 32 g/kg, 30 g/kg and 20 g/kg, respectively.

$C_t$ is the concentration at time t, with t being the incubation time; $C_0$ is the concentration at 0; $K_e$ is the elimination rate constant; $Cl_{int(mic)}$ is the intrinsic clearance rate of liver microsomes; and $Cl_{int(liver)}$ is the hepatic intrinsic clearance rate.

$CL_{int(mic)}$=0.693/half-life/mg microsomal protein per mL (microsome concentration during incubation)

$CL_{int(liver)}$=$CL_{int(mic)}$×mg microsomal protein/g liver weight×ratio of liver weight to body weight Experiment results: See Table 3.

Experiment Conclusion:

The compounds of the present invention show a longer half-life in the liver microsome stability test of humans, rats and mice, and thus it can be speculated that the compounds of the present invention have better metabolic stability in vivo.

TABLE 3

| Test compounds | Human/rat/mouse $T_{1/2}$ (min) | | |
|---|---|---|---|
| Example 2 | >145 | >145 | >145 |
| Example 9 | >145 | 46.3 | >145 |
| Example 29 | >145 | >145 | >145 |
| Example 32 | >145 | >145 | >145 |
| Example 36 | >145 | >145 | >145 |

Experimental Example 3: Rat Pharmacokinetic Evaluation Experiment

Experiment Purpose:

To determine the drug concentrations in plasma at different times after intravenous and intragastric administration of the test compounds to the rats by using the LC/MS/MS method and using male SD rats as the test animals; To study the pharmacokinetic behaviors of the test compounds in rats and to evaluate the pharmacokinetic characteristics thereof.

Experiment scheme: 10 healthy adult male SD rats were used as experimental animals and divided into 4 groups according to the principle of similar body weight, with 2 in each group of the group IV (two groups) and 3 in each group of the group PO (two groups). The animals were purchased from Beijing Vital River Laboratory Animal Technology Co., Ltd.

Drug Preparation:

Group IV: an appropriate amount of samples were weighed; an appropriate amount of DMSO, PEG400 and water were added successively thereto according to the volume ratio of 10:60:30; and stirring was performed under sonication to reach a clear state of 1.5 mg/mL.

Group PO: an appropriate amount of samples were weighed; an appropriate amount of DMSO, PEG400 and water were added successively thereto according to the volume ratio of 10:60:30; and stirring was performed under sonication to reach a clear state of 1.0 mg/mL.

Administration:

After fasting overnight, each rat in the group IV was administered intravenously with a volume of 2 mL/kg and a dose of 3 mg/kg; each rat in the group PO was administered intragastrically with a volume of 10 mL/kg and a dose of 10 mg/kg.

Experiment Operation:

After each of the male SD rats in the group IV was administrated with the test compounds, 200 ul of blood samples were collected at 0.0833, 0.25, 0.5, 1, 2, 4, 6, 8 and 24 hours, and were placed in a commercial anticoagulation tube pre-loaded with EDTA-$K_2$. After each rat in the group PO was administrated with the test compounds, 200 ul of blood samples were collected at 0.25, 0.5, 1, 2, 4, 6, 8 and 24 hours respectively, and were placed in a commercial anticoagulation tube pre-loaded with EDTA-$K_2$. The test tube was centrifuged for 15 minutes to separate the plasma and stored at −60° C. 2 hours after administration, the animals can be fed. The content of the test compounds in plasma was determined by the LC/MS/MS method after intravenous and intragastric administration to the rats. The linear range of the method was from 2.00 to 6000 nM; plasma samples were analyzed after treatment of precipitating proteins by acetonitrile.

Experiment Results:

Experiment results were shown in Table 4.

Experiment Conclusion:

In the rat pharmacokinetic evaluation experiment, the compounds of the present invention show higher exposure and better oral availability than the reference compound ARS-1620.

TABLE 4

| Groups | | ARS-1620 | Example 49 |
| --- | --- | --- | --- |
| IV (3 mg/kg) | Cl (mL/Kg/min) | 36.3 | 20.6 |
| | $V_d$ (L/kg) | 1.08 | 2.15 |
| | AUC (nM · h) | 3206 | 4619 |
| | $T_{1/2}$ (h) | 0.462 | 0.940 |
| PO (10 mg/kg) | $C_{max}$ (nM) | 1244 | 2113 |
| | $T_{max}$ (h) | 0.333 | 1.67 |
| | AUC (nM · h) | 2316 | 7739 |
| | F (%) | 22.0 | 52.0 |

Note: Cl: clearance rate; $V_d$: volume of distribution; AUC: exposure; $T_{1/2}$: half-life; $C_{max}$: maximum compound concentration after oral administration; $T_{max}$: time to reach $C_{max}$; F: bioavailability.

Experimental Example 4: In Vivo Drug Efficacy Test (1)

Experiment Purpose:

To evaluate the in vivo efficacy of the test compounds in a subcutaneous xenograft tumor model of human pancreatic cancer MIA-PaCa2 cell.

Experiment Operation:

BALB/c nude mice, female, 6-8 weeks old, weighing approximately 18-22 grams. Each mouse was subcutaneously inoculated with 0.2 mL ($1\times10^7$) of MIA-PaCa2 cells (plus matrigel, with the volume ratio being 1:1) on the right back. The administration was performed when the average tumor volume reached about 169 cubic millimeters. The test compounds were orally administered daily, and the administration dose was shown in Table 5. The tumor volume was measured twice a week, with the volume measured in cubic millimeters, and calculated by the following formula: $V=0.5 a\times b^2$, where a and b were the long and short diameters of the tumor, respectively. The tumor suppressive effect of the compounds was evaluated by TGI (%). TGI (%) reflects the tumor growth inhibition rate. Calculation of TGI (%): TGI (%)=[(1−(average tumor volume at the end of administration in a treatment group−average tumor volume at the beginning of administration in the treatment group))/(average tumor volume at the end of treatment in the solvent control group−average tumor volume at the beginning of treatment in the solvent control group)]×100%.

Experiment results: See Table 5.

TABLE 5

| Groups | Tumor volume (mm³) (day 20) | TGI (%) |
| --- | --- | --- |
| Solvent control group | 612 ± 75 | — |
| Example 2 (50 mg/kg) | 457 ± 94 | 35 |
| Example 2 (200 mg/kg) | 307 ± 61 | 69 |

Experiment Conclusion:

The compounds of the present invention show good in vivo drug efficacy in a subcutaneous xenograft tumor model of human pancreatic cancer MIA-PaCa2 cell. 20 days after administration, the compounds of the present invention have a significant tumor suppressive effect compared with the solvent control group, and have an obvious dose-effect relationship.

Experimental Example 5: In Vivo Drug Efficacy Test (2)

Experiment Purpose:

To evaluate the in vivo efficacy of the test compounds in a subcutaneous xenograft tumor model of human non-small cell lung cancer NCI-H358.

Experiment Operation:

BALB/c nude mice, female, 6-8 weeks old, weighing 18-21 grams. A total of 100 were required. They were provided by Shanghai Lingchang Experimental Animal Co., Ltd (上海灵畅实验动物有限公司). NCI-H358 tumor cells were resuspended in PBS to prepare 0.1 mL ($5\times10^6$) of cell suspension, which was inoculated subcutaneously on the right back of each mouse ($5\times10^6$/mouse) to wait for tumor growth. When the average tumor volume reached about 150-200 mm³, randomized grouping and administration were performed, and the administration dose was shown in Table 6. The diameter of the tumor was measured with vernier calipers twice a week. The formula for calculating the tumor volume is: $V=0.5 a\times b^2$, wherein a and b represent the long and short diameters of the tumor, respectively. The tumor suppressive effect of the compounds was evaluated by TGI (%). TGI (%) reflects the tumor growth inhibition rate. Calculation of TGI (%): TGI (%)=[(1−(average tumor volume at the end of administration in a treatment group−average tumor volume at the beginning of administration in the treatment group))/(average tumor volume at the end of treatment in the solvent control group−average tumor volume at the beginning of treatment in the solvent control group)]×100%.

Experiment results: See Table 6.

TABLE 6

| Groups | Tumor volume (mm³) (day 20) | TGI (%) |
| --- | --- | --- |
| Solvent control group | 701 | — |
| ARS-1620 100 mg/kg (0-6 days) + 50 mg/kg (7-20 days) | 216 | 90.82 |
| Example 42 100 mg/kg (0-6 days) + 50 mg/kg (7-20 days) | 191 | 95.51 |
| Example 49 100 mg/kg (0-6 days) + 50 mg/kg (7-20 days) | 30 | 125.66 |

Experiment conclusion: The compounds of the present invention show good in vivo drug efficacy in a subcutaneous xenograft tumor model of human non-small cell lung cancer NCI-H358. 20 days after administration, the compounds of the present invention have a significant tumor suppressive effect compared with the reference compound ARS-1620.

Experimental Example 6: In Vivo Drug Efficacy Test (3)

Experiment Purpose:

To evaluate the in vivo efficacy of the test compounds in a subcutaneous xenograft tumor model of human pancreatic cancer x-MIA-PaCa2 cell.

Experiment Operation:

NU/NU mice, female, 6-8 weeks old, weighing 17-20 grams. A total of 100 were required (additional 30% of animals were inoculated). They were provided by Beijing Vital River Science and Technology Co., Ltd. Each mouse was subcutaneously inoculated with 0.2 mL ($10\times10^6$) of x-MIA-PaCa2 cells (plus matrigel, with the volume ratio being 1:1) on the right back. When the average tumor volume reached about 150 mm³, grouping and administration were performed, and the administration dose was shown in Table 7. The diameter of the tumor was measured with vernier calipers twice a week. The formula for calculating the tumor volume is: V=0.5a×b², wherein a and b represent the long and short diameters of the tumor, respectively. The tumor suppressive effect of the compounds was evaluated by TGI (%). TGI (%) reflects the tumor growth inhibition rate. Calculation of TGI (%): TGI (%)=[(1−(average tumor volume at the end of administration in a treatment group−average tumor volume at the beginning of administration in the treatment group))/(average tumor volume at the end of treatment in the solvent control group−average tumor volume at the beginning of treatment in the solvent control group)]×100%.

Experiment results: See Table 7.

TABLE 7

| Groups | Tumor volume (mm³) (day 14) | TGI (%) |
| --- | --- | --- |
| Solvent control group | 1670 | — |
| ARS-1620 (50 mg/kg) | 907 | 50.36 |
| Example 49 (50 mg/kg) | 204 | 96.77 |

Experiment conclusion: The compounds of the present invention show good in vivo drug efficacy in a subcutaneous xenograft tumor model of human pancreatic cancer x-MIA-PaCa2 cell. 14 days after administration, the compounds of the present invention have a significant tumor suppressive effect compared with the reference compound ARS-1620.

Experimental Example 7: In Vivo Drug Efficacy Test (4)

Experiment Purpose:

To evaluate the in vivo efficacy of the test compounds in a subcutaneous xenograft tumor model of human non-small cell lung cancer NCI-H358.

Experiment Operation:

BALB/c nude mice, female, 6-8 weeks old, weighing 18-20 grams. A total of 40 were required. They were provided by Shanghai Lingchang Experimental Animal Co., Ltd (上海灵畅实验动物有限公司). NCI-H358 tumor cells were resuspended in PBS to prepare a cell suspension with a density of 5×10⁷/mL, which was inoculated subcutaneously on the right back of each mouse (0.1 mL, 5×10⁶/mouse) to wait for tumor growth. When the average tumor volume reached about 166 mm³, randomized grouping and administration were performed, and the administration dose was shown in Table 8. The diameter of the tumor was measured with vernier calipers twice a week.

The formula for calculating the tumor volume is: V=0.5a×b², wherein a and b represent the long and short diameters of the tumor, respectively. The tumor suppressive effect of the compounds was evaluated by TGI (%). TGI (%) reflects the tumor growth inhibition rate. Calculation of TGI (%): TGI (%)=[(1−(average tumor volume at the end of administration in a treatment group−average tumor volume at the beginning of administration in the treatment group))/(average tumor volume at the end of treatment in the solvent control group−average tumor volume at the beginning of treatment in the solvent control group)]×100%.

Experiment results: See Table 8.

TABLE 8

| Groups | Tumor volume (mm³) (day 27) | TGI (%) |
| --- | --- | --- |
| Solvent control group | 842 | — |
| ARS-1620 15 mg/kg | 492 | 51.78 |
| Example 49 5 mg/kg | 117 | 107.25 |
| Example 49 15 mg/kg | 56 | 116.27 |
| Example 49 50 mg/kg (0-2 days) + 1.5 mg/kg (3-27 days) | 295 | 80.92 |

Experiment conclusion: 27 days after administration, at the same administration dose (15 mg/kg), the compounds of the present invention have a significant tumor suppressive effect compared with the reference compound ARS-1620. In addition, the compounds of the present invention still show a significant tumor shrinkage effect when the administration dose (5 mg/kg) thereof is lower than that (15 mg/kg) of the reference compound ARS-1620. This indicates that the compounds of the present invention show good in vivo drug efficacy in a subcutaneous xenograft tumor model of human non-small cell lung cancer NCI-H358, and the anti-tumor effect thereof has a dose-dependent tendency.

What is claimed is:

1. A compound of formula (I) or a pharmaceutically acceptable salt thereof,

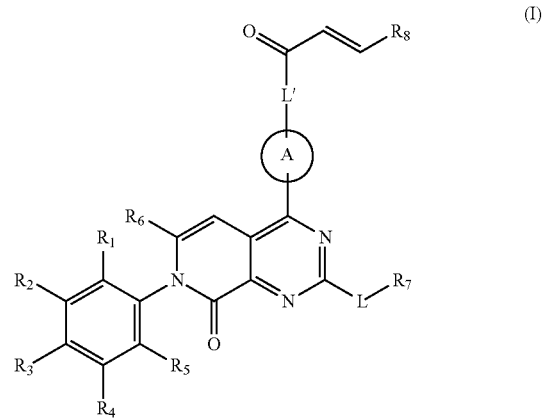

wherein ring A is selected from 3-8 membered heterocycloalkyl, and the 3-8 membered heterocycloalkyl is optionally substituted with 1, 2 or 3 R;

$R_1$, $R_2$, $R_3$, $R_4$ and $R_5$ are each independently selected from H, halogen, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3 R;

or $R_1$ and $R_2$ are connected together to form ring B;

or $R_2$ and $R_3$ are connected together to form ring B;

or $R_3$ and $R_4$ are connected together to form ring B;

or $R_4$ and $R_5$ are connected together to form ring B;

ring B is selected from phenyl, $C_{5-6}$ cycloalkenyl, 5-6 membered heterocycloalkenyl and 5-6 membered heteroaryl, and the phenyl, $C_{5-6}$ cycloalkenyl, 5-6 membered heterocycloalkenyl and 5-6 membered heteroaryl are optionally substituted with 1, 2 or 3 $R_a$;

$R_a$ is selected from halogen, OH, $NH_2$, CN, $C_{1-6}$ alkyl and $C_{1-6}$ heteroalkyl, and the $C_{1-6}$ alkyl and $C_{1-6}$ heteroalkyl are optionally substituted with 1, 2 or 3 R;

$R_6$ is selected from H, halogen and $C_{1-6}$ alkyl, and the $C_{1-6}$ alkyl is optionally substituted with 1, 2 or 3 R;

$R_7$ is selected from 4-6 membered heterocycloalkyl, 5-6 membered heteroaryl and $C_{5-6}$ cycloalkyl, and 4-6 membered heterocycloalkyl, 5-6 membered heteroaryl and $C_{5-6}$ cycloalkyl are optionally substituted with 1, 2 or 3 R;

L is selected from a single bond, —NH—, —S—, —O—, —C(=O)—, —C(=S)—, —CH$_2$—, —CH($R_b$)— and —C($R_b$)$_2$—;

L' is selected from a single bond and —NH—;

$R_b$ is selected from $C_{1-3}$ alkyl and $C_{1-3}$ heteroalkyl, and the $C_{1-3}$ alkyl and $C_{1-3}$ heteroalkyl are optionally substituted with 1, 2 or 3 R;

$R_8$ is selected from H, $C_{1-6}$ alkyl and $C_{1-6}$ heteroalkyl, and the $C_{1-6}$ alkyl and $C_{1-6}$ heteroalkyl are optionally substituted with 1, 2 or 3 R;

R is selected from halogen, OH, $NH_2$, CN, $C_{1-6}$ alkyl, $C_{1-6}$ heteroalkyl and $C_{3-6}$ membered cycloalkyl, and the $C_{1-6}$ alkyl, $C_{1-6}$ heteroalkyl and $C_{3-6}$ membered cycloalkyl are optionally substituted with 1, 2 or 3 R';

R' is selected from F, Cl, Br, I, OH, $NH_2$, CN, $CH_3$, $CH_3CH_2$, $CH_3O$, $CF_3$, $CHF_2$, $CH_2F$, cyclopropyl, propyl, isopropyl, $N(CH_3)_2$ and $NH(CH_3)$;

"hetero" means a heteroatom or a heteroatomic group, the "hetero" in the 3-8 membered heterocycloalkyl, $C_{1-6}$ heteroalkyl, 5-6 membered heterocycloalkenyl, 5-6 membered heteroaryl, 4-6 membered heterocycloalkyl and $C_{1-3}$ heteroalkyl is each independently selected from —C(=O)N(R)—, —N(R)—, —NH—, N, —O—, —S—, —C(=O)O—, —C(=O)—, —C(=S)—, —S(=O)—, —S(=O)$_2$— and —N(R)C(=O)N(R)—;

in any of the cases above, the number of heteroatoms or heteroatomic groups is each independently selected from 1, 2 and 3.

2. The compound or pharmaceutically acceptable salt thereof as defined in claim 1, wherein R is selected from F, Cl, Br, I, OH, $NH_2$, CN, $CH_3$, $CH_3CH_2$, $CH_3O$, $CF_3$, $CHF_2$, $CH_2F$, cyclopropyl, propyl, isopropyl, $N(CH_3)_2$, $NH(CH_3)$ and $N(CH_2CH_3)_2$.

3. The compound or pharmaceutically acceptable salt thereof as defined in claim 1, wherein ring A is selected from aziridinyl, azetidinyl, pyrrolidinyl, piperidyl, piperazinyl, 1,4-diazacycloheptyl and 3,6-diazabicyclo [3.2.0] heptyl, and the aziridinyl, azetidinyl, pyrrolidinyl, piperidyl, piperazinyl, 1,4-diazacycloheptyl and 3,6-diazabicyclo [3.2.0] heptyl are optionally substituted with 1, 2 or 3 R;

or, $R_1$, $R_2$, $R_3$, $R_4$ and $R_5$ are each independently selected from H, F, Cl, Br, I, OH, $NH_2$, CN, $CH_3$, $CH_3CH_2$, $(CH_3)_2CH$, $CH_3O$, $CH_3NH$ and $CH_3NH(C=O)O$, and the $CH_3$, $CH_3CH_2$, $(CH_3)_2CH$, $CH_3O$, $CH_3NH$ and $CH_3NH(C=O)O$ are optionally substituted with 1, 2 or 3 R;

or, ring B is selected from pyrazolyl, imidazolyl, pyrrolyl, thienyl, furyl, triazolyl, oxazolyl, isoxazolyl, thiazolyl, isothiazolyl, phenyl, pyridyl, pyrimidinyl, pyridazinyl, triazinyl, morpholinyl, cyclopentenyl and cyclohexenyl, and the pyrazolyl, imidazolyl, pyrrolyl, thienyl, furyl, triazolyl, oxazolyl, isoxazolyl, thiazolyl, isothiazolyl, phenyl, pyridyl, pyrimidinyl, pyridazinyl, triazinyl, morpholinyl, cyclopentenyl and cyclohexenyl are optionally substituted with 1, 2 or 3 $R_a$;

or, $R_a$ is selected from F, Cl, Br, I, OH, $NH_2$, CN, $CH_3$, $CH_3CH_2$, $(CH_3)_2CH$, $CH_3O$ and $CH_3C(=O)$;

or, $R_6$ is selected from H, F, Cl, Br, I and $C_{1-3}$ alkyl, and the $C_{1-3}$ alkyl is optionally substituted with 1, 2 or 3 R.

4. The compound or pharmaceutically acceptable salt thereof as defined in claim 3, wherein $R_1$, $R_2$, $R_3$, $R_4$ and $R_5$ are each independently selected from H, F, Cl, Br, I, OH, $NH_2$, CN, $CH_3$, $CH_3CH_2$, $(CH_3)_2CH$, $CH_3O$, $CH_3NH$, $(CH_3)_2N$, $(CH_3)_2N(C=O)O$ and $CH_3NH(C=O)O$;

or, ring B is selected from phenyl, pyrazolyl, 1-methyl-1H-pyrazolyl and 1-(1H-pyrazole-1-yl)ethanone group;

or, $R_6$ is selected from H, F, Cl, Br, I, $CH_3$, $CF_3$, $CHF_2$ and $CH_2F$.

5. The compound or pharmaceutically acceptable salt thereof as defined in claim 1, wherein $R_7$ is selected from morpholinyl, piperidyl, azetidinyl, azacyclopentanyl, pyrazolyl, imidazolyl, oxazolyl, isoxazolyl, thiazolyl, isothiazolyl, cyclohexyl, cyclopentanyl, phenyl, pyridyl, pyridazinyl, pyrimidinyl and pyrazinyl, and the morpholinyl, piperidyl, azetidinyl, azacyclopentanyl, pyrazolyl, imidazolyl, oxazolyl, isoxazolyl, thiazolyl, isothiazolyl, cyclohexyl, cyclopentanyl, phenyl, pyridyl, pyridazinyl, pyrimidinyl and pyrazinyl are optionally substituted with 1, 2 or 3 R.

6. The compound or pharmaceutically acceptable salt thereof as defined in claim 5, wherein $R_7$ is selected from

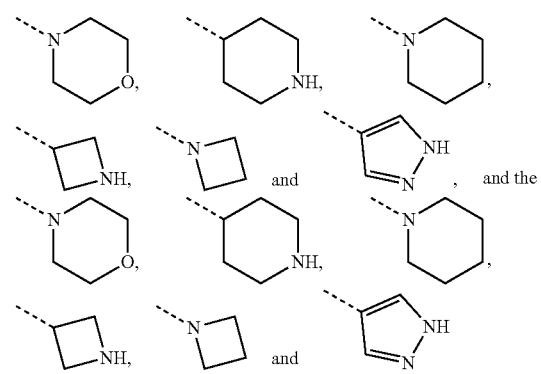

and the

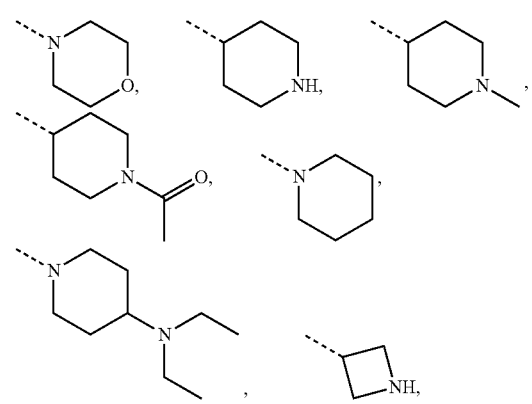

and are optionally substituted with 1, 2 or 3 R.

7. The compound or pharmaceutically acceptable salt thereof as defined in claim 6, wherein $R_7$ is selected from -continued

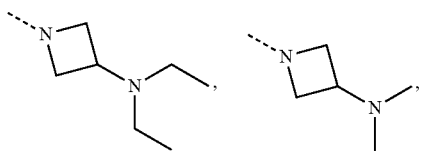

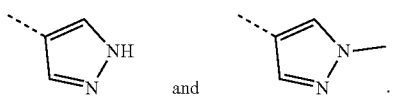

8. The compound or pharmaceutically acceptable salt thereof as defined in claim 1, wherein $R_8$ is selected from H, $C_{1-4}$ alkyl and $C_{1-4}$ heteroalkyl, and the $C_{1-4}$ alkyl and $C_{1-4}$ heteroalkyl are optionally substituted with 1, 2 or 3 R.

9. The compound or pharmaceutically acceptable salt thereof as defined in claim 8, wherein $R_8$ is selected from H, $CH_3$, $CH_3CH_2$, $(CH_3)_2CHCH_2$, $(CH_3)_2CH$, $CH_3O$, $CH_3NH$, $(CH_3)_2N$, $(CH_3)_2NCH_2$ and $CH_3NHCH_2$.

10. The compound or pharmaceutically acceptable salt thereof as defined in claim 1, wherein the structural unit

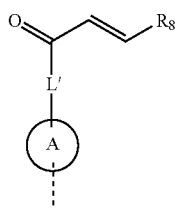

is selected from

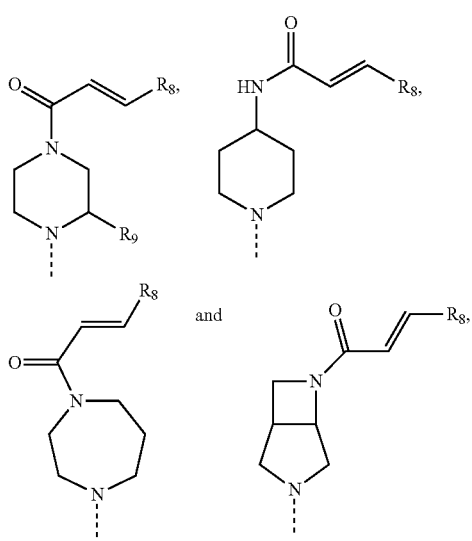

and wherein $R_9$ is selected from H and $C_{1-3}$ alkyl.

11. The compound or pharmaceutically acceptable salt thereof as defined in claim 10, wherein the structural unit

is selected from

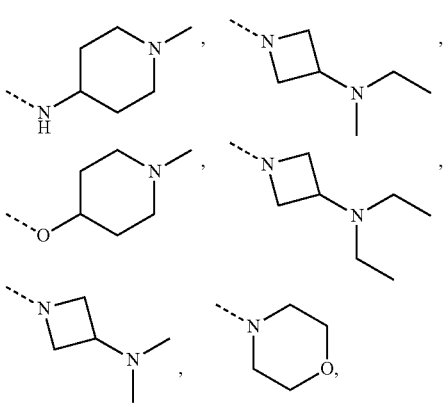

12. The compound or pharmaceutically acceptable salt thereof as defined in claim 1, wherein the structural unit is selected from

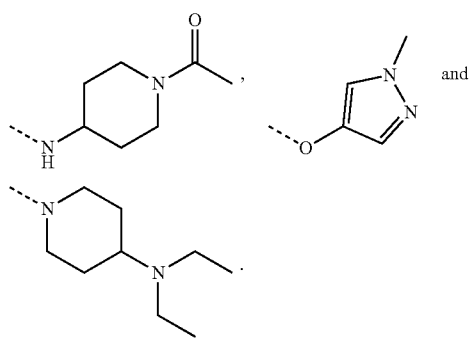
13. The compound or pharmaceutically acceptable salt thereof as defined in claim 1, wherein the structural unit
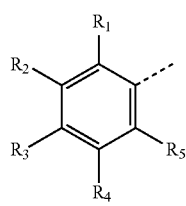
is selected from
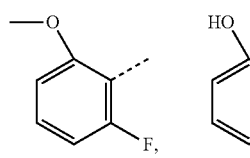 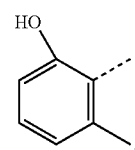
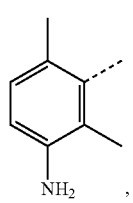 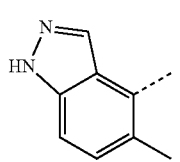 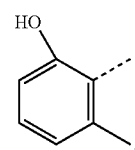
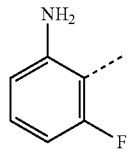 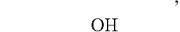 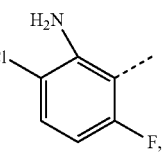
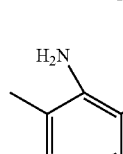 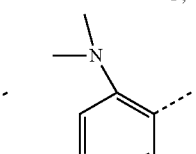 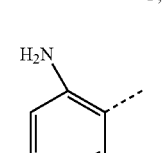
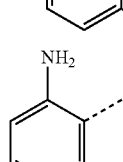 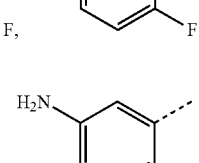 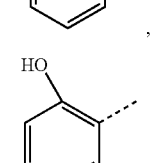
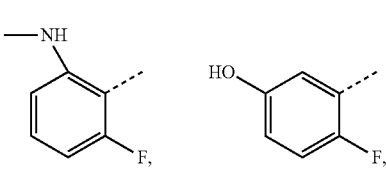
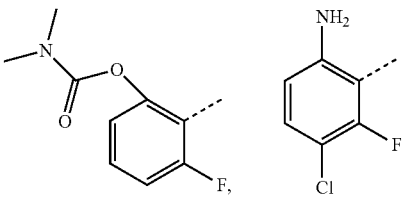
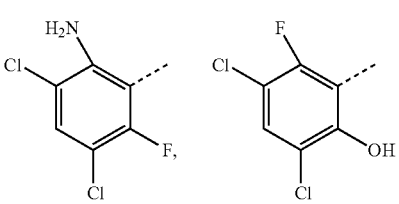
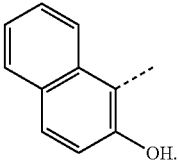 and
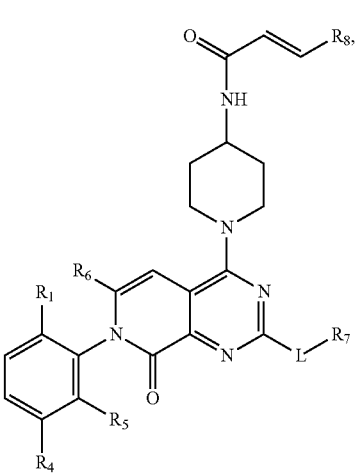
14. The compound or pharmaceutically acceptable salt thereof as defined in claim 1, selected from

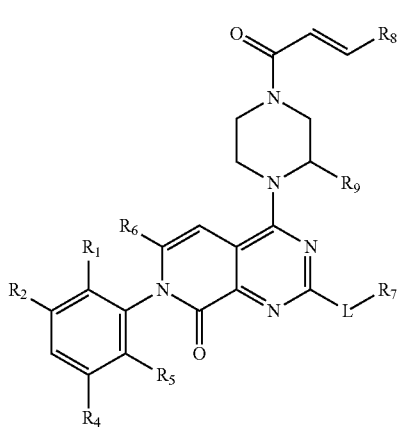
(III″)

and wherein L, R₁, R₂, R₄, R₅, R₆, R₇, and R₈ are as defined in claim 1,

R₉ is selected from H and C₁₋₃ alkyl.

15. The compound or pharmaceutically acceptable salt thereof as defined in claim 14, selected from

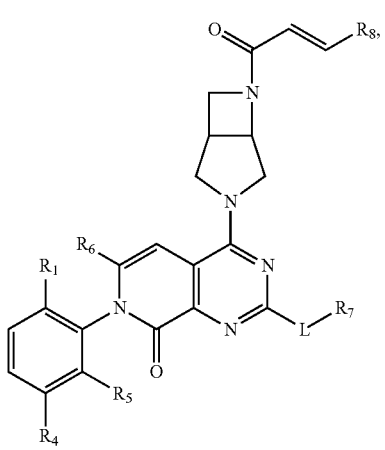
(IV)

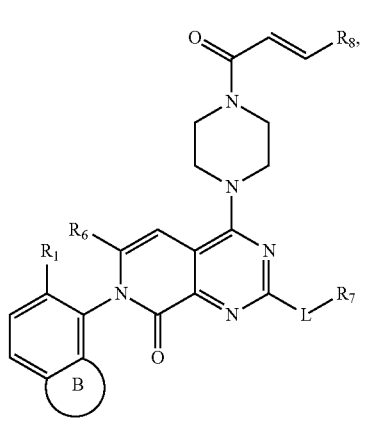
(VI)

and wherein R₁, R₂, R₄, R₅, R₆, R₇, R₈, R₉ and L are as defined in claim 14.

16. The compound or pharmaceutically acceptable salt thereof as defined in claim 15, selected from

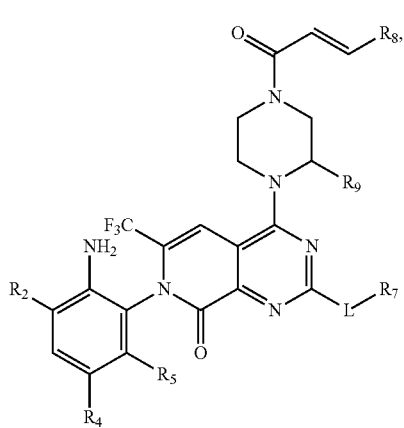
(III″-2)

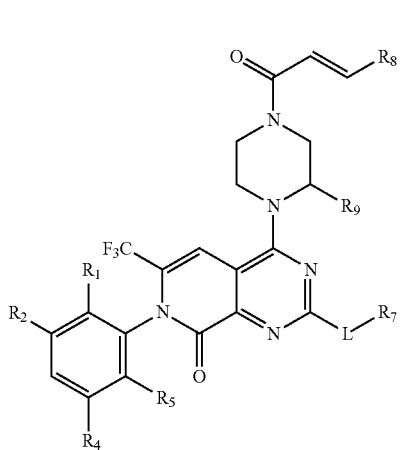
(III″-1) and

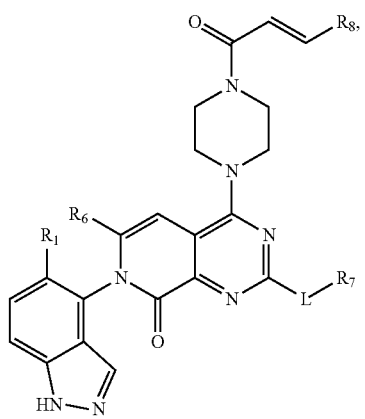
(VI-1)

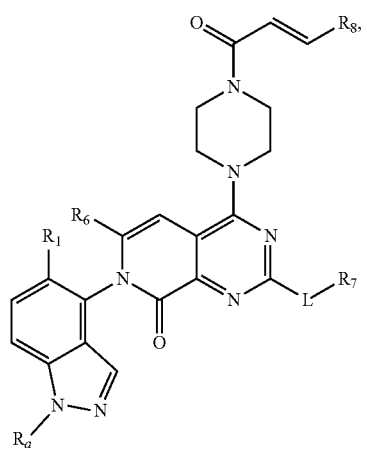
(VI-2)
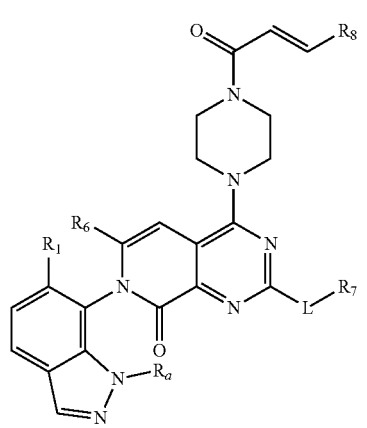
(VI-3) and
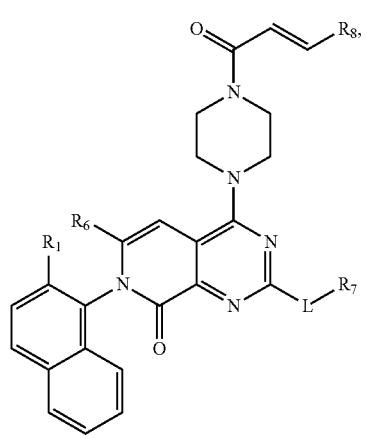
(VI-4)
and wherein R₁, R₂, R₄, R₅, R₆, R₇, R₈, L, R₉ and Rₐ are as defined in claim 15.
17. A compound of the following formula or a pharmaceutically acceptable salt thereof, selected from
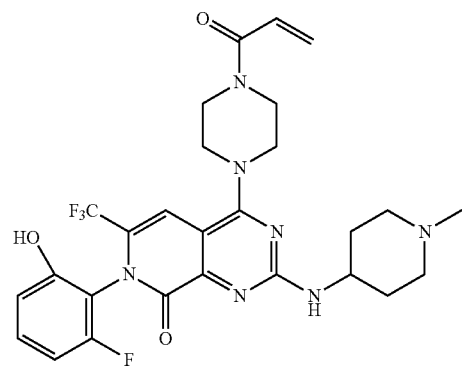
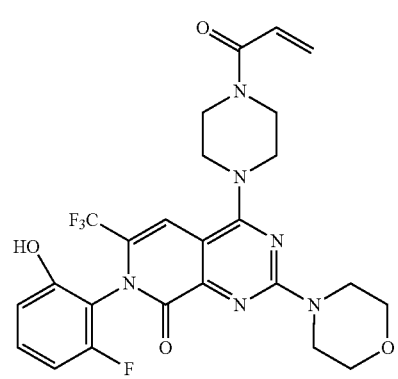
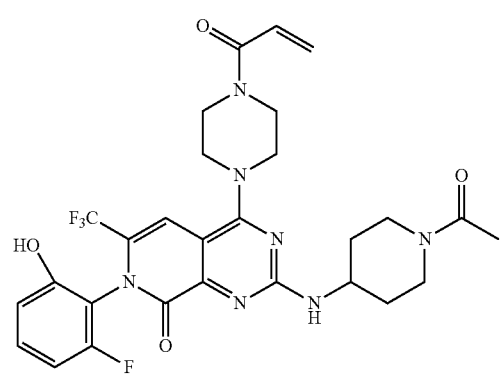
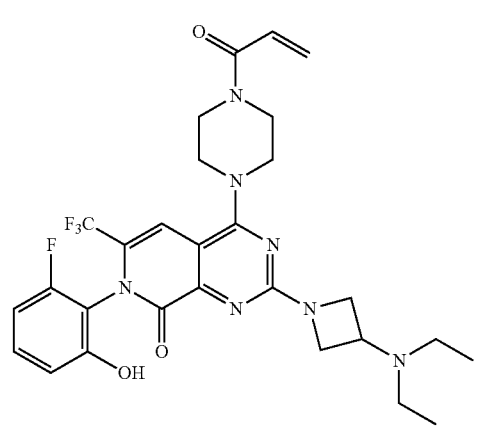

137
-continued
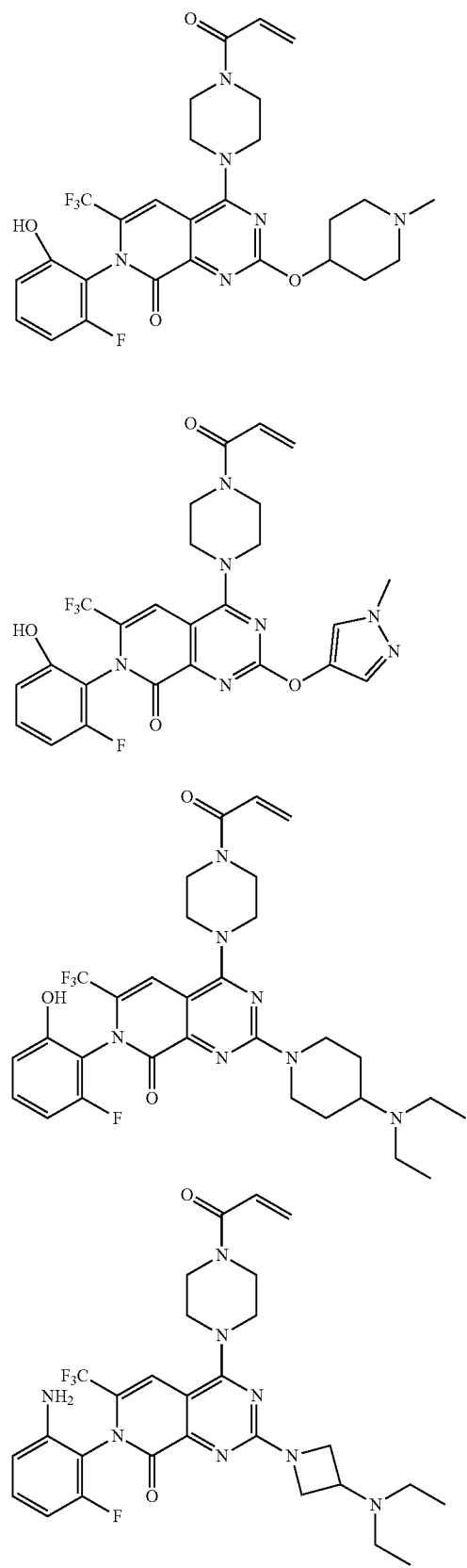
138
-continued
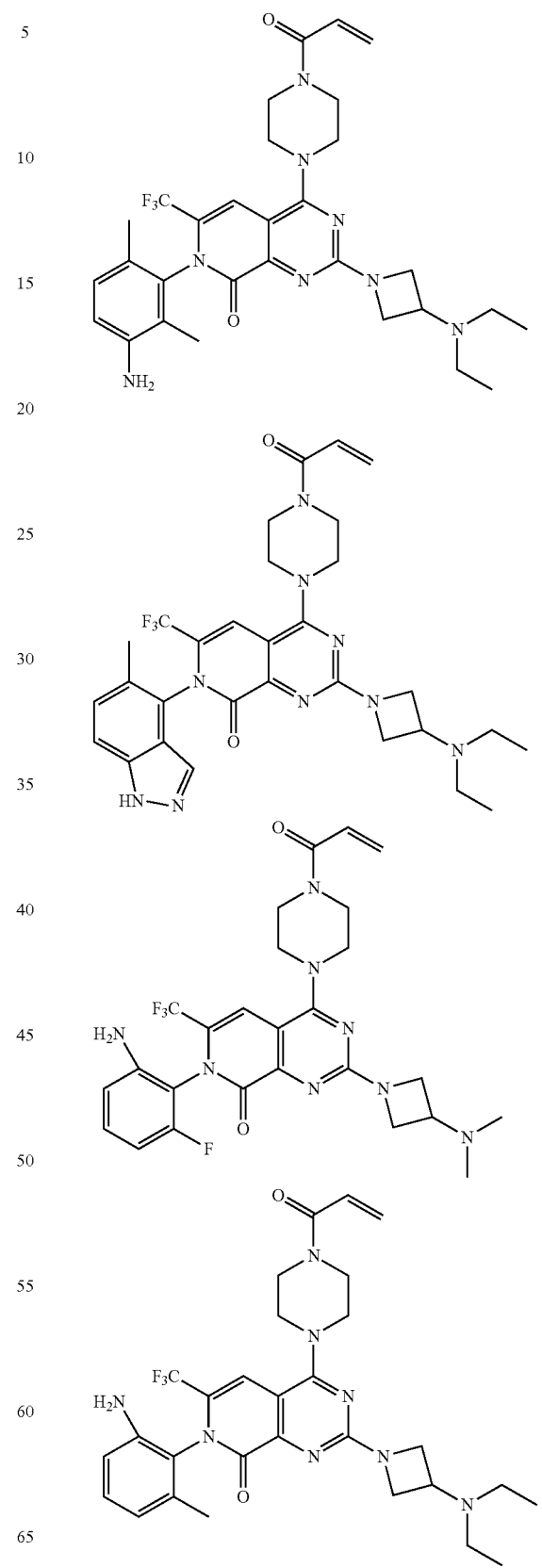

-continued
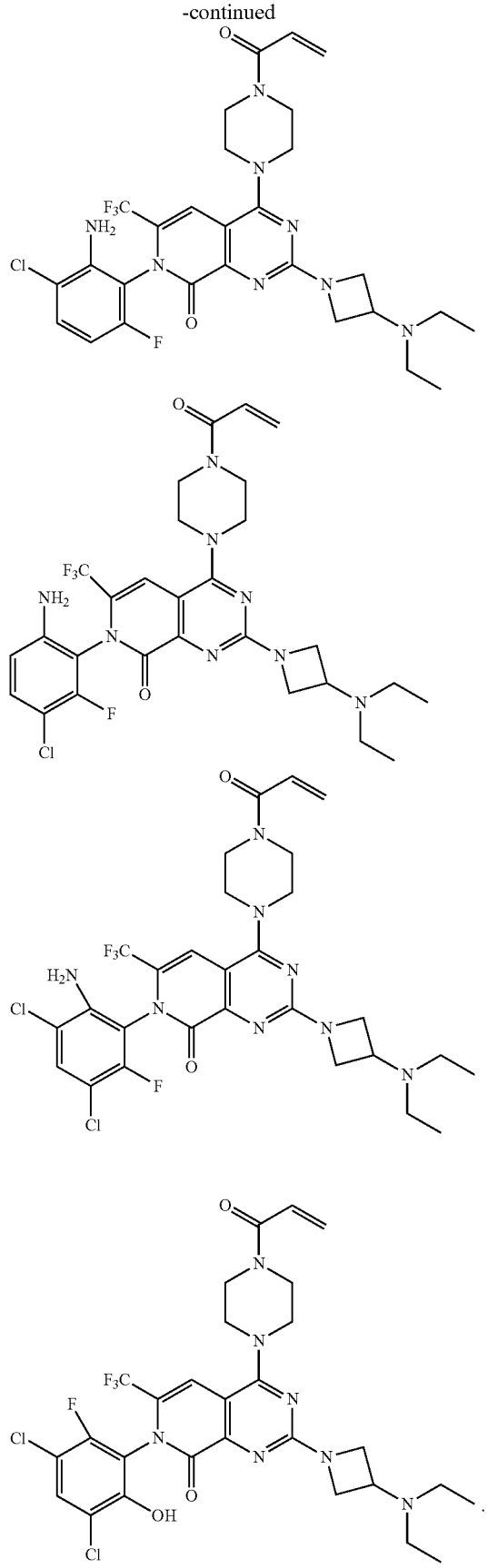
18. The compound or pharmaceutically acceptable salt thereof as defined in claim 17, selected from
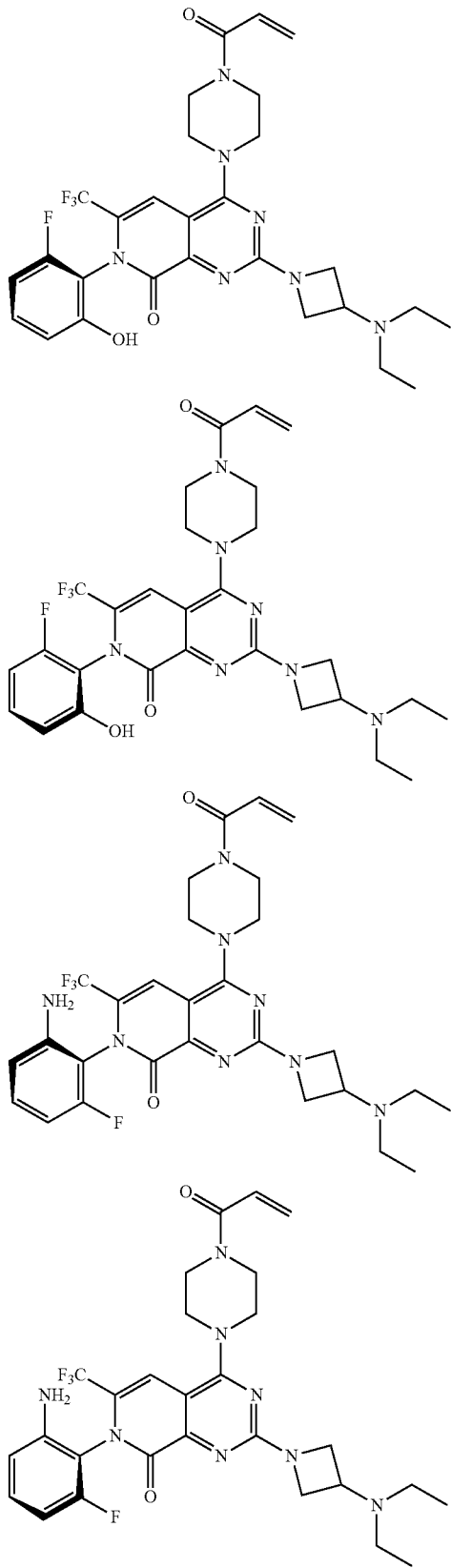

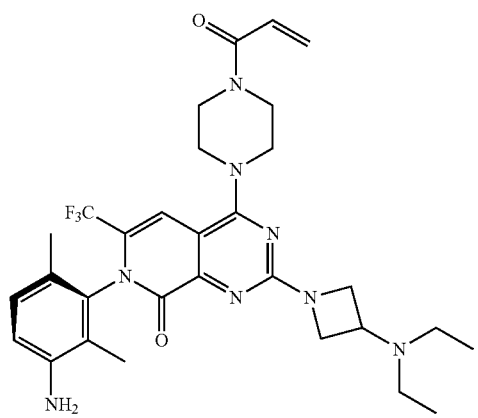

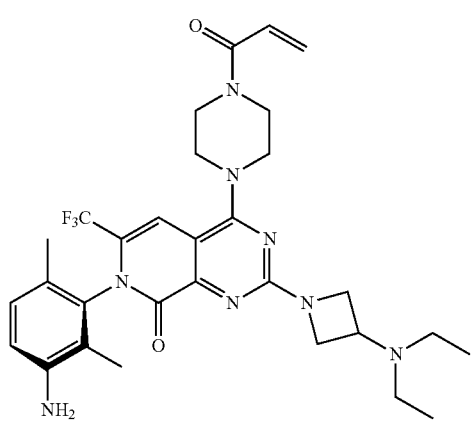

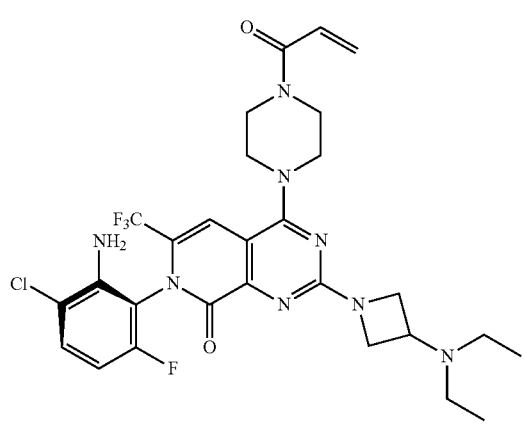

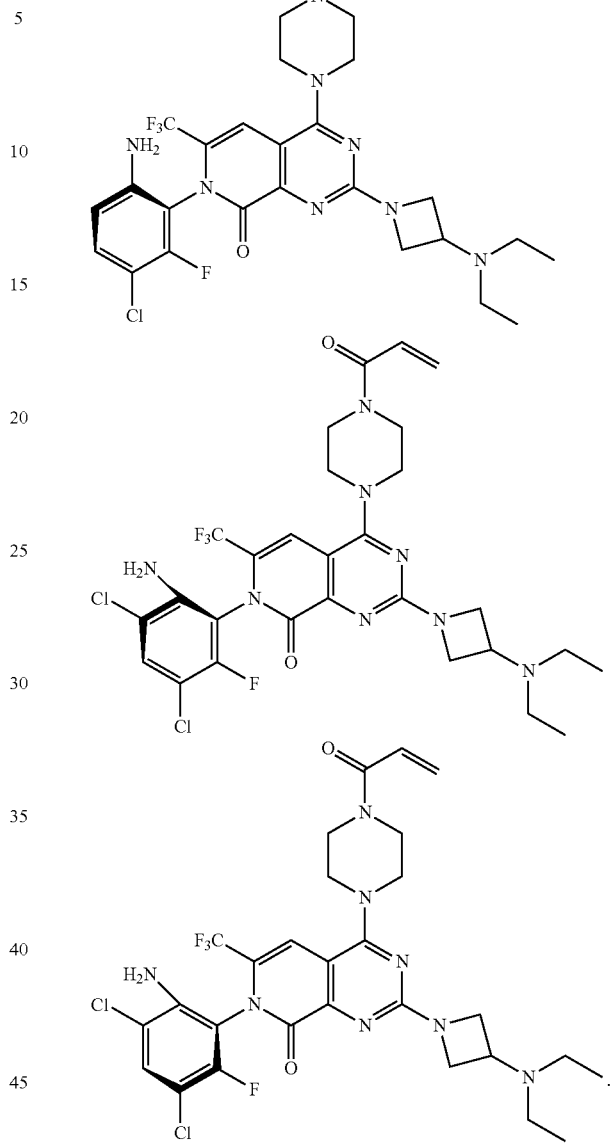

19. A method for treating cancer in a subject in need thereof, comprising administering an effective amount of the compound or pharmaceutically acceptable salt thereof as defined in claim 1 to the subject, wherein the cancer is selected from lung cancer, lymphoma, esophageal cancer, ovarian cancer, pancreatic cancer, rectal cancer, glioma, cervical cancer, urothelial cancer, gastric cancer, endometrial cancer, liver cancer, cholangiocarcinoma, breast cancer, colon cancer, leukemia and melanoma.

* * * * *